US011498954B2

(12) United States Patent
Gill et al.

(10) Patent No.: US 11,498,954 B2
(45) Date of Patent: *Nov. 15, 2022

(54) MODIFIED MONOCYTES/MACROPHAGE EXPRESSING CHIMERIC ANTIGEN RECEPTORS AND USES THEREOF

(71) Applicant: THE TRUSTEES OF THE UNIVERSITY OF PENNSYLVANIA, Philadelphia, PA (US)

(72) Inventors: Saar Gill, Philadelphia, PA (US); Michael Klichinsky, Philadelphia, PA (US); Carl H. June, Merion Station, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/691,842

(22) Filed: Mar. 10, 2022

(65) Prior Publication Data
US 2022/0281947 A1    Sep. 8, 2022

Related U.S. Application Data

(63) Continuation of application No. 16/858,183, filed on Apr. 24, 2020, now Pat. No. 11,306,133, which is a continuation of application No. 15/747,555, filed as application No. PCT/US2016/044440 on Jul. 28, 2016, now Pat. No. 11,034,749.

(60) Provisional application No. 62/197,675, filed on Jul. 28, 2015.

(51) Int. Cl.
| | |
|---|---|
| A61K 39/00 | (2006.01) |
| C07K 14/705 | (2006.01) |
| C07K 14/725 | (2006.01) |
| C07K 14/735 | (2006.01) |
| C07K 16/28 | (2006.01) |
| C07K 16/32 | (2006.01) |
| C12N 5/0786 | (2010.01) |
| C07K 19/00 | (2006.01) |
| C07K 16/30 | (2006.01) |
| A61K 35/15 | (2015.01) |
| A61K 35/14 | (2015.01) |
| A61P 35/00 | (2006.01) |
| A61K 38/00 | (2006.01) |

(52) U.S. Cl.
CPC ........ *C07K 14/70517* (2013.01); *A61K 35/15* (2013.01); *A61K 39/001106* (2018.08); *A61K 39/001112* (2018.08); *A61K 39/001168* (2018.08); *C07K 14/7051* (2013.01); *C07K 14/7056* (2013.01); *C07K 14/70535* (2013.01); *C07K 16/2803* (2013.01); *C07K 16/30* (2013.01); *C07K 16/32* (2013.01); *C07K 19/00* (2013.01); *C12N 5/0645* (2013.01); *A61K 35/14* (2013.01); *A61K 38/00* (2013.01); *A61K 2039/505* (2013.01); *A61K 2039/5154* (2013.01); *A61K 2039/5156* (2013.01); *A61K 2039/5158* (2013.01); *A61K 2039/892* (2018.08); *A61P 35/00* (2018.01); *C07K 2317/622* (2013.01); *C07K 2317/73* (2013.01); *C07K 2319/00* (2013.01); *C07K 2319/02* (2013.01); *C07K 2319/03* (2013.01); *C07K 2319/74* (2013.01); *C12N 2510/00* (2013.01)

(58) Field of Classification Search
None
See application file for complete search history.

(56) References Cited

U.S. PATENT DOCUMENTS

| | | |
|---|---|---|
| 3,334,764 A | 8/1967 | Fouser |
| 7,994,298 B2 | 8/2011 | Zhang et al. |
| 8,361,461 B2 | 1/2013 | Getsh et al. |
| 8,450,112 B2 | 5/2013 | Peshwa et al. |
| 9,132,153 B2 | 9/2015 | Peshwa et al. |
| 9,669,058 B2 | 6/2017 | Li et al. |
| 2004/0053837 A1 | 3/2004 | Li et al. |
| 2004/0053873 A1 | 3/2004 | Barman et al. |
| 2004/0126363 A1 | 7/2004 | Jensen et al. |
| 2007/0012614 A1 | 1/2007 | Yoshida |
| 2011/0287038 A1 | 11/2011 | Slawin et al. |
| 2011/0305638 A1 | 12/2011 | Ting et al. |

(Continued)

FOREIGN PATENT DOCUMENTS

| | | |
|---|---|---|
| CN | 101668777 A | 3/2010 |
| CN | 104829733 A | 8/2015 |

(Continued)

OTHER PUBLICATIONS

Extended European Search Report for European Patent Application No. 16831340.1 dated Mar. 6, 2019.
International Search Report and Written Opinion for PCT International Application No. PCT/US2016/044440 dated Oct. 21, 2016.
Search Report for Singapore Patent Application No. 11201800339R dated Apr. 22, 2019.
Andreesen, et al., "Adoptive transfer of tumor cytotoxic macrophages generated in vitro from circulating blood monocytes: a new approach to cancer immunotherapy", Cancer Res. 50(23), Dec. 1990, 7450-7456.

(Continued)

*Primary Examiner* — Michael D Burkhart
(74) *Attorney, Agent, or Firm* — Saul Ewing Arnstein & Lehr LLP; Kathryn Doyle

(57) ABSTRACT

The present invention includes methods and compositions for treating cancer, whether a solid tumor or a hematologic malignancy. By expressing a chimeric antigen receptor in a monocyte, macrophage or dendritic cell, the modified cell is recruited to the tumor microenvironment where it acts as a potent immune effector by infiltrating the tumor and killing the target cells. One aspect includes a modified cell and pharmaceutical compositions comprising the modified cell for adoptive cell therapy and treating a disease or condition associated with immunosuppression.

24 Claims, 50 Drawing Sheets

(56) References Cited

U.S. PATENT DOCUMENTS

| | | | |
|---|---|---|---|
| 2013/0287748 | A1 | 10/2013 | June et al. |
| 2014/0153114 | A1 | 6/2014 | Suzuki |
| 2014/0161799 | A1 | 6/2014 | Frazier et al. |
| 2014/0242701 | A1 | 8/2014 | Shiku et al. |
| 2014/0322212 | A1 | 10/2014 | Brogdon et al. |
| 2016/0176651 | A1 | 6/2016 | Landler et al. |
| 2016/0193696 | A1 | 7/2016 | McFarland et al. |
| 2017/0151281 | A1 | 6/2017 | Wagner et al. |
| 2017/0216354 | A1 | 8/2017 | Wagner et al. |
| 2017/0258837 | A1 | 9/2017 | Li et al. |
| 2018/0028567 | A1 | 2/2018 | Li et al. |
| 2022/0041688 | A1* | 2/2022 | Gill ................ A61K 35/15 |

FOREIGN PATENT DOCUMENTS

| | | |
|---|---|---|
| EP | 3334764 A2 | 6/2018 |
| JP | 2004529636 A | 9/2004 |
| JP | 2009523007 A | 6/2009 |
| JP | 2013525305 A | 6/2013 |
| RU | 2433825 C2 | 11/2011 |
| RU | 2434882 C2 | 11/2011 |
| WO | 02077029 A2 | 10/2002 |
| WO | 2006040330 A2 | 4/2006 |
| WO | 2007012614 A2 | 2/2007 |
| WO | 2008103947 A2 | 8/2008 |
| WO | 2013051718 A1 | 4/2013 |
| WO | 2014153114 A1 | 9/2014 |
| WO | 2016033331 A1 | 3/2016 |
| WO | 2016149254 A1 | 9/2016 |
| WO | 2016176651 A2 | 11/2016 |
| WO | 2016193696 A1 | 12/2016 |

OTHER PUBLICATIONS

Batrakova, et al., "Cell-Mediated Drugs Delivery", Expert Opin Drug Deliv. 8(4), Apr. 2011, 415-433.

Biglari, et al., "Human monocytes expressing a CEA-specific chimeric CD64 receptor specifically target CEA-expressing tumour cells in vitro and in vivo", Gene Ther. 13(7), Apr. 2006, 602-610.

Gill Saar, et al., 31st Annual Meeting and Associated Programs of the Society for Immunotherapy of Cancer (SITC 2016): part one; Journal for ImmunoTherapy of Cancer, 4(Suppl 1): P23, Dec. 2016, Abstract Only.

Khramtsova, et al., "The M2/Alternatively Activated Macrophage Phenotype Correlates with Aggressive Histopathologic Features and Poor Clinical Outcome in Early Stage Breast Cancer", Cancer Res 69(24) (Suppl. 3) Thirty-Second Annual CTRC-AACR San Antonio Breast Cancer Symposium—Dec. 10-13, 2009; San Antonio, TX, Dec. 2009, Abstract.

Klichinsky, et al., "Abstract 4575: Chimeric antigen receptor macrophages (CARMA) for adoptive cellular Immunotherapy of solid tumors", Proceedings: AACR Annual Meeting 2017; Washington, DC, Apr. 1-5, 2017, Abstract Only.

Klichinsky, et al., "Human Chimeric Antigen Receptor Macrophages for Cancer Immunotherapy", Nature Biotechnology, Mar. 2020, 1-13.

Levine, et al., "Global Manufacturing of CAR T Cell Therapy", Mol. Ther. Methods Clin. Dev. 4, Mar. 2017, 92-101.

Maude, et al., "Chimeric Antigen ReceptorT Cells for Sustained Remissions in Leukemia.", N Engl J Med. 371(16), Oct. 2014, 1507-1517.

Sharma, et al., "HER-2 pulsed dendritic cell vaccine can eliminate HER-2 expression and impact ductal carcinoma in situ", Cancer. 118(17), Sep. 2012, 4354-4362.

Villanueva, "Macrophages Get a CAR", Nature 19, May 2020, 308.

Wei, et al., "Cancer immunotherapy using in vitro genetically modified targeted dendritic cells", Cancer Res. 68(10), May 2008, 3854-3862.

Weiskopf, et al., "Engineered SIRPα variants as immunotherapeutic adjuvants to anti-cancer antibodies", Science 341(88), Jul. 2013, 88-91.

Weiskopf, et al., "Macrophages are critical effectors of antibody therapies for cancer", MAbs. 7(2), 2015, 303-310.

Yong, et al., "Using Electroporation to Determine Function of a Chimeric Antigen Receptor in T Cell and Macrophage Cell Lines", The Open Gene Therapy Journal 5, 2013, 1-11.

Porter, D.L et al., "Chimeric Antigen Receptor Therapy for B-cell Malignancies", J. Cancer, (Jun. 1, 2011), vol. 2, 331-332.

Grupp, et al., "CD19-Redirected Chimeric Antigen Receptor T(CART19) Cells Induce a Cytokine Release Syndrome (CRS) and Induction of Treatable Macrophage Activation Syndrome (MAS) That Can Be Managed by the IL-6 Antagonist Tocilizumab", Blood, (20120000), vol. 120, No. 21, p. 2604. Abstract.

Kochenderfer, et al., "B-cell depletion and remissions of malignancy along with cytokine-associated toxicity in a clinical trial of anti-CD19 chimeric-antigen-receptor-transduced T cells", Blood, (Dec. 8, 2011), vol. 119, No. 12, 2709-2720.

Yáñez, et al., "CAR T cell toxicity: current management and future directions." Hemasphere 3.2 (2019). 2-10.

Kochenderfer, et al., "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-of-Hematology (ASH); Orlando, FL, USA; Dec. 4-7, 2010 abstract.

Krüttgen, et al., "Interleukin-6 in Sepsis and Capillary Leakage Syndrome", Journal of Interferon and Cytokine Research., Mary Ann Liebert, New York, NY., US, US, (Feb. 1, 2012), vol. 32, No. 2, doi:10.1089/ir.2011.0062, ISSN 1079-9907, pp. 60-65.

Porter, et al., "Chimeric Antigen Receptor T Cells Directed Against CD 19 Induce Durable Responses and Transient Cytokine Release Syndrome in Relapsed, Refractory CLL and ALL", Blood, (Nov. 2012), vol. 120, No. 21, p. 717. Abstract.

Ferrara, et al., "Graft-versus-host disease", Lancet, (May 2, 2009), vol. 373, No. 9674, 1550-1561.

Wagner, et al., "CAR T Cell Therapy for Solid Tumors: Bright Future or Dark Reality?", Mol Ther, (Nov. 4, 2020), vol. 28, No. 11, pp. 2320-2339.

Eshhar, et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).

Xu "Viral and Plasmid Transduction Systems: Methods to Modify Immune Cells for Cancer Immunotherapy" Diss. Thesis: Uppsala University, 2011.

Examination Report issued by the Australian Patent Office for Australian Application No. 2016298229, dated Nov. 29, 2021.

Preliminary Office Action issued by the Brazilian Patent Office for Brazilian Patent Application No. BR112018001858-9, dated Jan. 19, 2021.

Office Action issued by the China National Intellectual Property Administration for Chinese Application No. 2016800545142, dated Jan. 6, 2021.

Examination report issued by the Indian Patent Office for Indian Application No. 201817003010, dated Dec. 13, 2021.

Office Action issued by the Israel Patent Office for Israel Patent Application No. 256892, dated Dec. 8, 2020.

Notice of Reasons for Rejection issued by the Japanese Patent Office for Japanese Application No. 2018-504165, dated Jul. 19, 2021.

Office Action issued by the Federal Service for Intellectual Property for Russian Application No. 2018107047, dated Feb. 27, 2020.

Second Written Opinion issued by the Intellectual Property Office of Singapore for Singapore Patent Application No. 11201800339R, dated Jul. 20, 2020.

\* cited by examiner

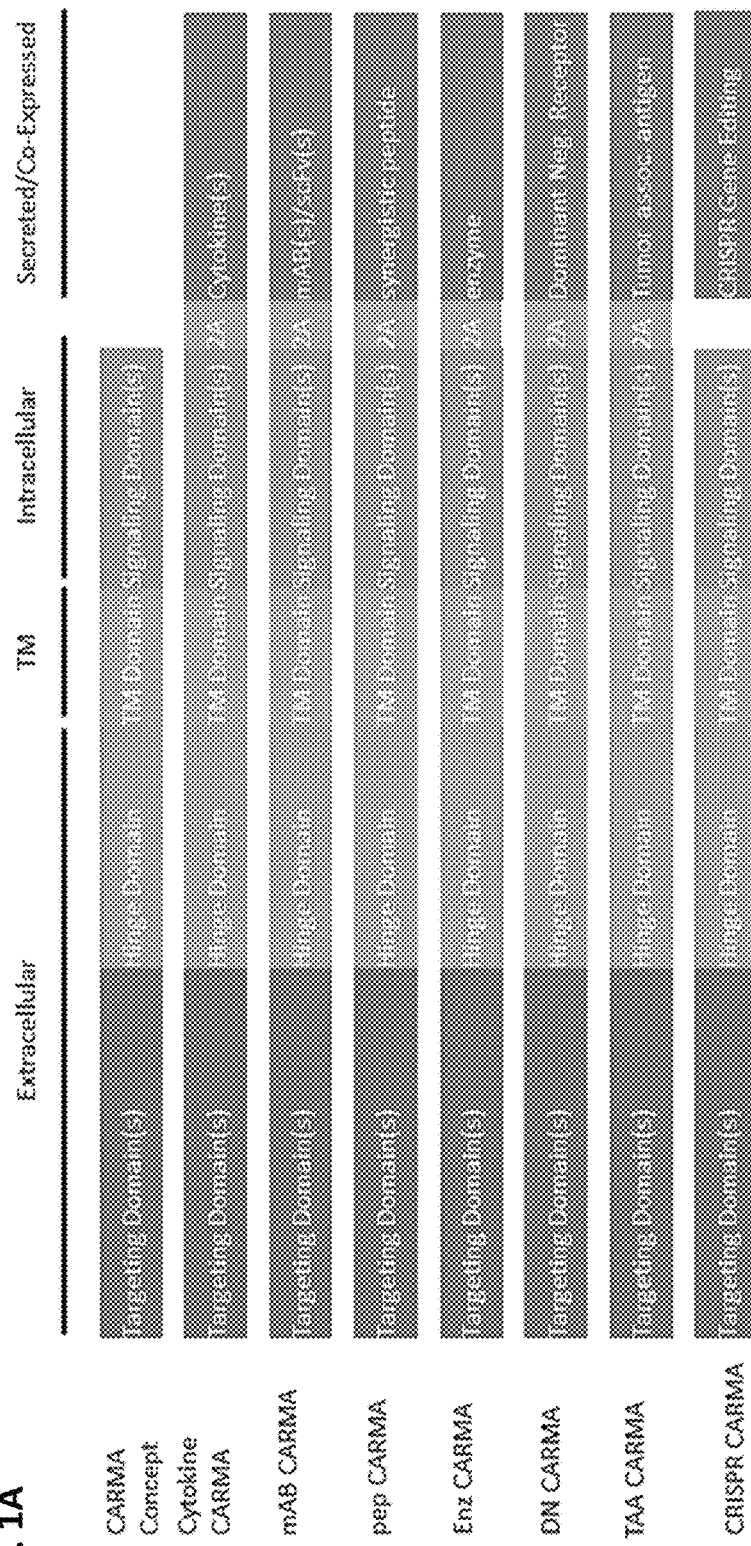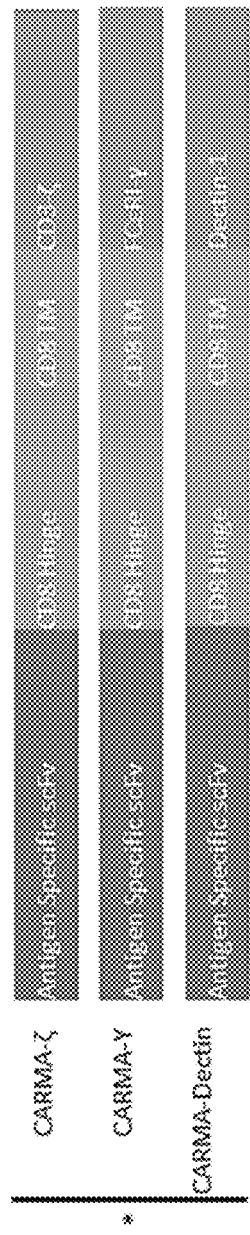

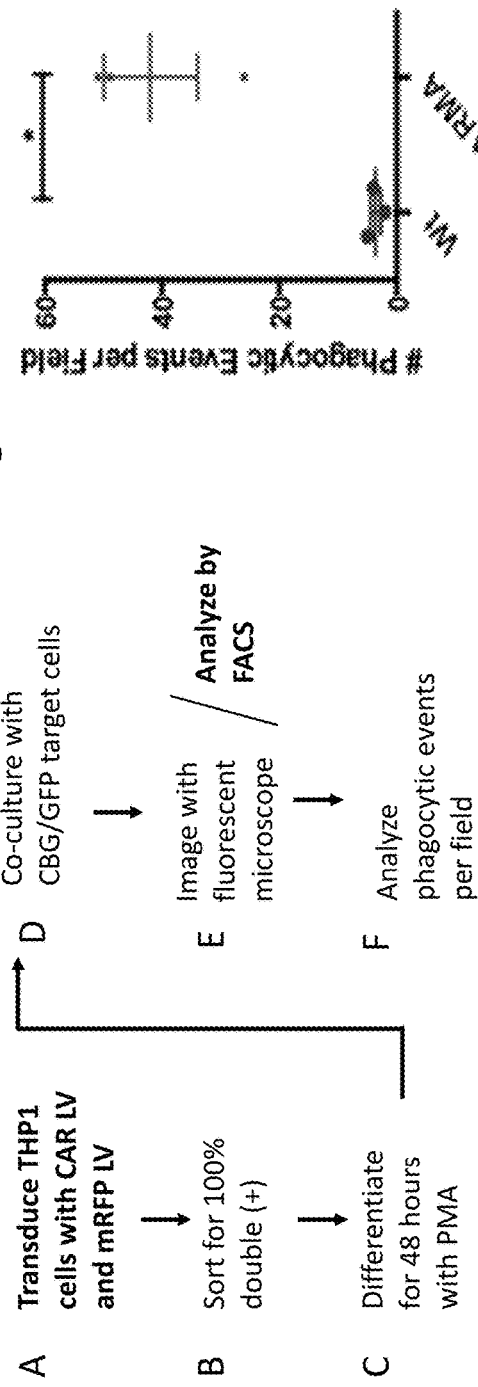
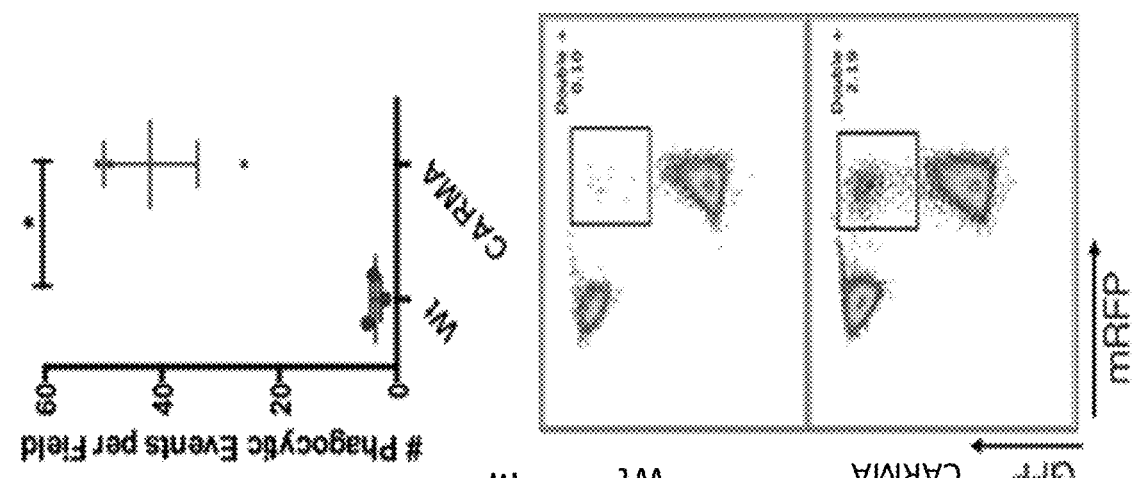
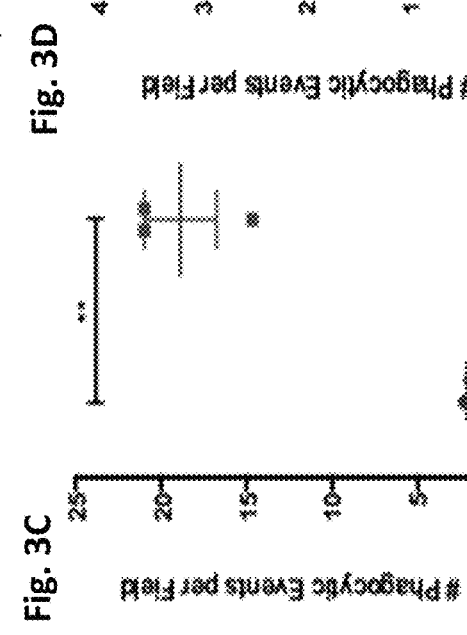
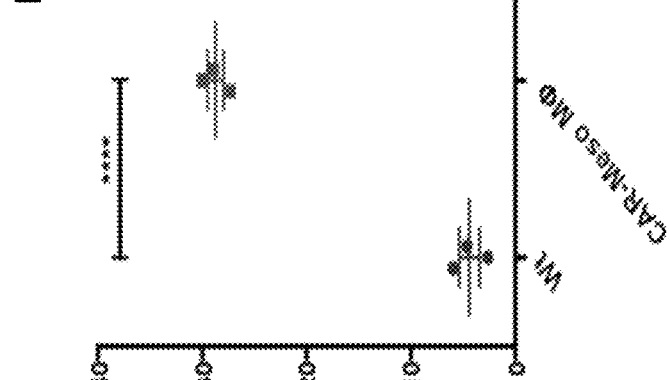
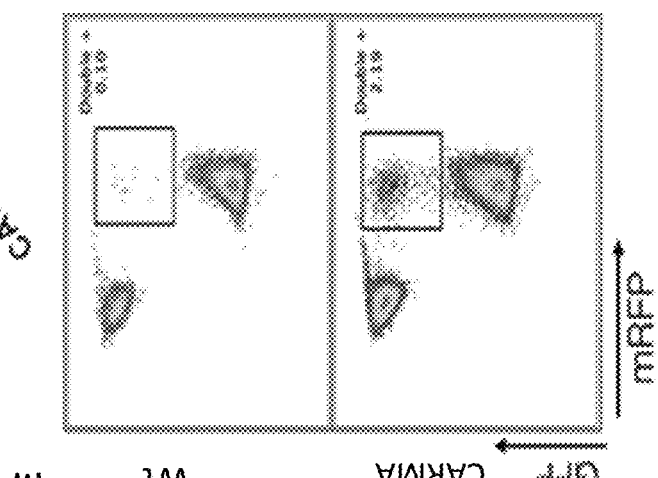

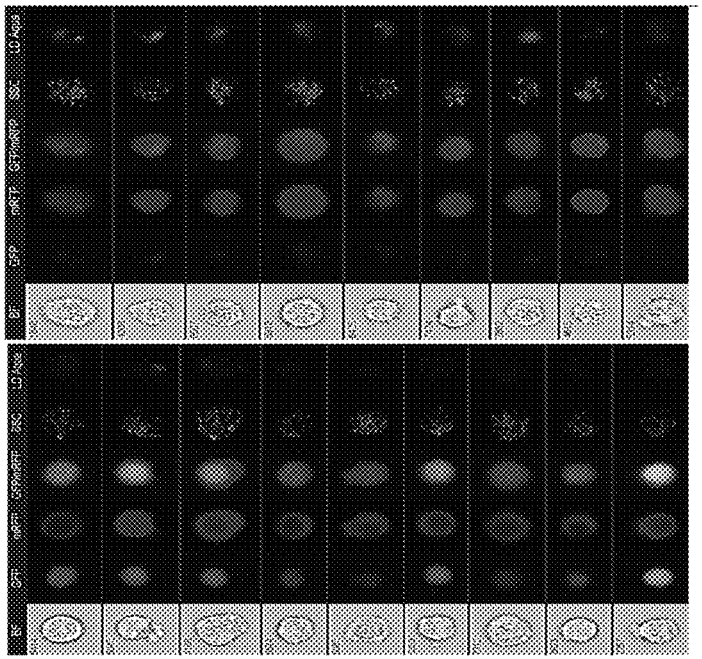
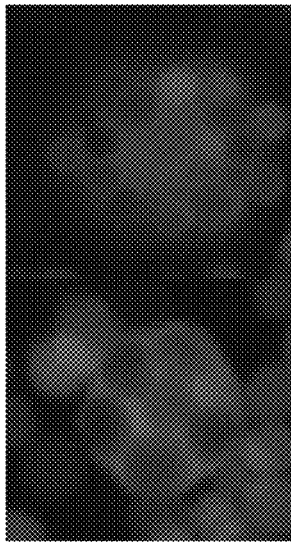
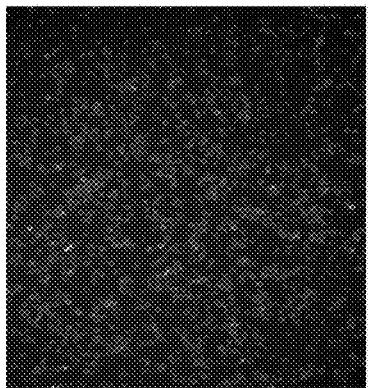
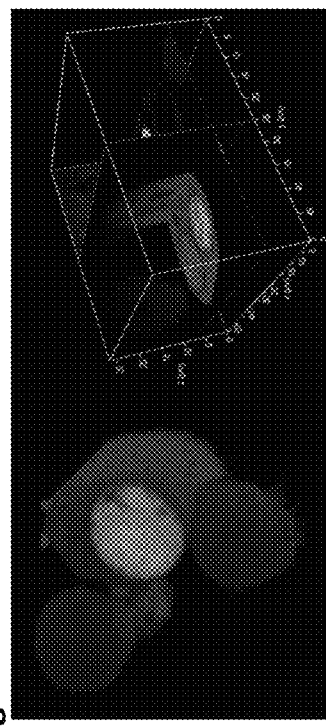
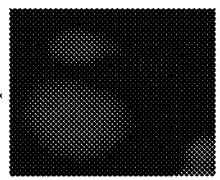
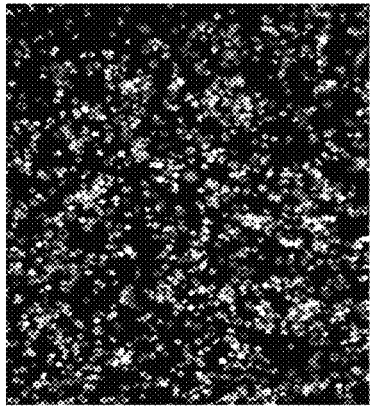

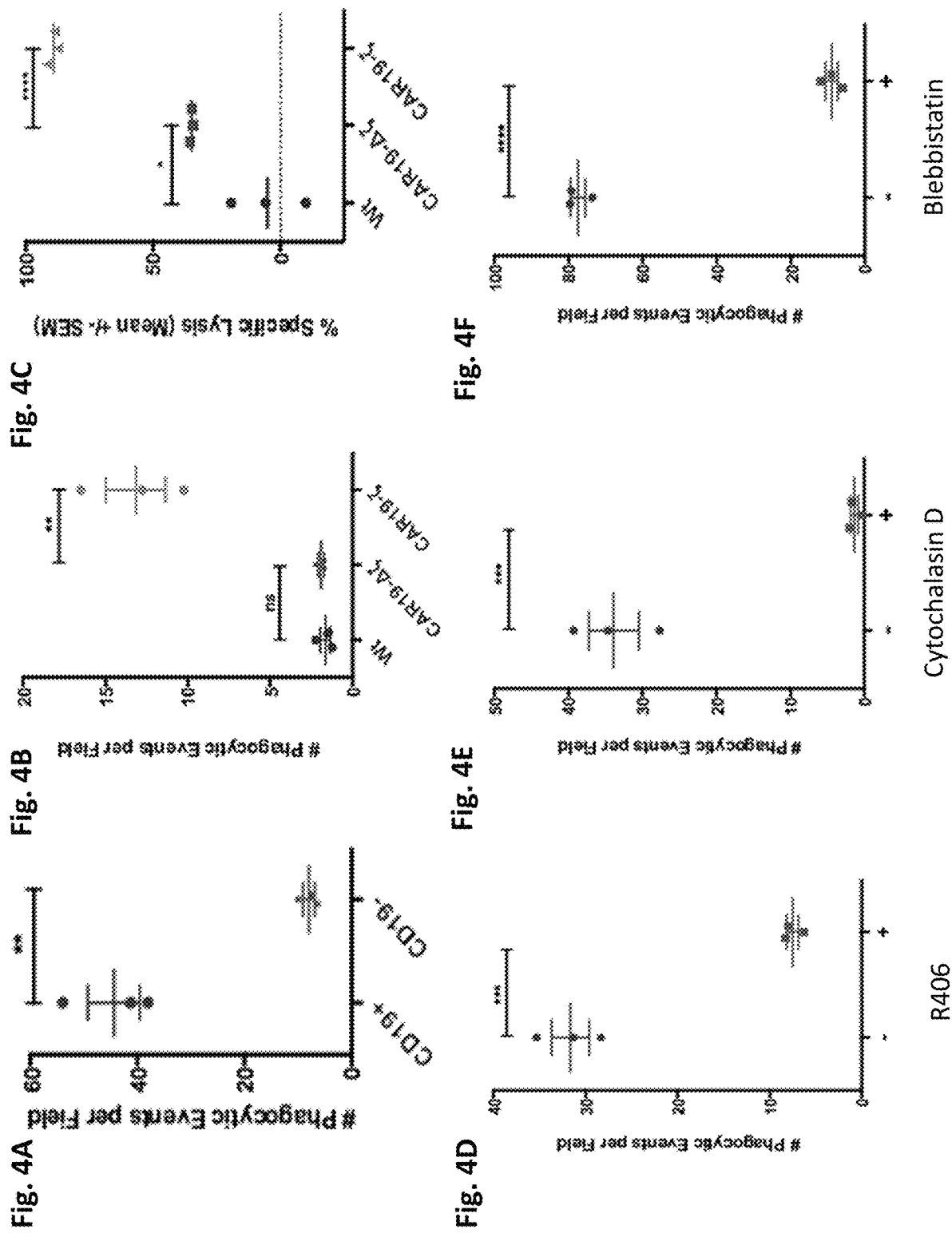

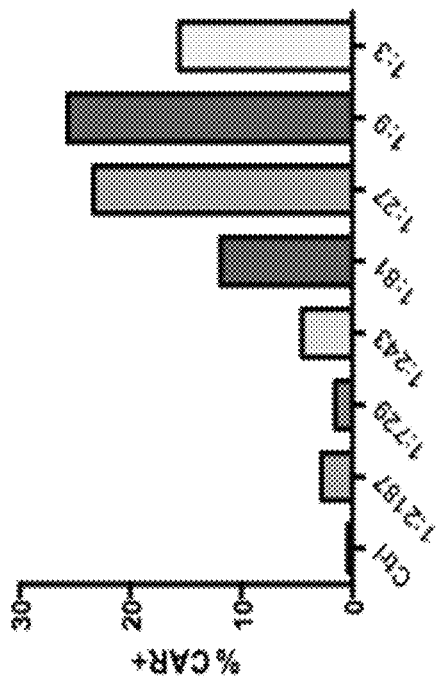
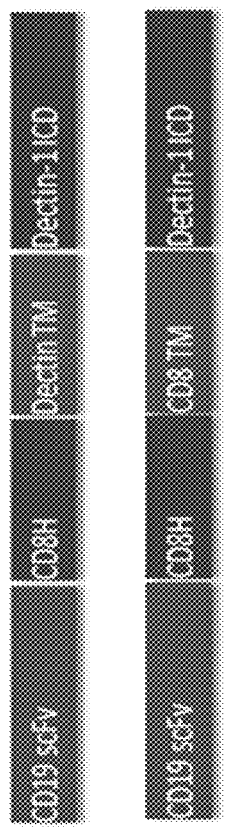
Fig. 10A
Fig. 10B
Fig. 10C
Fig. 10D

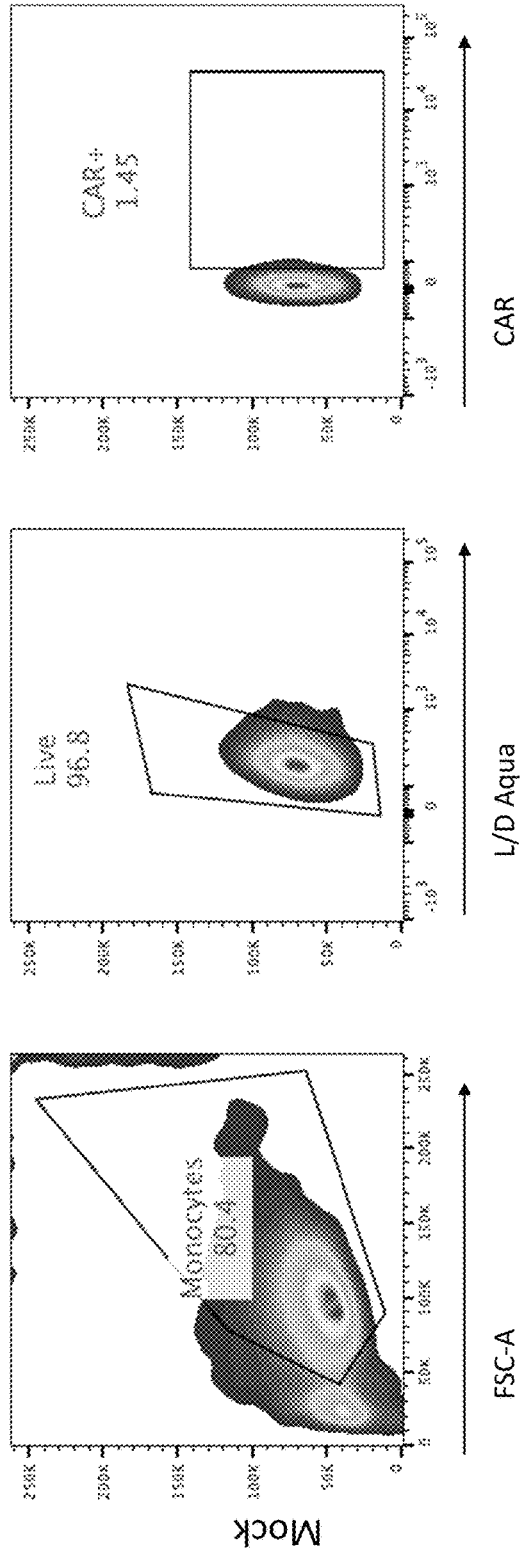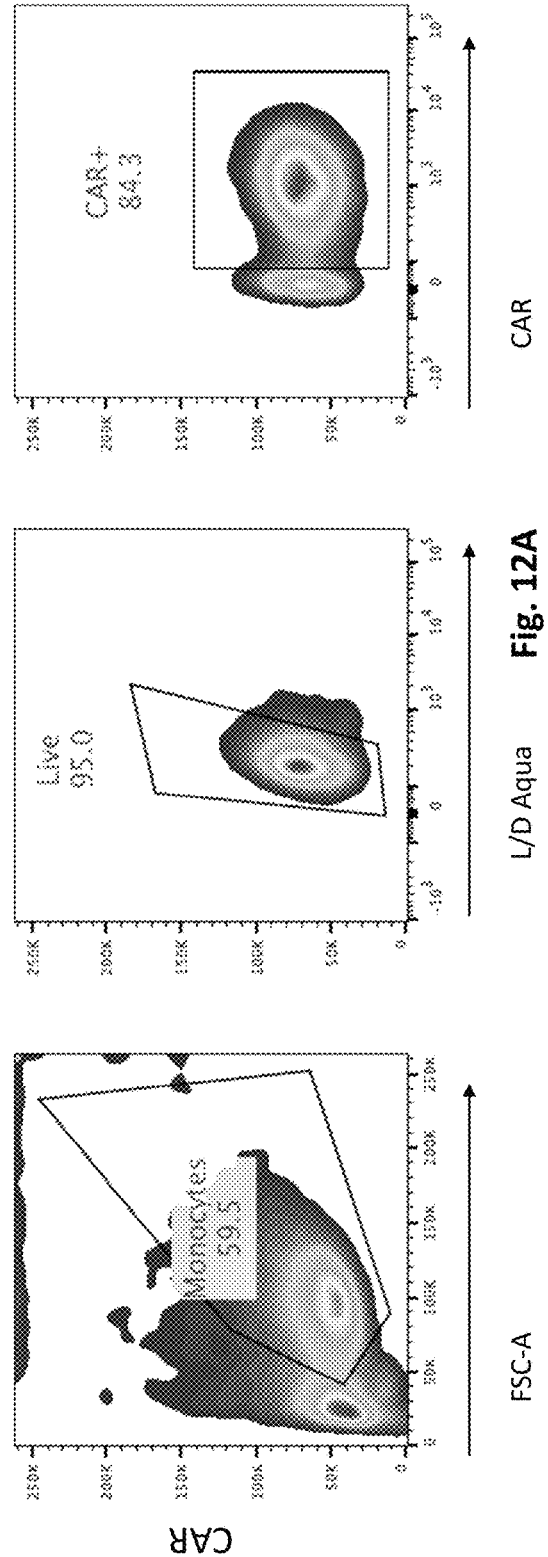
Fig. 12A

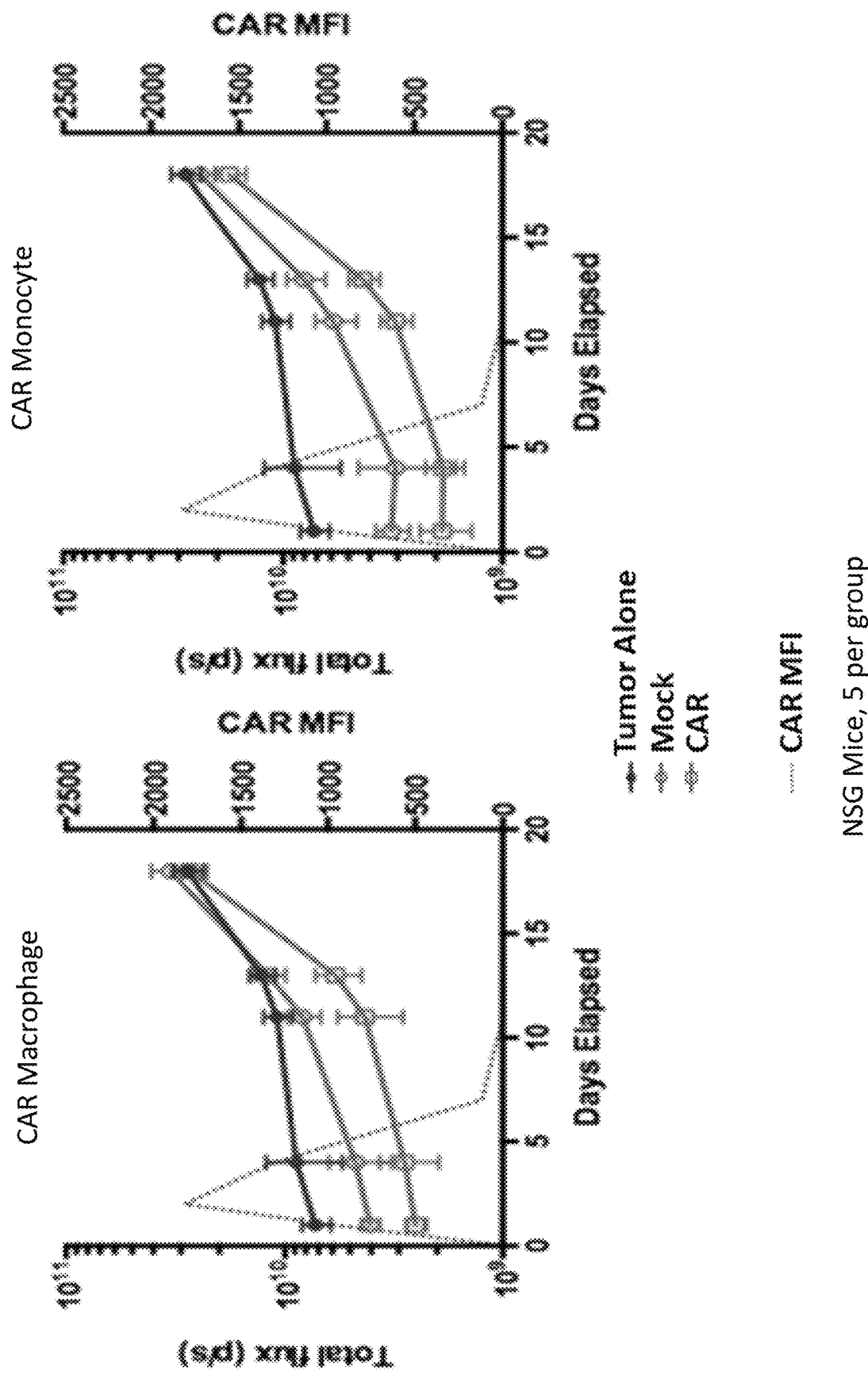

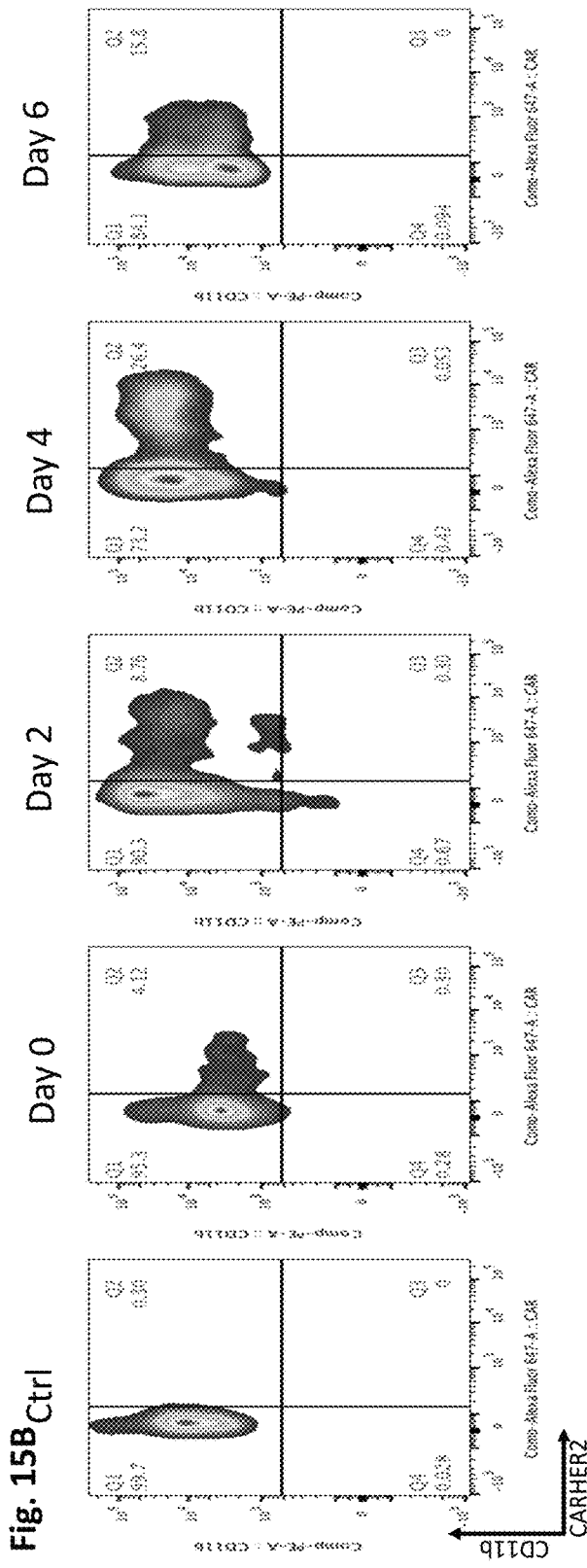
Fig. 15B
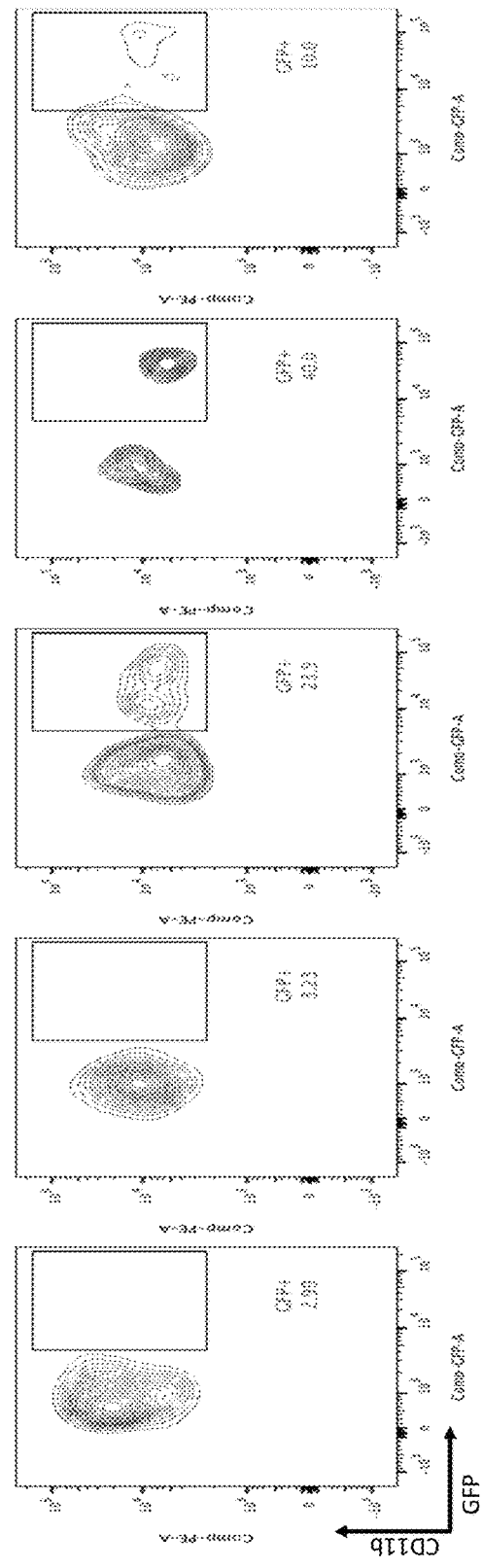
Fig. 15C Phagocytosis of K19 by primary CARMA trends with transduction efficiency

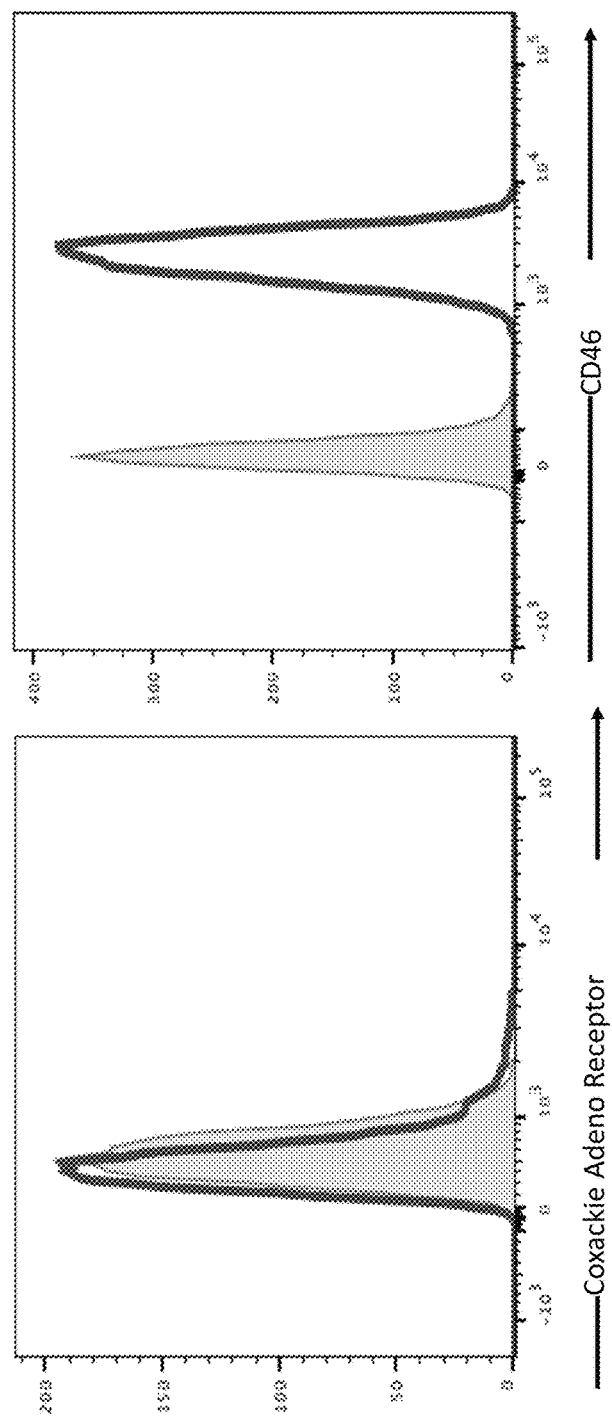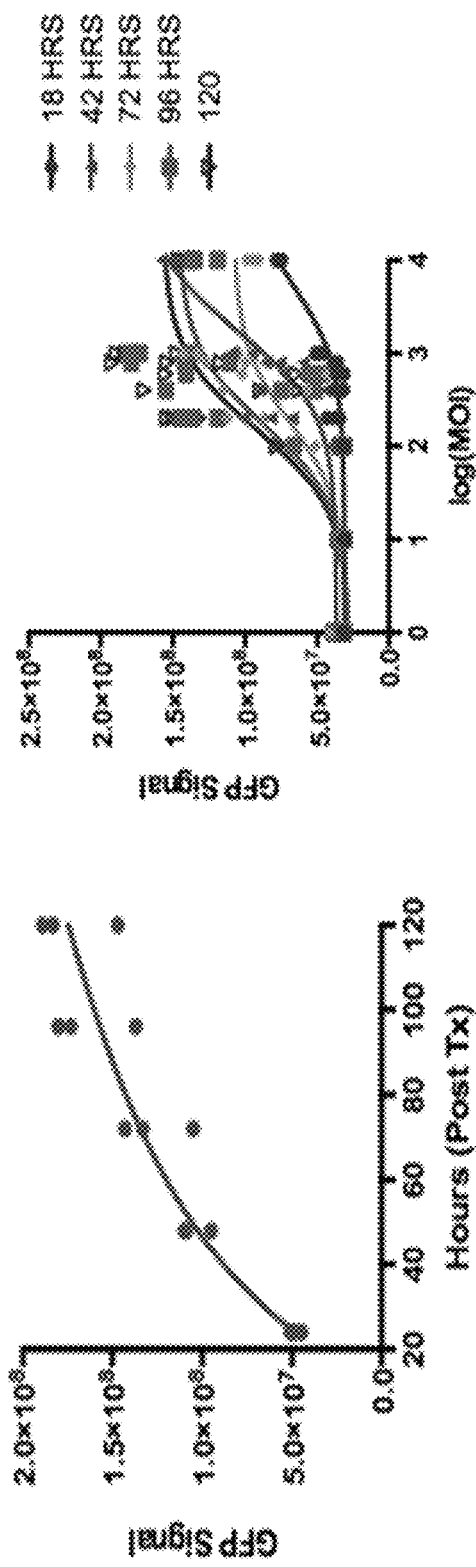
Fig. 16A
Fig. 16B
Fig. 16C

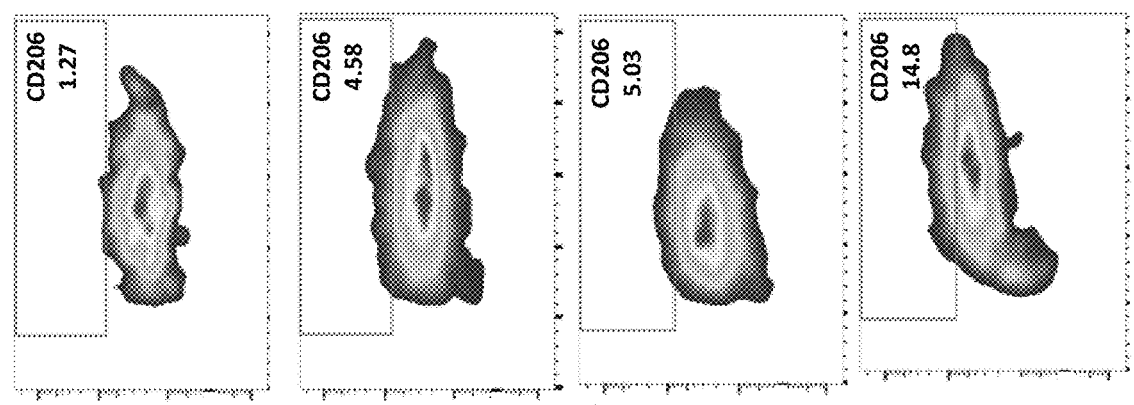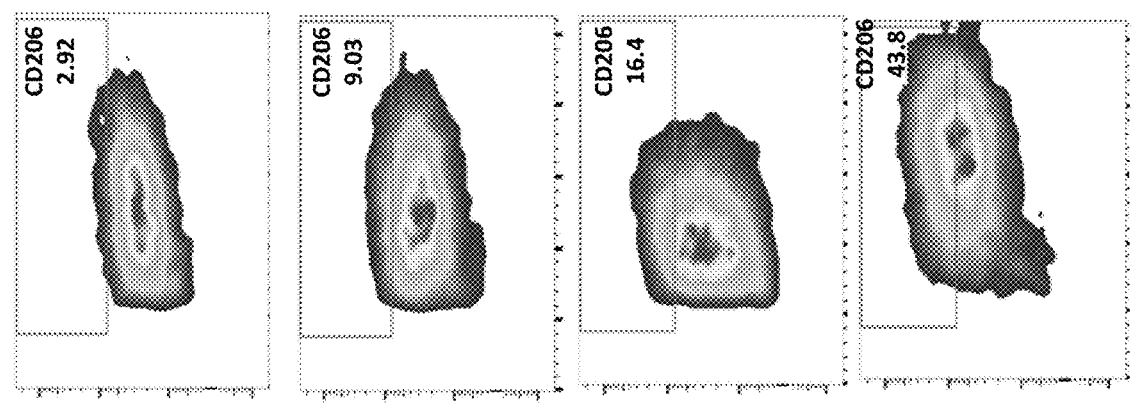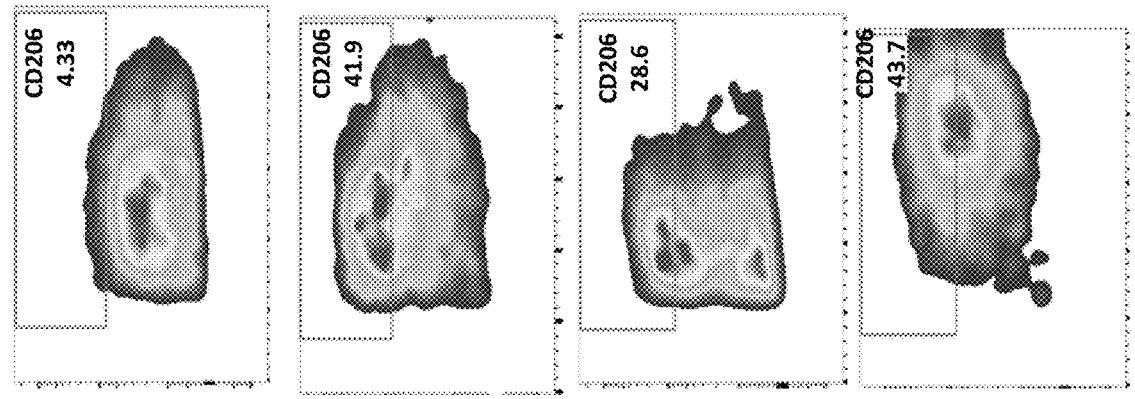
Fig. 22D

MODIFIED MONOCYTES/MACROPHAGE EXPRESSING CHIMERIC ANTIGEN RECEPTORS AND USES THEREOF

CROSS-REFERENCE TO RELATED APPLICATION

The present application is a continuation of U.S. patent application Ser. No. 16/858,183 filed Apr. 24, 2020, which is a continuation of U.S. patent application Ser. No. 15/747,555, filed Jan. 25, 2018, now U.S. Pat. No. 11,034,749, issued Jun. 15, 2021, which is a 35 U.S.C. § 371 national phase application from, and claims priority to, International Application No. PCT/US2016/044440, filed Jul. 28, 2016, and published under PCT Article 21(2) in English, which is entitled to priority under 35 U.S.C. § 119(e) to U.S. Provisional Application No. 62/197,675, filed Jul. 28, 2015, all of which are incorporated herein by reference in their entireties.

BACKGROUND OF THE INVENTION

Cancer immunotherapy has demonstrated exciting clinical results in the setting of numerous solid tumors and hematologic malignancies. The endogenous immune system is typically non-reactive to malignant cells, or can be actively immunosuppressive with respect to the body's reaction to the presence of malignant cells. One way to enhance treatment of tumors is to force tumor recognition by the immune system through genetic engineering of leukocytes. T cells can be engineered to express a synthetic immunoreceptor comprising an extracellular targeted antibody and intracellular signaling domain, known as chimeric antigen receptor (CAR). T cells expressing a CAR directed against CD19 have been shown to have profound antileukemic efficacy, where complete remission has been achieved in 90% of acute lymphoblastic leukemia patients treated (Maude, et al., NEJM, vol. 371:1507-17, 2014). These results are accompanied by robust T cell proliferation and clearly documented T cell infiltration into tumor sites in leukemic patients so treated. Despite the high response rates demonstrated in hematopoietic malignancies, CAR T cell efficacy in solid tumors (as well as in certain lymphoid tumors) may be limited. Possible explanations for this include the potentially impaired ability of T cells to infiltrate solid tumors, poor trafficking, immunosuppressive tumor microenvironment, and expression of few tumor specific antigenson solid tumor cells.

A need exists in the art for more effective compositions and methods that treat cancers by improving specificity for tumor cells and improving infiltration into tumor sites in both solid tumors and hematologic malignancies by such compositions. The present invention fulfils this need.

SUMMARY OF THE INVENTION

As disclosed herein, the present invention includes compositions and methods of using a phagocytic cell with targeted effector activity.

In one aspect, the invention includes a modified cell comprising a chimeric antigen receptor (CAR), wherein the CAR comprises an antigen binding domain, a transmembrane domain and an intracellular domain of a stimulatory and/or co-stimulatory molecule, and wherein cell is a monocyte, macrophage, or dendritic cell that possesses targeted effector activity.

In another aspect, the invention includes a modified cell comprising a nucleic acid sequence encoding a chimeric antigen receptor (CAR), wherein nucleic acid sequence comprises a nucleic acid sequence encoding an antigen binding domain, a nucleic acid sequence encoding a transmembrane domain and a nucleic acid sequence encoding an intracellular domain of a stimulatory and/or co-stimulatory molecule, and wherein the cell is a monocyte, macrophage, or dendritic cell that expresses the CAR and possesses targeted effector activity.

In yet another aspect, the invention includes a method of modifying a cell comprising introducing a chimeric antigen receptor (CAR) into the monocyte, macrophage, or dendritic cell, wherein the CAR comprises an antigen binding domain, a transmembrane domain and an intracellular domain of a stimulatory and/or co-stimulatory molecule, and wherein the cell is a monocyte, macrophage, or dendritic cell that expresses the CAR and possesses targeted effector activity.

In still another aspect, the invention includes a composition comprising the cell modified according the method described herein.

In various embodiments of the above aspects or any other aspect of the invention delineated herein, the antigen binding domain of the CAR comprises an antibody selected from the group consisting of a monoclonal antibody, a polyclonal antibody, a synthetic antibody, human antibody, humanized antibody, single domain antibody, single chain variable fragment, and antigen-binding fragments thereof. In another embodiment, the antigen binding domain of the CAR is selected from the group consisting of an anti-CD19 antibody, an anti-HER2 antibody, and a fragment thereof. In yet another embodiment, the intracellular domain of the CAR comprises dual signaling domains.

In another embodiment, the targeted effector activity is directed against an antigen on a target cell that specifically binds the antigen binding domain of the CAR. In yet another embodiment, the targeted effector activity is selected from the group consisting of phagocytosis, targeted cellular cytotoxicity, antigen presentation, and cytokine secretion.

In another embodiment, the composition further comprises an agent selected from the group consisting of a nucleic acid, an antibiotic, an anti-inflammatory agent, an antibody or antibody fragments thereof, a growth factor, a cytokine, an enzyme, a protein, a peptide, a fusion protein, a synthetic molecule, an organic molecule, a carbohydrate or the like, a lipid, a hormone, a microsome, a derivative or a variation thereof, and any combination thereof.

In another embodiment, the modified cell has at least one upregulated M1 marker and at least one downregulated M2 marker. In yet another embodiment, the modified cell is genetically modified to express the CAR. In still another embodiment, the targeted effector activity is enhanced by inhibition of CD47 or SIRPa activity.

In another embodiment, introducing the CAR into the cell comprises introducing a nucleic acid sequence encoding the CAR, such as electroporating a mRNA encoding the CAR or transducing the cell with a viral vector comprising the nucleic acid sequence encoding the CAR.

In another embodiment, the targeted effector activity is directed against an antigen on a target cell that specifically binds the antigen binding domain of the CAR. In another embodiment, the targeted effector activity is selected from the group consisting of phagocytosis, targeted cellular cytotoxicity, antigen presentation, and cytokine secretion.

In another embodiment, the method described herein further comprises inhibiting CD47 or SIRPα activity to enhance the targeted effector activity, such as by contacting the cell with a blocking anti-CD47 or a blocking anti-SIRPα antibody. In yet another embodiment, the method further comprises modifying the cell to deliver an agent to a target, wherein the agent is selected from the group consisting of a nucleic acid, an antibiotic, an anti-inflammatory agent, an antibody or antibody fragments thereof, a growth factor, a cytokine, an enzyme, a protein, a peptide, a fusion protein, a synthetic molecule, an organic molecule, a carbohydrate or the like, a lipid, a hormone, a microsome, a derivative or a variation thereof, and any combination thereof.

In one aspect, the invention includes a pharmaceutical composition comprising the cell described herein.

In another aspect, the invention includes a use of the modified cell described herein in the manufacture of a medicament for the treatment of an immune response in a subject in need thereof. In yet another aspect, the invention includes a use of the modified cell described herein in the manufacture of a medicament for the treatment of a tumor or cancer in a subject in need thereof.

In yet another aspect, the invention includes a method of treating a disease or condition associated with a tumor or cancer in a subject comprising administering to the subject a therapeutically effective amount of a pharmaceutical composition comprising the modified cell described herein.

In still another aspect, the invention includes a method of treating a tumor in a subject, comprising administering to the subject a therapeutically effective amount of a pharmaceutical composition comprising the modified cell described herein.

In another aspect, the invention includes a method for stimulating an immune response to a target tumor cell or tumor tissue in a subject comprising administering to a subject a therapeutically effective amount of a pharmaceutical composition comprising the modified cell described herein.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A is a series of images showing the conceptual diagram of a chimeric antigen receptor (CAR) comprised of a gene/gene-product containing an extracellular domain with targeting function, a hinge domain, a transmembrane domain, an intracellular signaling domain(s), and/or a 2A (P2A, T2A) for stoichiometric co-expression of an additional gene product which may or may not be secreted, including any gene/transcript/protein, including but not limited to a cytokine, monoclonal antibody, antibody fragment, single chain variable fragment, enzyme, additional receptor, dominant negative receptor, tumor associated antigen(s), and any combination thereof. In addition, the CAR construct may include co-delivery of CRISPR/Cas9 gene editing material, or be introduced in the context of a CRISPR/Cas9 pre-edited cell.

FIG. 1B is a series of images showing specific examples of CAR constructs, including CARMA-ζ, CARMA-γ, and CARMA-Dectin, which contain an antigen specific scFv, CD8 hinge, CD8 transmembrane, and a CD3 ζ, FcεRI common γ subunit, or the intracellular domain of Dectin-1, respectively.

FIG. 3A is a flow chart showing the overview of CARMA subline generation using a THP1 macrophage model, differentiation with 1 ng/mL phorbol 12-myristate 13-acetate (PMA), and in vitro phagocytosis assay.

FIG. 3B is a graph showing anti-CD19 CAR macrophages, but not wild type (Wt) macrophages, phagocytosed K562 tumor cells that expressed CD19, as demonstrated by fluorescent microscopy based phagocytosis assays.

FIG. 3C is a graph showing anti-HER2 CAR macrophages, but not wild type (Wt) macrophages, phagocytosed K562 tumor cells that expressed HER2, as demonstrated by fluorescent microscopy based phagocytosis assays.

FIG. 3D is a graph showing anti-mesothelin CAR macrophages, but not wild type (Wt) macrophages, phagocytosed K562 tumor cells that expressed mesothelin, as demonstrated by fluorescent microscopy based phagocytosis assays.

FIG. 3E is a representative FACS plot showing CARMA tumor phagocytosis was validated by a flow cytometric based assay, in which mRFP+CARMA against CD19 were co-cultured with CD19+ GFP+K562 cells and double positive events were quantified.

FIG. 3F is an image showing mRFP in a standard 10× field of view used in the tabulation of CARMA phagocytosis function.

FIG. 3G is an image showing an overlay in a standard 10× field of view used in the tabulation of CARMA phagocytosis function.

FIG. 3H is a series of images showing FACS based mRFP/GFP double positive events were defined as phagocytic events, and were validated as such by Amnis Imagestream FACS analysis. Events shown are gated on double positive events and ordered from high to low by the Amnis Imagestream phagocytosis-erode algorithm.

FIG. 3I is a series of images showing phagocytosis of tumor cells by mRFP+CARMA in the THP-1 cell line model was further demonstrated by confocal microscopy, verifying that GFP+ tumor cells have been completely enclosed within phagosomes via three-dimensional confocal z-stack reconstructions.

FIG. 3J is a series of images showing phagocytosis of tumor cells by mRFP+CARMA in the THP-1 cell line model was further demonstrated by confocal microscopy, verifying that GFP+ tumor cells have been completely enclosed within phagosomes via three-dimensional confocal z-stack reconstructions.

FIG. 3K is a series of images that demonstrate the fate of a single CARMA cell over time—with contact and immunological synapse formation being the first step, leading to phagocytic engulfment, degradation of tumor using loss of GFP as a marker of cell death, phagosome breakdown, and phagosome repair—demonstrating that CARMA survive post tumor cell phagocytosis.

FIG. 4A is a graph showing anti-CD19 CAR macrophages tested using in an in vitro phagocytosis assay against CD19+ (target) or CD19− (control) GFP+K562 tumor cells. Demonstrating the antigen specificity of CARMA, only antigen-bearing tumor cells were phagocytosed. To demonstrate the requirement for the intracellular signaling domain in CARMA function, CAR19-Δζ constructs (which lack an intracellular signaling domain) were utilized.

FIG. 4B is a graph showing CAR19-Δζ macrophages failed to phagocytose tumor cells.

FIG. 4C is a graph showing the CAR19-Δζ macrophages had significantly reduced anti-tumor function via an in vitro luciferase based specific lysis assay.

FIG. 4D is a graph showing in vitro CARMA phagocytosis assay performed in the presence of R406 (Syk inhibitor). R406 independently abrogated the phagocytic function of CARMA, indicating that CAR signaling in macrophages is Syk dependent and results in actin polymerization and NMIIA mediated phagocytic function.

FIG. 4E is a graph showing in vitro CARMA phagocytosis assay performed in the presence of cytochalasin D (actin polymerization inhibitor). Cytochalasin D independently abrogated the phagocytic function of CARMA, indicating that CAR signaling in macrophages is Syk dependent and results in actin polymerization and NMIIA mediated phagocytic function.

FIG. 4F is a graph showing in vitro CARMA phagocytosis assay performed in the presence blebbistatin (non-muscle myosin IIA inhibitor). Blebbistatin independently abrogated the phagocytic function of CARMA, indicating that CAR signaling in macrophages is Syk dependent and results in actin polymerization and NMIIA mediated phagocytic function.

FIG. 10A is a series of images showing CAR constructs comprised of a Dectin-1 intracellular signaling domain were generated. These constructs were packaged into lentivirus and used to transduce THP-1 myeloid cells in a three-fold serial dilution of lentiviral titers.

FIG. 10B is a graph showing that CAR was detected on the surface of macrophage expressing CD8TM-Dectin1 CAR constructs.

FIG. 10C is a graph showing that CAR was detected on the surface of macrophage expressing DectinTM-Dectin1 CAR constructs.

FIG. 10D is a graph showing CD8TM-Dectin1 CAR and DectinTM-Dectin1 CAR macrophages were tested in an in vitro luciferase killing assay. Both constructs demonstrated specific lysis of tumor cells.

FIG. 12A is a series of graphs showing anti-HER2 CAR constructs cloned into mRNA expression plasmids, transcribed in vitro, and the mRNA directly electroporated into primary human monocytes.

FIG. 13A is a graph showing NSGS mice injected with 1E6 SKOV3 CBG/GFP+ human ovarian cancer cells via IP injection, a model of metastatic intraperitoneal carcinomatosis of HER2+ ovarian cancer. Mice were co-injected with either mock electroporated or anti-HER2 CAR mRNA electroporated primary human macrophages (1:1 E:T ratio) and tumor burden was imaged. CAR macrophages demonstrated marginal reduction in tumor growth over approximately two weeks. The first time point at which tumor burden was bioluminescently quantified was 24 hours post-treatment, demonstrating that CAR monocytes and macrophages had activity in the first 24 hours.

FIG. 13B is a graph showing NSGS mice injected with 1E6 SKOV3 CBG/GFP+ human ovarian cancer cells via IP injection, a model of metastatic intraperitoneal carcinomatosis of HER2+ ovarian cancer. Mice were co-injected with either mock electroporated or anti-HER2 CAR mRNA electroporated primary human monocytes (1:1 E:T ratio) and tumor burden was imaged. CAR monocytes demonstrated marginal reduction in tumor growth over approximately two weeks. The first time point at which tumor burden was bioluminescently quantified was 24 hours post-treatment, demonstrating that CAR monocytes and macrophages had activity in the first 24 hours.

FIG. 15B is a series of graphs showing transduction efficiency peaked at the midpoint of transduction (day 4), for anti-HER2. Monocyte derived macrophages were generated by differentiating CD14+ selected cells (from normal donor apheresis products) in GM-CSF conditioned media for 7 days. To optimize delivery of CAR via lentiviral transduction, anti-HER2 lentivirus was used to transduce macrophages at different points of the monocyte to macrophage differentiation process.

FIG. 15C is a series of graphs showing that the efficacy of phagocytosis trended with the CAR transduction efficiency, peaking with macrophages transduced at day 4 during the differentiation process.

FIG. 16A is a series of graphs showing alternative transduction approaches to delivering transgenes to primary human macrophages were tested, given that mRNA electroporation was transient and lentivirus was only moderately efficient and required high titer. Adenovirus (recombinant, replication deficient) was identified as an efficient approach to primary human macrophage transduction. Expression of Coxackie Adenovirus Receptor (the docking protein for Ad5) and CD46 (the docking protein for Ad35) were tested relative to isotype control on primary human macrophages, and CD46 but not Coxackie Adenovirus receptor was highly expressed. Thus, chimeric Ad5f35 adenovirus was utilized for primary human macrophage transduction, and was engineered via standard molecular biology techniques to express a chimeric antigen receptor (GFP and empty Ad5f35 viruses were used as controls) against HER2.

FIG. 16B is a graph showing that at an MOI of 1000, Ad5f35 effectively delivered a transgene (GFP was used as a model transgene) into human macrophages, and expression went up over time as monitored by GFP signal quantification on an IVIS Spectrum.

FIG. 16C is a graph showing the comparison of the transduction kinetics of primary human macrophages at different timepoints across a broad range of MOIs—up to 10,000.

FIG. 22D is a panel of graphs showing the resistance to immunosuppression of human CAR macrophages, control UTD, Empty Ad5f35, or anti-HER2 CAR Ad5f35 transduced macrophages exposed to 10 ng/mL of IL-4, a canonical M2 inducing cytokine, or cancer cells that were previously shown to subvert macrophages to M2 during co-culture (SKOV3, ovarian cancer cell line; HDLM2, Hodgkin lymphoma cell line). Control UTD macrophages upregulated CD206, an M2 marker that specifically responds to IL-4 stimulation via STAT6 phosphorylation. Empty Ad5f35, and more so CAR-Ad5f35 transduced macrophages, displayed resistance to IL-4 and tumor induced subversion to the M2 phenotype.

DETAILED DESCRIPTION

Definitions

Figure 2B:
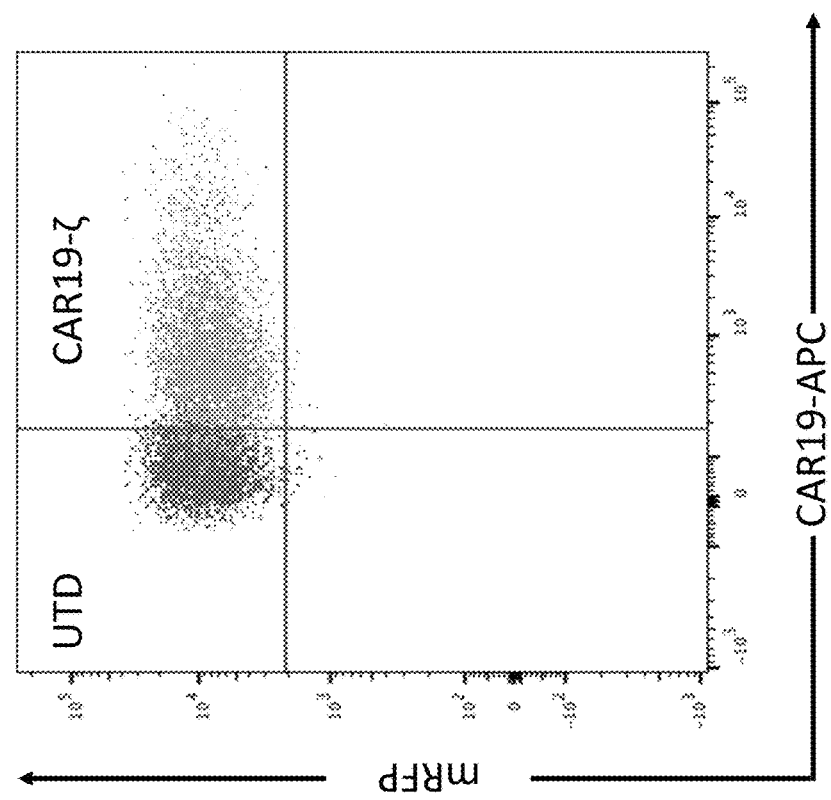
FIG. 2B is a graph showing transduced THP1 cells expanded and sorted by FACS to generate a 100% CAR19z positive mRFP+THP1 subline.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a monocyte/macrophage that has been sufficiently stimulated to induce detectable cellular proliferation or has been stimulated to exert its effector function. Activation can also be associated with induced cytokine production, phagocytosis, cell signaling, target cell killing, or antigen processing and presentation. The term "activated monocytes/macrophages" refers to, among other things, monocyte/macrophage that are undergoing cell division or exerting effector function.

The term "agent," or "biological agent" or "therapeutic agent" as used herein, refers to a molecule that may be expressed, released, secreted or delivered to a target by the modified cell described herein. The agent includes, but is not limited to, a nucleic acid, an antibiotic, an anti-inflammatory agent, an antibody or antibody fragments thereof, a growth factor, a cytokine, an enzyme, a protein, a peptide, a fusion protein, a synthetic molecule, an organic molecule (e.g., a small molecule), a carbohydrate or the like, a lipid, a hormone, a microsome, a derivative or a variation thereof, and any combination thereof. The agent may bind any cell moiety, such as a receptor, an antigenic determinant, or other binding site present on a target or target cell. The agent may diffuse or be transported into the cell, where it may act intracellularly.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is medullary thyroid carcinoma.

The term "chimeric antigen receptor" or "CAR," as used herein, refers to an artificial T cell surface receptor that is engineered to be expressed on an immune effector cell and specifically bind an antigen. CARs may be used as a therapy with adoptive cell transfer. Monocytes are removed from a patient (blood, tumor or ascites fluid) and modified so that they express the receptors specific to a particular form of antigen. In some embodiments, the CARs have been expressed with specificity to a tumor associated antigen, for example. CARs may also comprise an intracellular activation domain, a transmembrane domain and an extracellular domain comprising a tumor associated antigen binding region. In some aspects, CARs comprise fusions of single-chain variable fragments (scFv) derived monoclonal antibodies, fused to CD3-zeta transmembrane and intracellular domain. The specificity of CAR designs may be derived from ligands of receptors (e.g., peptides). In some embodiments, a CAR can target cancers by redirecting a monocyte/macrophage expressing the CAR specific for tumor associated antigens.

The term "chimeric intracellular signaling molecule" refers to recombinant receptor comprising one or more intracellular domains of one or more stimulatory and/or co-stimulatory molecules. The chimeric intracellular signaling molecule substantially lacks an extracellular domain. In some embodiments, the chimeric intracellular signaling molecule comprises additional domains, such as a transmembrane domain, a detectable tag, and a spacer domain.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a monocyte/macrophage, thereby providing a signal which mediates a monocyte/macrophage response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a monocyte/macrophage, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to a molecule on an innate immune cell that is used to heighten or dampen the initial stimulus. For example, pathogen-associated pattern recognition receptors, such as TLR (heighten) or the CD47/SIRPα axis (dampen), are molecules on innate immune cells. Co-stimulatory molecules include, but are not limited to TCR, CD3 zeta, CD3 gamma, CD3 delta, CD3 epsilon, CD86, common FcR gamma, FcR beta (Fc Epsilon R1b), CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof.

A "co-stimulatory signal", as used herein, refers to a signal, which in combination with a primary signal, such as activation of the CAR on a macrophage, leads to activation of the macrophage.

The term "cytotoxic" or "cytotoxicity" refers to killing or damaging cells. In one embodiment, cytotoxicity of the metabolically enhanced cells is improved, e.g. increased cytolytic activity of macrophages.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of monocytes/macrophages. In one embodiment, the monocytes/macrophages that are expanded ex vivo increase in number relative to the number originally present in the culture. In another embodiment, the monocytes/macrophages that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. As applied to the nucleic acid or protein, "homologous" as used herein refers to a sequence that has about 50% sequence identity. More preferably, the homologous sequence has about 75% sequence identity, even more preferably, has at least about 80%, 85%, 90%, 91%, 92%, 93%, 94%, 95%, 96%, 97%, 98%, 99% sequence identity.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

The guide nucleic acid sequence may be complementary to one strand (nucleotide sequence) of a double stranded DNA target site. The percentage of complementation between the guide nucleic acid sequence and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The guide nucleic acid sequence can be at least 10, 11, 12, 13, 14, 15, 16, 17, 18, 19, 20, 21, 22, 23, 24, 25, 26, 27, 28, 29, 30, 31, 32, 33, 34, 35 or more nucleotides in length. In some embodiments, the guide nucleic acid sequence comprises a contiguous stretch of 10 to 40 nucleotides. The variable targeting domain can be composed of a DNA sequence, a RNA sequence, a modified DNA sequence, a modified RNA sequence (see for example modifications described herein), or any combination thereof.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), intratumoral (i.t.) or intra-peritoneal (i.p.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "resistance to immunosuppression" refers to lack of suppression or reduced suppression of an immune system activity or activation.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the Fc receptor machinery or via the synthetic CAR. Stimulation can mediate altered expression of certain molecules, such as downregulation of TGF-beta, and/or reorganization of cytoskeletal structures, and the like.

A "stimulatory molecule," as the term is used herein, means a molecule on a monocyte/macrophage that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) or tumor cell can specifically bind with a cognate binding partner (referred to herein as a "stimulatory molecule") on a monocyte/macrophage, thereby mediating a response by the immune cell, including, but not limited to, activation, initiation of an immune response, proliferation, and the like. Stimulatory ligands are well-known in the art and encompass, inter alia, Toll-like receptor (TLR) ligand, an anti-toll-like receptor antibody, an agonist, and an antibody for a monocyte/macrophage receptor. In addition, cytokines, such as interferon-gamma, are potent stimulants of macrophages.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

By "target" is meant a cell, organ, or site within the body that is in need of treatment.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The term "tumor" as used herein, refers to an abnormal growth of tissue that may be benign, pre-cancerous, malignant, or metastatic.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Accumulating evidence suggests that macrophages are abundant in the tumor microenvironment of numerous cancers where they can adopt a classically activated (M1, antitumor) or an alternatively activated (M2, pro-tumor) phenotype. Macrophages are potent effectors of the innate immune system and are capable of at least three distinct anti-tumor functions: phagocytosis, cellular cytotoxicity, and antigen presentation to orchestrate an adaptive immune response. While T cells require antigen-dependent activation via the T cell receptor or the chimeric immunoreceptor, macrophages can be activated in a variety of ways. Direct macrophage activation is antigen-independent, relying on mechanisms such as pathogen associated molecular pattern recognition by Toll-like receptors (TLRs). Immune-complex mediated activation is antigen dependent but requires the presence of antigen-specific antibodies and absence of the inhibitory CD47-SIRPα interaction.

Tumor-associated macrophages have been shown to be re-programmable by the tumor microenvironment to become key immunosuppressive players in the microenvironment. Therefore, the ability to genetically engineer macrophages to prevent the development of an immunosuppressive genetic reprogram would represent a vertical advance in the field.

The present invention includes compositions and methods for treating a malignancy in a subject. The invention includes expression of a chimeric antigen receptor in a monocyte, macrophage or dendritic cell. Such a modified cell is recruited to the tumor microenvironment where it acts as a potent immune effector by infiltrating the tumor and killing target cells.

Chimeric Antigen Receptor (CAR)

In one aspect of the invention, a modified monocyte, macrophage, or dendritic cell is generated by expressing a CAR therein. Thus, the present invention encompasses a CAR and a nucleic acid construct encoding a CAR, wherein the CAR includes an antigen binding domain, a transmembrane domain and an intracellular domain.

In one aspect, the invention includes a modified cell comprising a chimeric antigen receptor (CAR), wherein the CAR comprises an antigen binding domain, a transmembrane domain and an intracellular domain of a co-stimulatory molecule, and wherein cell is a monocyte, macrophage, or dendritic cell that possesses targeted effector activity. In another aspect, the invention includes a modified cell comprising a nucleic acid sequence encoding a chimeric antigen receptor (CAR), wherein nucleic acid sequence comprises a nucleic acid sequence encoding an antigen binding domain, a nucleic acid sequence encoding a transmembrane domain and a nucleic acid sequence encoding an intracellular domain of a co-stimulatory molecule, and wherein the cell is a monocyte, macrophage, or dendritic cell that expresses the CAR and possesses targeted effector activity. In one embodiment, the targeted effector activity is directed against an antigen on a target cell that specifically binds the antigen binding domain of the CAR. In another embodiment, the targeted effector activity is selected from the group consisting of phagocytosis, targeted cellular cytotoxicity, antigen presentation, and cytokine secretion.

Antigen Binding Domain

In one embodiment, the CAR of the invention comprises an antigen binding domain that binds to an antigen on a target cell. Examples of cell surface markers that may act as an antigen that binds to the antigen binding domain of the CAR include those associated with viral, bacterial and parasitic infections, autoimmune disease, and cancer cells.

The choice of antigen binding domain depends upon the type and number of antigens that are present on the surface of a target cell. For example, the antigen binding domain may be chosen to recognize an antigen that acts as a cell surface marker on a target cell associated with a particular disease state.

In one embodiment, the antigen binding domain binds to a tumor antigen, such as an antigen that is specific for a tumor or cancer of interest. In one embodiment, the tumor antigen of the present invention comprises one or more antigenic cancer epitopes.

Nonlimiting examples of tumor associated antigens include CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4)bDGicp(1-1)Cer); transglutaminase 5 (TGSS); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WTi); Cancer/testis antigen 1 (NY-ESO-1); Cancer/testis antigen 2 (LAGE-la); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. Thus, in one embodiment, the antigen binding domain portion comprises a mammalian antibody or a fragment thereof. In another embodiment, the antigen binding domain of the CAR is selected from the group consisting of an anti-CD19 antibody, an anti-HER2 antibody, and a fragment thereof.

In some instances, the antigen binding domain is derived from the same species in which the CAR will ultimately be used in. For example, for use in humans, it the antigen binding domain of the CAR comprises a human antibody, a humanized antibody, or a fragment thereof.

In some aspects of the invention, the antigen binding domain is operably linked to another domain of the CAR, such as the transmembrane domain or the intracellular domain, for expression in the cell. In one embodiment, a nucleic acid encoding the antigen binding domain is operably linked to a nucleic acid encoding a transmembrane domain and a nucleic acid encoding an intracellular domain.

Transmembrane Domain

With respect to the transmembrane domain, the CAR can be designed to comprise a transmembrane domain that connects the antigen binding domain of the CAR to the intracellular domain. In one embodiment, the transmembrane domain is naturally associated with one or more of the domains in the CAR. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, Toll-like receptor 1 (TLR1), TLR2, TLR3, TLR4, TLR5, TLR6, TLR7, TLR8, and TLR9. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

Intracellular Domain

The intracellular domain or otherwise, the cytoplasmic domain of the CAR, includes a similar or the same intracellular domain as the chimeric intracellular signaling molecule described elsewhere herein, and is responsible for activation of the cell in which the CAR is expressed.

In one embodiment, the intracellular domain of the CAR includes a domain responsible for signal activation and/or transduction.

Examples of an intracellular domain for use in the invention include, but are not limited to, the cytoplasmic portion of a surface receptor, co-stimulatory molecule, and any molecule that acts in concert to initiate signal transduction in the monocyte, macrophage or dendritic cell, as well as any derivative or variant of these elements and any synthetic sequence that has the same functional capability.

Examples of the intracellular domain include a fragment or domain from one or more molecules or receptors including, but are not limited to, TCR, CD3 zeta, CD3 gamma, CD3 delta, CD3 epsilon, CD86, common FcR gamma, FcR beta (Fc Epsilon R1b), CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

In one embodiment, the intracellular domain of the CAR comprises dual signaling domains, such as 41BB, CD28, ICOS, TLR1, TLR2, TLR3, TLR4, TLR5, TLR6, TLR7, TLR8, TLR9, TLR10, TLR11, CD116 receptor beta chain, CSF1-R, LRP1/CD91, SR-A1, SR-A2, MARCO, SR-CL1, SR-CL2, SR-C, SR-E, CR1, CR3, CR4, dectin 1, DEC-205, DC-SIGN, CD14, CD36, LOX-1, CD11b, together with any of the signaling domains listed in the above paragraph in any combination. In another embodiment, the intracellular domain of the CAR includes any portion of one or more co-stimulatory molecules, such as at least one signaling domain from CD3, Fc epsilon RI gamma chain, any derivative or variant thereof, any synthetic sequence thereof that has the same functional capability, and any combination thereof.

Between the antigen binding domain and the transmembrane domain of the CAR, or between the intracellular domain and the transmembrane domain of the CAR, a spacer domain may be incorporated. As used herein, the term "spacer domain" generally means any oligo- or polypeptide that functions to link the transmembrane domain to, either the antigen binding domain or, the intracellular domain in the polypeptide chain. In one embodiment, the spacer domain may comprise up to 300 amino acids, preferably 10 to 100 amino acids and most preferably 25 to 50 amino acids. In another embodiment, a short oligo- or polypeptide linker, preferably between 2 and 10 amino acids in length may form the linkage between the transmembrane domain and the intracellular domain of the CAR. An example of a linker includes a glycine-serine doublet.

Human Antibodies

It may be preferable to use human antibodies or fragments thereof when using the antigen binding domain of a CAR. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Antibodies directed against the target of choice can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Humanized Antibodies

Alternatively, in some embodiments, a non-human antibody can be humanized, where specific sequences or regions of the antibody are modified to increase similarity to an antibody naturally produced in a human. For instance, in the present invention, the antibody or fragment thereof may comprise a non-human mammalian scFv. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat.

Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized that retain high affinity for the target antigen and that possess other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody. However, using certain methods of humanization, the affinity and/or specificity of binding of the antibody to the target antigen may be increased using methods of "directed evolution," as described by Wu et al., J. Mol. Biol., 294:151 (1999), the contents of which are incorporated herein by reference herein in their entirety.

Vectors

A vector may be used to introduce the CAR into a monocyte, macrophage or dendritic cell as described elsewhere herein. In one aspect, the invention includes a vector comprising a nucleic acid sequence encoding a CAR as described herein. In one embodiment, the vector comprises a plasmid vector, viral vector, retrotransposon (e.g. piggybeck, sleeping beauty), site directed insertion vector (e.g. CRISPR, Zn finger nucleases, TALEN), or suicide expression vector, or other known vector in the art.

All constructs mentioned above are capable of use with 3rd generation lentiviral vector plasmids, other viral vectors, or RNA approved for use in human cells. In one embodiment, the vector is a viral vector, such as a lentiviral vector. In another embodiment, the vector is a RNA vector.

The production of any of the molecules described herein can be verified by sequencing. Expression of the full length proteins may be verified using immunoblot, immunohistochemistry, flow cytometry or other technology well known and available in the art.

The present invention also provides a vector in which DNA of the present invention is inserted. Vectors, including those derived from retroviruses such as lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of resulting in low immunogenicity in the subject into which they are introduced.

The expression of natural or synthetic nucleic acids is typically achieved by operably linking a nucleic acid or portions thereof to a promoter, and incorporating the construct into an expression vector. The vector is one generally capable of replication in a mammalian cell, and/or also capable of integration into the cellular genome of the mammal. Typical vectors contain transcription and translation terminators, initiation sequences, and promoters useful for regulation of the expression of the desired nucleic acid sequence.

The nucleic acid can be cloned into any number of different types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

The expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the elongation factor-1α promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Introduction of Nucleic Acids

In one aspect, the invention includes a method for modifying a cell comprising introducing a chimeric antigen receptor (CAR) into the monocyte, macrophage, or dendritic cell, wherein the CAR comprises an antigen binding domain, a transmembrane domain and an intracellular domain of a co-stimulatory molecule, and wherein the cell is a monocyte, macrophage, or dendritic cell that expresses the CAR and possesses targeted effector activity. In one embodiment, introducing the CAR into the cell comprises introducing a nucleic acid sequence encoding the CAR. In another embodiment, introducing the nucleic acid sequence comprises electroporating a mRNA encoding the CAR.

Methods of introducing and expressing genes, such as the CAR, into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). Nucleic acids can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). Nucleic acids can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. RNA vectors include vectors having a RNA promoter and/or other relevant domains for production of a RNA transcript. Viral vectors, and especially retroviral vectors, have become the most widely used method for inserting genes into mammalian, e.g., human cells. Other viral vectors may be derived from lentivirus, poxviruses, herpes simplex virus, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the molecules described herein, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, one or more of the nucleic acid sequences are introduced by a method selected from the group consisting of transducing the population of cells, transfecting the population of cells, and electroporating the population of cells. In one embodiment, a population of cells comprises one or more of the nucleic acid sequences described herein.

In one embodiment, the nucleic acids introduced into the cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a CAR.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

Some in vitro-transcribed RNA (IVT-RNA) vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In one aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of Cells

In one embodiment, phagocytic cells are used in the compositions and methods described herein. A source of phagocytic cells, such as monocytes, macrophages and/or dendritic cells, is obtained from a subject. Non-limiting examples of subjects include humans, dogs, cats, mice, rats, and transgenic species thereof. Preferably, the subject is a human. The cells can be obtained from a number of sources, including peripheral blood mononuclear cells, bone marrow, lymph node tissue, spleen tissue, umbilical cord, and tumors. In certain embodiments, any number of monocyte, macrophage, dendritic cell or progenitor cell lines available in the art, may be used. In certain embodiments, the cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, cells are isolated from peripheral blood by lysing the red blood cells and depleting the lymphocytes and red blood cells, for example, by centrifugation through a PERCOLL™ gradient. Alternatively, cells can be isolated from umbilical cord. In any event, a specific subpopulation of the monocytes, macrophages and/or dendritic cells can be further isolated by positive or negative selection techniques.

The mononuclear cells so isolated can be depleted of cells expressing certain antigens, including, but not limited to, CD34, CD3, CD4, CD8, CD14, CD19 or CD20. Depletion of these cells can be accomplished using an isolated antibody, a biological sample comprising an antibody, such as ascites fluid, an antibody bound to a physical support, and a cell bound antibody.

Enrichment of a monocyte, macrophage and/or dendritic cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, enrich of a cell population for monocytes, macrophages and/or dendritic cells by negative selection can be accomplished using a monoclonal antibody cocktail that typically includes antibodies to CD34, CD3, CD4, CD8, CD14, CD19 or CD20.

During isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. The use of high concentrations of cells can result in increased cell yield, cell activation, and cell expansion.

In one embodiment, a population of cells comprises the monocytes, macrophages, or dendritic cells of the present invention. Examples of a population of cells include, but are not limited to, peripheral blood mononuclear cells, cord blood cells, a purified population of monocytes, macrophages, or dendritic cells, and a cell line. In another embodiment, peripheral blood mononuclear cells comprise the population of monocytes, macrophages, or dendritic cells. In yet another embodiment, purified cells comprise the population of monocytes, macrophages, or dendritic cells.

In another embodiment, the cells have upregulated M1 markers and downregulated M2 markers. For example, at least one M1 marker, such as HLA DR, CD86, CD80, and PDL1, is upregulated in the phagocytic cell. In another example, at least one M2 marker, such as CD206, CD163, is downregulated in the phagocytic cell. In one embodiment, the cell has at least one upregulated M1 marker and at least one downregulated M2 marker.

In yet another embodiment, targeted effector activity in the phagocytic cell is enhanced by inhibition of either CD47 or SIRPα activity. CD47 and/or SIRPα activity may be inhibited by treating the phagocytic cell with an anti-CD47 or anti-SIRPα antibody. Alternatively, CD47 or SIRPα activity may be inhibited by any method known to those skilled in the art.

Expansion of Cells

In one embodiment, the cells or population of cells comprising monocytes, macrophages, or dendritic cells are cultured for expansion. In another embodiment, the cells or population of cells comprising progenitor cells are cultured for differentiation and expansion of monocytes, macrophages, or dendritic cells. The present invention comprises expanding a population of monocytes, macrophages, or dendritic cells comprising a chimeric antigen receptor as described herein.

As demonstrated by the data disclosed herein, expanding the cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the cells expand in the range of about 20 fold to about 50 fold.

Following culturing, the cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The culture medium may be replaced during the culture of the cells at any time. Preferably, the culture medium is replaced about every 2 to 3 days. The cells are then harvested from the culture apparatus whereupon the cells can be used immediately or stored for use at a later time The culturing step as described herein (contact with agents as described herein) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

In one embodiment, the cells may be cultured for several hours (about 3 hours) to about 14 days or any hourly integer value in between. Conditions appropriate for cell culture include an appropriate media (e.g., macrophage complete medium, DMEM/F12, DMEM/F12-10 (Invitrogen)) that may contain factors necessary for proliferation and viability, including serum (e.g., fetal bovine or human serum), L-glutamine, insulin, M-CSF, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of the cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the cells may include an agent that can activate the cells. For example, an agent that is known in the art to activate the monocyte, macrophage or dendritic cell is included in the culture medium.

Therapy

The modified cells described herein may be included in a composition for treatment of a subject. In one aspect, the composition comprises the modified cell comprising the chimeric antigen receptor described herein. The composition may include a pharmaceutical composition and further include a pharmaceutically acceptable carrier. A therapeutically effective amount of the pharmaceutical composition comprising the modified cells may be administered.

In one aspect, the invention includes a method of treating a disease or condition associated with a tumor or cancer in a subject comprising administering to the subject a therapeutically effective amount of a pharmaceutical composition comprising the modified cell described herein. In another aspect, the invention includes a method of treating a solid tumor in a subject, comprising administering to the subject a therapeutically effective amount of a pharmaceutical composition comprising the modified cell described herein. In another aspect, the invention includes a method for stimulating an immune response to a target tumor cell or tumor tissue in a subject comprising administering to a subject a therapeutically effective amount of a pharmaceutical composition comprising the modified cell described herein. In yet another aspect, the invention includes use of the modified cell described herein in the manufacture of a medicament for the treatment of an immune response in a subject in need thereof. In still another aspect, the invention includes use of the modified cell described herein in the manufacture of a medicament for the treatment of a tumor or cancer in a subject in need thereof.

The modified cells generated as described herein possess targeted effector activity. In one embodiment, the modified cells have targeted effector activity directed against an antigen on a target cell, such as through specific binding to an antigen binding domain of a CAR. In another embodiment, the targeted effector activity includes, but is not limited to, phagocytosis, targeted cellular cytotoxicity, antigen presentation, and cytokine secretion.

In another embodiment, the modified cell described herein has the capacity to deliver an agent, a biological agent or a therapeutic agent to the target. The cell may be modified or engineered to deliver an agent to a target, wherein the agent is selected from the group consisting of a nucleic acid, an antibiotic, an anti-inflammatory agent, an antibody or antibody fragments thereof, a growth factor, a cytokine, an enzyme, a protein, a peptide, a fusion protein, a synthetic molecule, an organic molecule, a carbohydrate or the like, a lipid, a hormone, a microsome, a derivative or a variation thereof, and any combination thereof. As a non-limiting example, a macrophage modified with a CAR that targets a tumor antigen is capable of secreting an agent, such as a cytokine or antibody, to aid in macrophage function. Antibodies, such as anti-CD47/antiSIRPα mAB, may also aid in macrophage function. In yet another example, the macrophage modified with a CAR that targets a tumor antigen is engineered to encode a siRNA that aids macrophage function by downregulating inhibitory genes (i.e. SIRPα). Another example, the CAR macrophage is engineered to express a dominant negative (or otherwise mutated) version of a receptor or enzyme that aids in macrophage function.

In one embodiment, the macrophage is modified with multiple genes, wherein at least one gene includes a CAR and at least one other gene comprises a genetic element that enhances CAR macrophage function. In another embodiment, the macrophage is modified with multiple genes, wherein at least one gene includes a CAR and at least one other gene aids or reprograms the function of other immune cells (such as T cells within the tumor microenvironment).

Further, the modified cells can be administered to an animal, preferably a mammal, even more preferably a human, to suppress an immune reaction, such as those common to autoimmune diseases such as diabetes, psoriasis, rheumatoid arthritis, multiple sclerosis, GVHD, enhancing allograft tolerance induction, transplant rejection, and the like. In addition, the cells of the present invention can be used for the treatment of any condition in which a diminished or otherwise inhibited immune response, especially a cell-mediated immune response, is desirable to treat or alleviate the disease. In one aspect, the invention includes treating a condition, such as an autoimmune disease, in a subject, comprising administering to the subject a therapeutically effective amount of a pharmaceutical composition comprising a population of the cells described herein. In addition, the cells of the present invention can be administered as pre-treatment or conditioning prior to treatment with an alternative anti-cancer immunotherapy, including but not limited to CAR T cells, tumor-infiltrating lymphocyte, or a checkpoint inhibitor.

Examples of autoimmune disease include but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

The cells can also be used to treat inflammatory disorders. Examples of inflammatory disorders include but are not limited to, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

The cells of the present invention can be used to treat cancers. Cancers include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the cells of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, allogeneic or xenogeneic with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

Pharmaceutical Compositions

Pharmaceutical compositions of the present invention may comprise the cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-immune response effective amount", "an immune response-inhibiting effective amount", or "therapeutic amount" is indicated, the precise amount of the compositions of the present invention to be administered can be determined by a physician with consideration of individual differences in age, weight, immune response, and condition of the patient (subject). It can generally be stated that a pharmaceutical composition comprising the cells described herein may be administered at a dosage of $10^4$ to $10^9$ cells/kg body weight, preferably $10^5$ to $10^6$ cells/kg body weight, including all integer values within those ranges. The cell compositions described herein may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer monocytes, macrophages, or dendritic cells to a subject and then subsequently redraw blood (or have an apheresis performed), activate the monocytes, macrophages, or dendritic cells therefrom according to the present invention, and reinfuse the patient with these activated cells. This process can be carried out multiple times every few weeks. In certain embodiments, the cells can be activated from blood draws of from 10 ml to 400 ml. In certain embodiments, the cells are activated from blood draws of 20 ml, 30 ml, 40 ml, 50 ml, 60 ml, 70 ml, 80 ml, 90 ml, or 100 ml. Not to be bound by theory, using this multiple blood draw/multiple reinfusion protocol, may select out certain populations of cells.

In certain embodiments of the present invention, cells are modified using the methods described herein, or other methods known in the art where the cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or treatments for PML patients. In further embodiments, the cells of the invention may be used in combination with CART cell therapy, chemotherapy, radiation, immunosuppressive agents, such as cyclosporin, azathioprine, methotrexate, mycophenolate, and FK506, antibodies, or other immunoablative agents such as anti-CD52 antibody alemtuzumab (CAM PATH), anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, lymphocyte ablative therapy using either chemotherapy agents such as, fludarabine, external-beam radiation therapy (XRT), cyclophosphamide, Rituxan, or antibodies such as OKT3 or CAMPATH. For example, in one embodiment, subjects may undergo standard treatment with high dose chemotherapy followed by peripheral blood stem cell transplantation. In certain embodiments, following the transplant, subjects receive an infusion of the cells of the present invention. In an additional embodiment, the cells may be administered before or following surgery.

The dosage of the above treatments to be administered to a subject will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Cell Culture: THP1, K562, SKOV3, SKBR3, HDLM2, MD468, and all cell lines were cultured in RPMI 1640 supplemented with 10% fetal bovine serum and penicillin/streptomycin at 37 C in 5% CO2. A THP1 mRFP+ subline (Wt) was generated by lentiviral transduction and FACS purification of mRFP+ cell lines. The THP1 mRFP+ subline was used to generate THP1 mRFP+ CAR19z+(CAR19z; CARMA19z), THP1 mRFP+ CAR19Δz+(CAR19Δz; CARMA19Δz), THP1 mRFP+ MesoZ+ and THP1 mRFP+ CARHer2z+(CARHer2z; CARMAHer2z) sublines. Monocyte differentiation was induced by culturing cells for 48 hours with 1 ng/mL phorbol 12-myristate 13-acetate in culture media.

Primary Human Macrophages: Primary human monocytes were purified from normal donor apheresis product using Miltenyi CD14 MicroBeads (Miltenyi, 130-050-201). Monocytes were cultured in X-Vivo media supplemented with 5% human AB serum or RPMI 1640 supplemented with 10% fetal bovine serum, with penicillin/streptomycin, glutamax, and 10 ng/mL recombinant human GM-CSF (PeproTech, 300-03) for 7 days in MACS GMP Cell Differentiation Bags (Miltenyi, 170-076-400). Macrophages were harvested on day 7 and cryopreserved in FBS+10% DMSO pending subsequent use.

Phagocytosis Assay: Wt or CARMA mRFP+THP1 sublines were differentiated for 48 hours with 1 ng/mL phorbol 12-myristate 13-acetate. GFP+antigen bearing tumor sublines, i.e. K562 CD19+ GFP+ cells, were added to the differentiated THP1 macrophages at a 1:1 ratio following PMA washout. Macrophages were co-cultured with target tumor cells for 4 hours, and phagocytosis was quantified by fluorescent microscopy using the EVOS FL Auto Cell Imaging System. An average of three fields of view was considered as n, and all conditions were quantified in triplicates. FACS based phagocytosis was analyzed on a BD LSR-Fortessa. FlowJo (Treestar, Inc.) was used to analyze flow cytometric data. Live, singlets gated mRFP/GFP double positive events were considered phagocytosis. CD47/SIRPα axis blockade was performed via addition of blocking monoclonal antibodies at the initiation of co-culture at indicated concentrations (mouse anti-human CD47 clone B6H12, eBioscience #14-0479-82; mouse anti-human CD47 clone 2D3 as negative control, eBioscience #14-0478-82; mouse anti-human SIRPα clone SE5A5, BioLegend #323802). TLR co-stimulation was performed by adding TLR1-9 agonists (Human TLR 1-9 agonist kit; Invivogen #tlrl-kitlhw) at the time of co-culture.

In Vitro Killing Assay: Wt or CAR bearing macrophages were co-cultured with antigen-bearing or control clickbeetle green luciferase (CBG)/green fluorescent protein (GFP) positive target tumor cells at varying effector to target ratios (starting at 30:1 and decreasing in three-fold dilutors). Bioluminescent imaging was utilized to determine tumor burden, using the IVIS Spectrum Imaging System (Perkin Elmer). Percent specific lysis was calculated as follows:

% Specific Lysis=((Treated well−Tumor alone well)/
(Maximal killing−tumor alone well)*100)

Time-Lapse Microscopy: Fluorescent time-lapse video microscopy of CAR mediated phagocytosis was performed using the EVOS FL Auto Cell Imaging System. Images were captured every 40 seconds for 18 hours. Image analysis was performed with FIJI imaging software.

Lentiviral production and transfection: Chimeric antigen receptor constructs were de novo synthesized by GeneArt (Life Technologies) and cloned into a lentiviral vector as previously described. Concentrated lentivirus was generated using HEK293T cells as previously described.

Adenoviral production and transfection: Ad5f35 chimeric adenoviral vectors encoding GFP, CAR, or no transgene under a CMV promoter were produced and titrated as per standard molecular biology procedure. Primary human macrophages were transduced with varying multiplicities of infection and serially imaged for GFP expression and viability using the EVOS FL Auto Cell Imaging System. CAR expression was assessed by FACS analysis of surface CAR expression using His-tagged antigen and anti-His-APC secondary antibody (R&D Biosystems Clone AD1.1.10).

Flow Cytometry: FACS was performed on a BD LSR Fortessa. Surface CAR expression was detected with biotinylated protein L (GenScript M00097) and streptavidin APC (BioLegend, #405207) or His-tagged antigen and anti-His-APC secondary antibody (R&D Biosystems Clone AD1.1.10). Fc receptors were blocked with Human Trustain FcX (BioLegend, #422301) prior to staining. CD47 expression was determined using mouse anti-human CD47 APC (eBioscience #17-0479-41) with mouse IgG1 kappa APC isotype control for background determination. Calreticulin expression was determined with mouse anti-calreticulin PE clone FMC75 (Abcam #ab83220). All flow results are gated on live (Live/Dead Aqua Fixable Dead Cell Stain, Life Technologies L34957) single cells.

Imagestream Cytometry: FACS with single cell fluorescent imaging was performed on an ImageStream Mark II Imaging Flow Cytometer (EMD Millipore). Briefly, mRFP+ or DiI stained macrophages (CAR or control) were co-cultured with GFP+ tumor cells for 4 hours, prior to fixation and ImageStream data acquisition. Data was analyzed using ImageStream software (EMD Millipore).

RNA Electroporation: CAR constructs were cloned into in vitro transcription plasmids under the control of a T7 promoter using standard molecular biology techniques. CAR mRNA was in vitro transcribed using an mMessage mMachine T7 Ultra In Vitro Transcription Kit (Thermo Fisher), purified using RNEasy RNA Purification Kit (Qiagen), and electroporated into human macrophages using a BTX ECM850 electroporator (BTX Harvard Apparatus). CAR expression was assayed at varying time points post-electroporation using FACS analysis.

TLR/Dectin-1 Priming: TLR or Dectin-1 priming in Wt or CAR macrophages prior to in vitro phagocytosis or killing assays was performed by pre-incubating the cells with recommended doses of either TLR 1-9 agonists (Human TLR1-9 Agonist Kit, Invivogen) or beta-glucan (MP Biomedicals, LLC), respectively, for 30 minutes prior to co-culture. In vitro function of Wt or CAR macrophages was compared between unprimed and primed conditions.

Macrophage/Monocyte Phenotype: The following surface markers were assessed as part of a macrophage/monocyte immunophenotype FACS panel, for M1/M2 distinction: CD80, CD86, CD163, CD206, CD111B, HLA-DR, HLA-A/B/C, PDL1, and PDL2 (BioLegend). TruStain FcX was used for Fc receptor blockade prior to immunostaining. Macrophages/monocytes were exposed to activating conditions, i.e. Ad5f35 transduction for 48 hours, or not, prior to phenotype assessment.

Seahorse Assay: Metabolic phenotype and oxygen consumption of macrophages was determined using the Seahorse assay (Seahorse XF, Agilent). Control or CAR macrophages were exposed to media control or immunosuppressive cytokines for 24 hours prior to analysis. Cells were treated with oligomycin, FCCP, and rotenone sequentially throughout the Seahorse assay. The assay was performed with 6 replicates per condition.

In Vivo Assays: NOD-scid IL2Rg-null-IL3/GM/SF, NSG-SGM3 (NSGS) mice were used used for human xenograft models. Mice engrafted with CBG-luciferase positive human SKOV3 ovarian cancer cells were either left untreated, or treated with untransduced, empty Ad5f35 transduced, or Ad5f35 CAR-HER2 transduced human macrophages at different doses. Serial bioluminescent imaging was performed to monitor tumor burden (IVIS Spectrum, Perkin Elmer). Organs and tumor were harvested upon sacrifice for FACS analysis. Overall survival was monitored and compared using Kaplan-Meier analysis.

The results of the experiments are now described.

FIG. 1A is a conceptual diagram of a chimeric antigen receptor (CAR) comprised of a gene/gene-product containing an extracellular domain with targeting function, a hinge domain, a transmembrane domain, an intracellular signaling domain(s), and/or a 2A (P2A, T2A) for stoichiometric co-expression of an additional gene product which may or may not be secreted, including any gene/transcript/protein, including but not limited to a cytokine, monoclonal antibody, antibody fragment, single chain variable fragment, enzyme, additional receptor, dominant negative receptor, tumor associated antigen(s), and any combination thereof. In addition, the CAR construct may include co-delivery of CRISPR/Cas9 gene editing material, or be introduced in the context of a CRISPR/Cas9 pre-edited cell. Specific examples of CAR constructs are modeled in FIG. 1B, including CARMA-ζ, CARMA-γ, and CARMA-Dectin, which contain an antigen specific scFv, CD8 hinge, CD8 transmembrane, and a CD3 ζ, FcεRI common γ subunit, or the intracellular domain of Dectin-1, respectively.

Figure 2A:
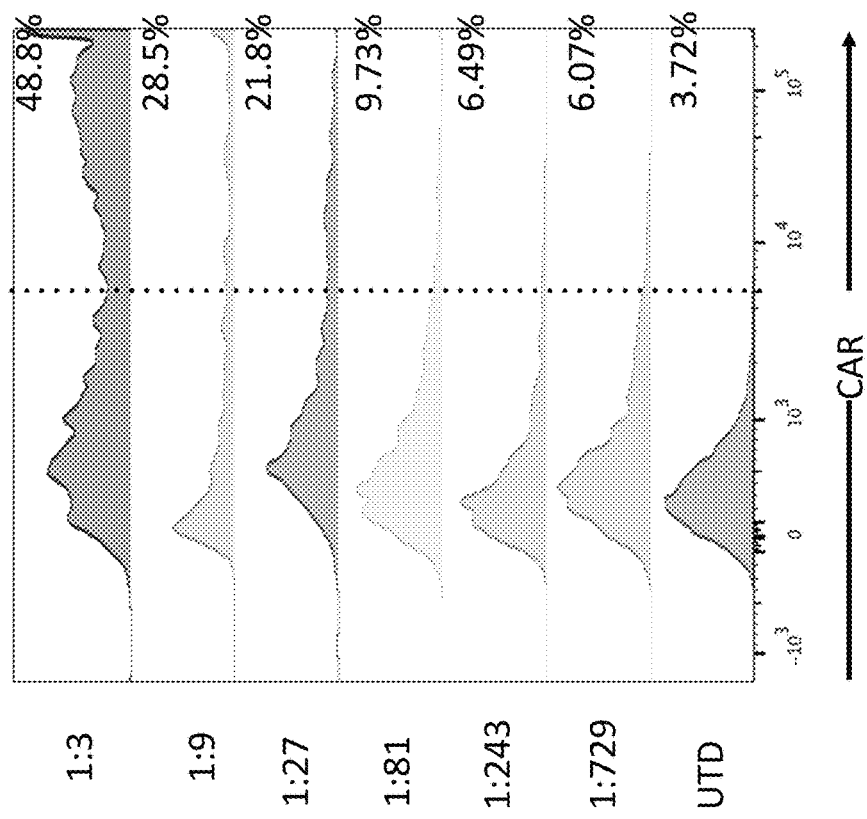
FIG. 2A is a graph showing CAR19z expressed on the surface of myeloid cells post lentiviral transduction. CAR19z lentivirus was titrated in three-fold dilutors and used to transduce 1e5/0.1 mL mRFP+THP1 cells. mRFP is a reporter gene (red fluorescent protein) that was expressed by lentiviral transduction of the myeloid cell line THP1. These cells can be induced to differentiate to macrophages upon exposure to the chemical PMA. THP1 cells were harvested 24 hours post-transduction and stained for CAR surface expression with biotinylated-protein L followed by streptavidin-APC.
Figure 2C:
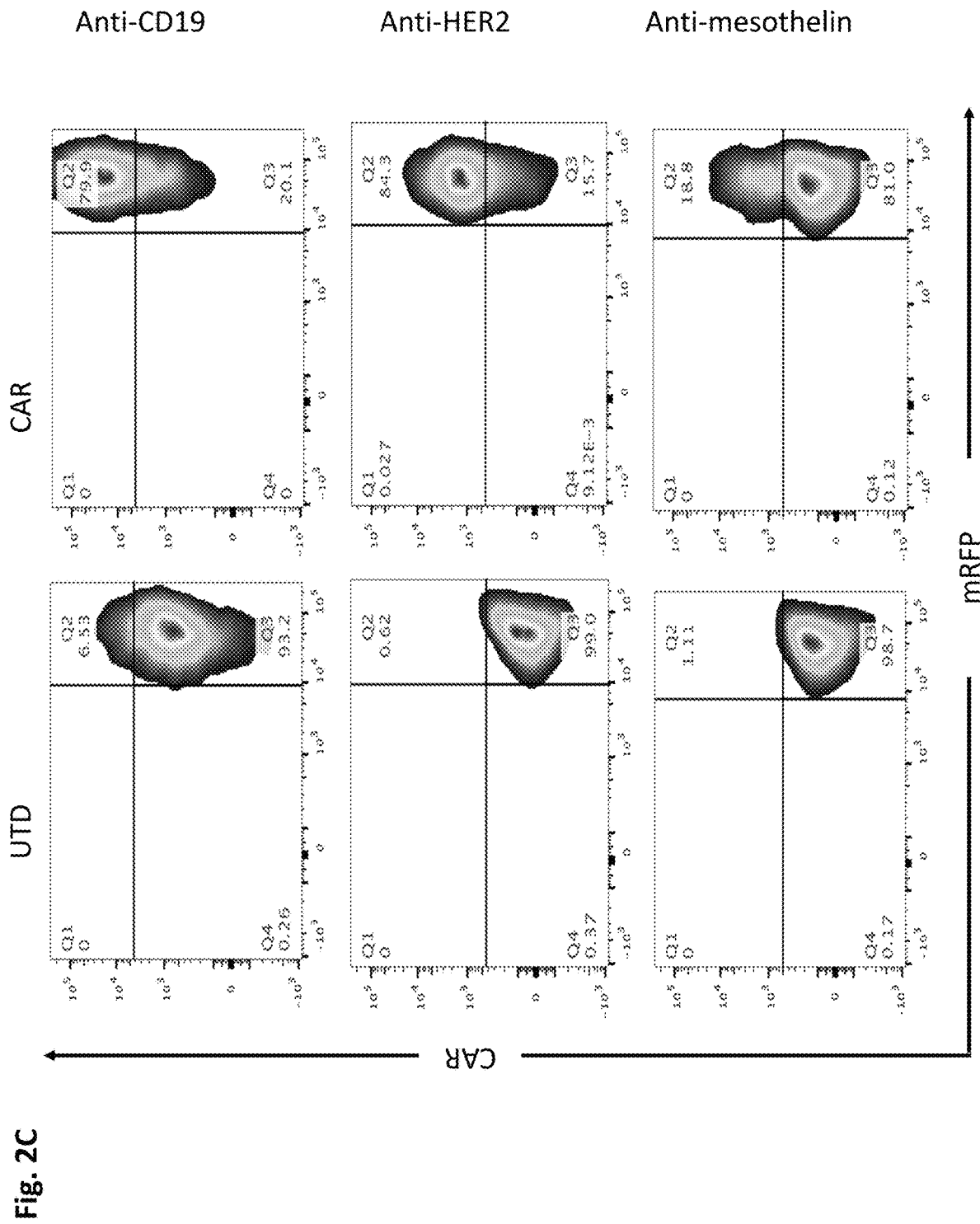
FIG. 2C demonstrates expression of anti-CD19, anti-HER2, and anti-mesothelin lentiviral CAR constructs on THP1 macrophages, with CAR(+) events in the upper right quadrant.

FIG. 2A is a graph showing CAR19z expressed on the surface of myeloid cells post lentiviral transduction. CAR19z lentivirus was titrated in three-fold dilutors and used to transduce 1e5/0.1 mL mRFP+THP1 cells. mRFP is a reporter gene (red fluorescent protein) that was expressed by lentiviral transduction of the myeloid cell line THP1. These cells can be induced to differentiate to macrophages upon exposure to the chemical PMA. THP1 cells were harvested 24 hours post-transduction and stained for CAR surface expression with biotinylated-protein L followed by streptavidin-APC. Transduced THP1 cells were expanded and sorted by FACS to generate a 100% CAR19z positive mRFP+THP1 subline (FIG. 2B). FIG. 2C demonstrates expression of anti-CD19, anti-HER2, and anti-mesothelin lentiviral CAR constructs on THP1 macrophages, with CAR (+) events in the upper right quadrant.

FIG. 3A is a flow chart showing the overview of CARMA subline generation using a THP1 macrophage model, differentiation with 1 ng/mL phorbol 12-myristate 13-acetate (PMA), and in vitro phagocytosis assay. Anti-CD19, anti-HER2, and anti-mesothelin CAR macrophages, but not wild type (Wt) macrophages, phagocytosed K562 tumor cells that expressed CD19, HER2, or mesothelin, respectively, as demonstrated by fluorescent microscopy based phagocytosis assays (FIGS. 3B-3D). CARMA tumor phagocytosis was further validated by a flow cytometric based assay, in which mRFP+CARMA against CD19 were co-cultured with CD19+ GFP+K562 cells and double positive events were quantified (representative FACS plot shown—FIG. 3E). A standard 10× field of view used in the tabulation of CARMA phagocytosis function is shown, either mRFP alone (FIG. 3F) or overlay (FIG. 3G). FACS based mRFP/GFP double positive events were defined as phagocytic events, and were validated as such by Amnis Imagestream FACS analysis. Events shown are gated on double positive events and ordered from high to low by the Amnis Imagestream phagocytosis-erode algorithm (FIG. 3H). Phagocytosis of tumor cells by mRFP+CARMA in the THP-1 cell line model was further demonstrated by confocal microscopy, verifying that GFP+ tumor cells have been completely enclosed within phagosomes via three-dimensional confocal z-stack reconstructions (FIGS. 3I and 3J). FIG. 3K demonstrates the fate of a single CARMA cell over time—with contact and immunological synapse formation being the first step, leading to phagocytic engulfment, degradation of tumor using loss of GFP as a marker of cell death, phagosome breakdown, and phagosome repair—demonstrating that CARMA survive post tumor cell phagocytosis. The data herein demonstrate the capacity for CARMA to polyphagocytose many tumor cells at once.

Anti-CD19 CAR macrophages were tested using in an in vitro phagocytosis assay against CD19+(target) or CD19− (control) GFP+K562 tumor cells. Demonstrating the antigen specificity of CARMA, only antigen-bearing tumor cells were phagocytosed (FIG. 4A). To demonstrate the requirement for the intracellular signaling domain in CARMA function, CAR19-Δζ constructs (which lack an intracellular signaling domain) were utilized. CAR19-Δζ macrophages failed to phagocytose tumor cells and had significantly reduced anti-tumor function via an in vitro luciferase based specific lysis assay (FIGS. 4B and 4C). In vitro CARMA phagocytosis assays were performed in the presence of R406 (Syk inhibitor), cytochalasin D (actin polymerization inhibitor), or blebbistatin (non-muscle myosin IIA inhibitor). R406, cytochalasin D, and blebbistatin independently abrogated the phagocytic function of CARMA, indicating that CAR signaling in macrophages is Syk dependent and results in actin polymerization and NMIIA mediated phagocytic function (FIGS. 4D-4F).

Figure 5B:
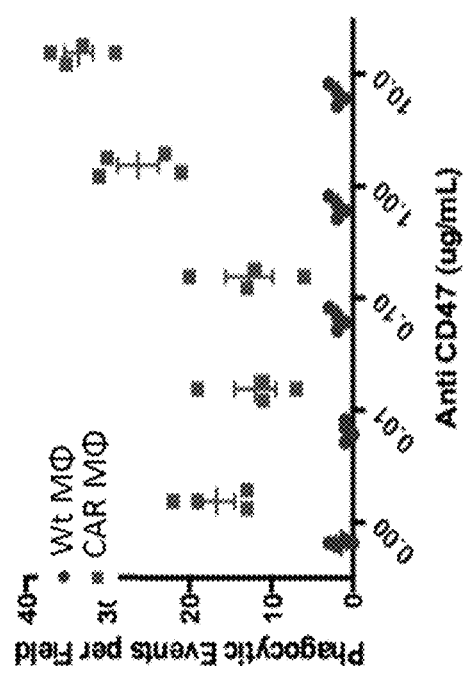
FIG. 5B is a graph showing that the addition of anti-CD47 monoclonal antibody selectively enhanced CAR but not Wt macrophage mediated phagocytosis of target antigen bearing tumor cells. Wt or CAR19ζ macrophages were incubated with CD19+K562 tumor cells either with 0, 0.01, 0.10, 1.00, or 10.0 mcg/mL anti-CD47 monoclonal antibody.
Figure 5C:
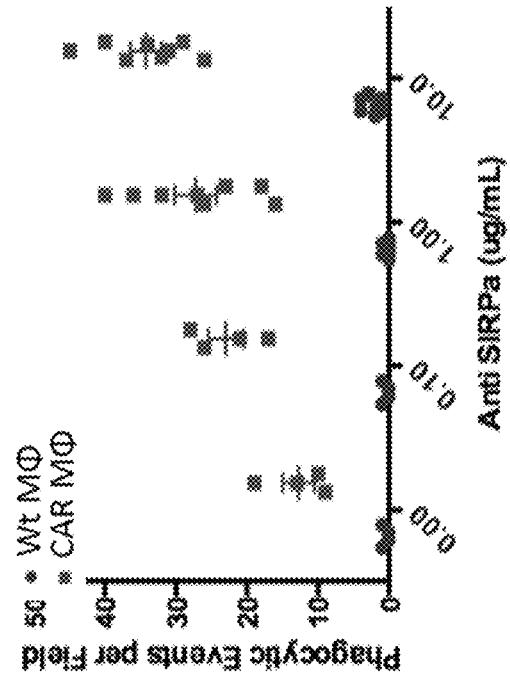
FIG. 5C is a graph showing that the addition of anti-SIRPα monoclonal antibody selectively enhanced CAR but not Wt macrophage mediated phagocytosis of target antigen bearing tumor cells. Wt or CAR19ζ macrophages were incubated with CD19+K562 tumor cells either with 0, 0.01, 0.10, 1.00, or 10.0 mcg/mL anti-SIRPα monoclonal antibody.
Figure 5A:
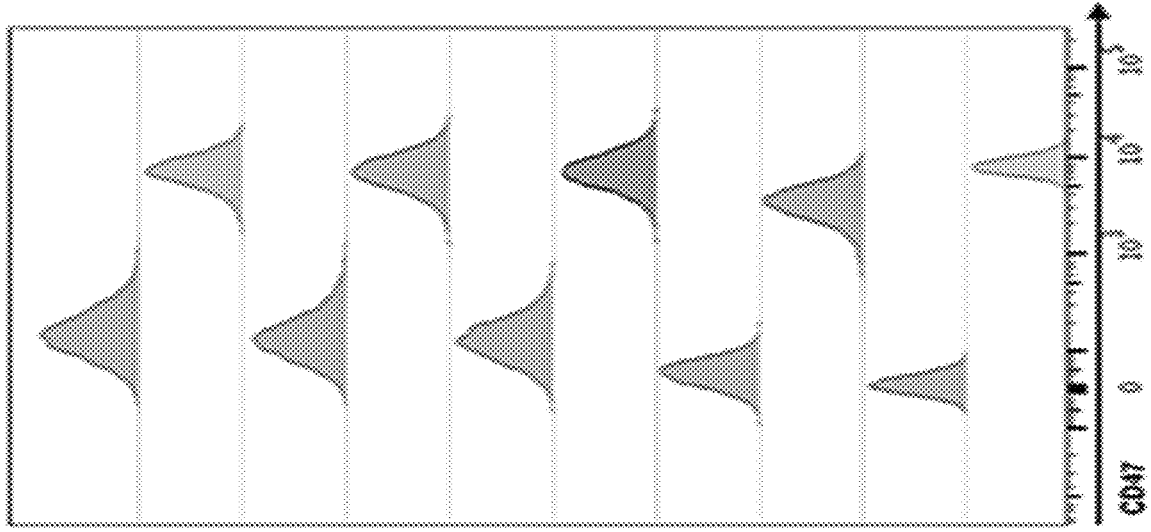
FIG. 5A is a flow cytometric graph showing expression of CD47 on target tumor cell lines relative to isotype control. K562 and K562-CD19+(K19) were used in these experiments, both of which are high CD47 expressing cell lines.

FIG. 5A is a flow cytometric graph showing expression of CD47 on target tumor cell lines relative to isotype control. K562 and K562-CD19+(K19) were used in these experiments, both of which are high CD47 expressing cell lines.

FIG. 5B is a graph showing that the addition of anti-CD47 monoclonal antibody selectively enhanced CAR but not Wt macrophage mediated phagocytosis of target antigen bearing tumor cells. Wt or CAR19ζ macrophages were incubated with CD19+K562 tumor cells either with 0, 0.01, 0.10, 1.00, or 10.0 mcg/mL anti-CD47 monoclonal antibody.

FIG. 5C is a graph showing that the addition of anti-SIRPα monoclonal antibody selectively enhanced CAR but not Wt macrophage mediated phagocytosis of target antigen bearing tumor cells. Wt or CAR19ζ macrophages were incubated with CD19+K562 tumor cells either with 0, 0.01, 0.10, 1.00, or 10.0 mcg/mL anti-SIRPα monoclonal antibody.

Figure 5D:
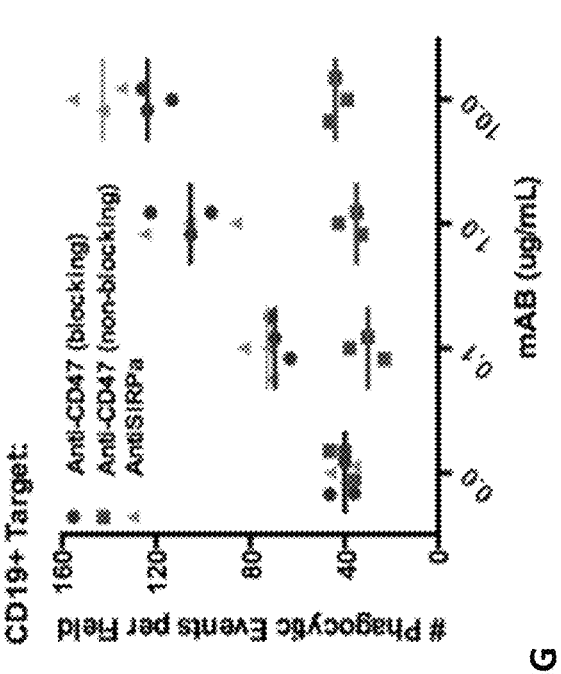
FIG. 5D is a graph demonstrating that blockade of the CD47/SIRPα axis with anti-SIRPα monoclonal antibodies enhanced the polyphagocytic (defined as a macrophage that has engulfed 2 or more tumor cells at once) by CAR macrophages.

FIG. 5D is a graph demonstrating that blockade of the CD47/SIRPα axis with anti-SIRPα monoclonal antibodies enhanced the polyphagocytic (defined as a macrophage that has engulfed 2 or more tumor cells at once) by CAR macrophages.

To control for the added opsonization by the CD47/SIRPα blocking monoclonal antibodies, a control anti-CD47 monoclonal antibody (clone 2D3), which binds CD47 but does not block the CD47 to SIRPα binding site, was used in an in vitro phagocytosis assay. Only the clone which blocked the binding site (Anti-CD47 clone B6H12) or blockade of the SIRPα receptor directly lead to enhancement of CARMA tumor phagocytosis (FIG. 5E).

Figure 5F:
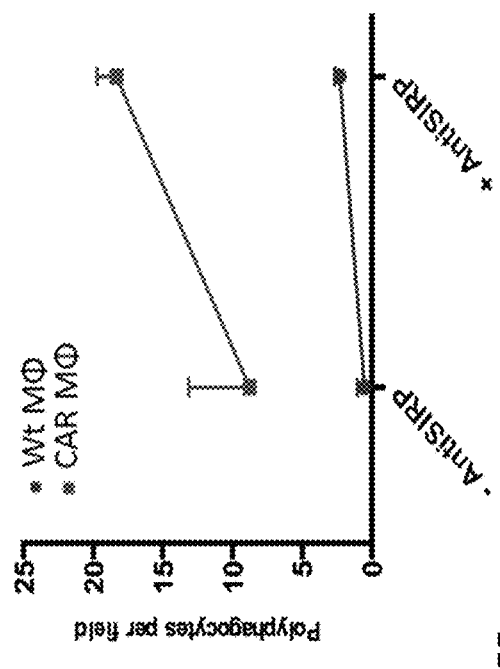
FIG. 5F is a graph showing an in vitro phagocytosis against antigen-negative (CD19 negative) tumor cells. To test whether blockade of the CD47/SIRPα axis on CAR macrophages leads to loss of antigen specificity, an in vitro phagocytosis against antigen-negative (CD19 negative) tumor cells was conducted in the presence of anti-CD47 or anti-SIRPα monoclonal antibody, and there was no observable phagocytosis.
Figure 5E:
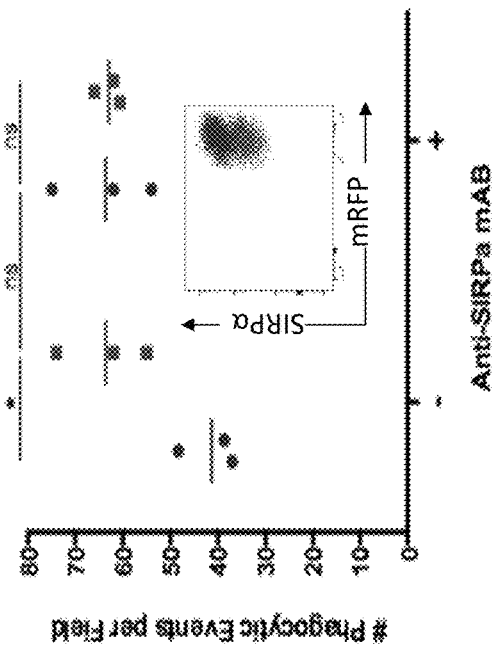
FIG. 5E is a graph showing an in vitro phagocytosis assay. To control for the added opsonization by the CD47/SIRPα blocking monoclonal antibodies, a control anti-CD47 monoclonal antibody (clone 2D3), which binds CD47 but does not block the CD47 to SIRPα binding site, was used in an in vitro phagocytosis assay. Only the clone which blocked the binding site (anti-CD47, clone B6H12) or blockade of the SIRPα receptor directly lead to enhancement of CARMA tumor phagocytosis.

To test whether blockade of the CD47/SIRPα axis on CAR macrophages leads to loss of antigen specificity, an in vitro phagocytosis against antigen-negative (CD19 negative) tumor cells was conducted in the presence of Anti-CD47 or Anti-SIRPα monoclonal antibody, and there was no observable phagocytosis (FIG. 5F).

Figure 5G:
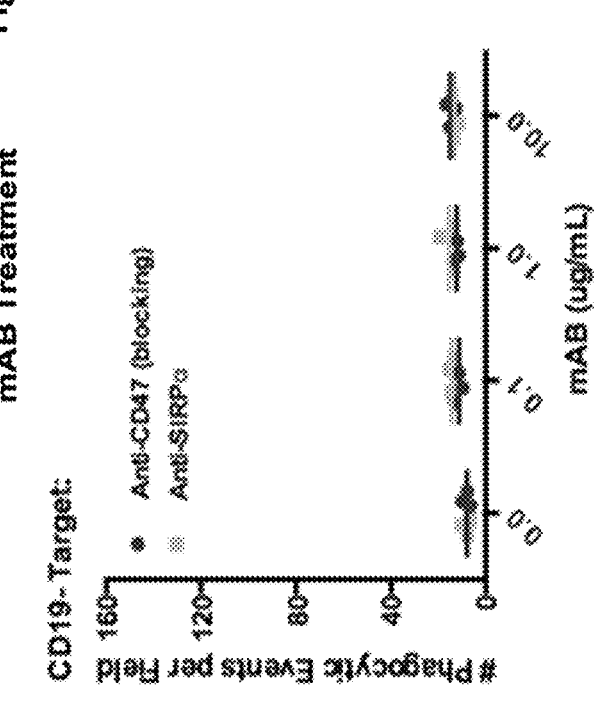
FIG. 5G is a graph showing the specificity of CARMA phagocytic enhancement in the presence of SIRPα blocking monoclonal antibody tested by knocking out the SIRPα receptor on THP1 macrophages, and comparing tumor phagocytosis by CARMA or SIRPα-KO CARMA in the absence or presence of anti-SIRPα antibody. CRISPR/Cas9 was used for SIRPα deletion, and cells were sorted for SIRPα negativity prior to functional assays. Knocking out SIRPα enhanced CARMA function, and adding anti-SIRPα back to the knockout cells failed to further enhance phagocytosis.

The specificity of CARMA phagocytic enhancement in the presence of SIRPα blocking monoclonal antibody was tested by knocking out the SIRPα receptor on THP1 macrophages, and comparing tumor phagocytosis by CARMA or SIRPα-KO CARMA in the absence or presence of anti-SIRPα antibody. CRISPR/Cas9 was used for SIRPα deletion, and cells were sorted for SIRPα negativity prior to functional assays. Knocking out SIRPα enhanced CARMA function, and adding anti-SIRPα back to the knockout cells failed to further enhance phagocytosis (FIG. 5G).

Figure 6A:
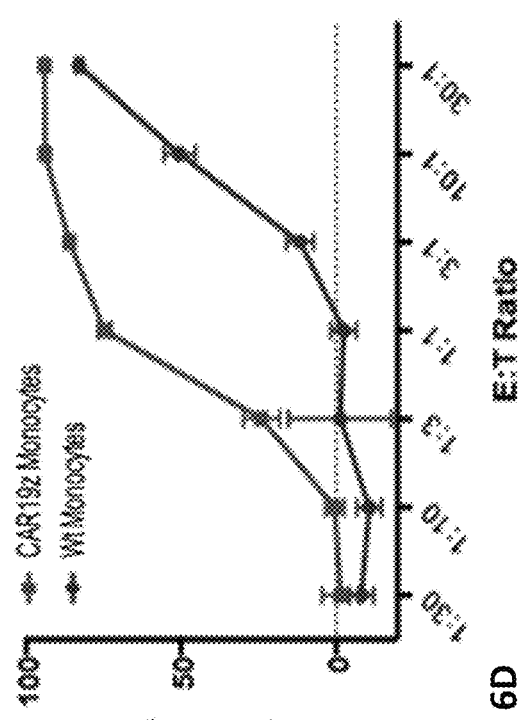
FIG. 6A is a graph showing the specific lysis of CD19+ GFP+ Luciferase+K562 cells by CAR19ζ CARMA but not Wt macrophages (using the THP-1 macrophage model) in an in vitro luciferase based killing assay at 48 hours in a dose dependent manner.

FIG. 6A demonstrates the specific lysis of CD19+ GFP+ Luciferase+K562 cells by CAR19ζ CARMA but not Wt macrophages (using the THP-1 macrophage model) in an in vitro luciferase based killing assay at 48 hours in a dose dependent manner.

Figure 6B:
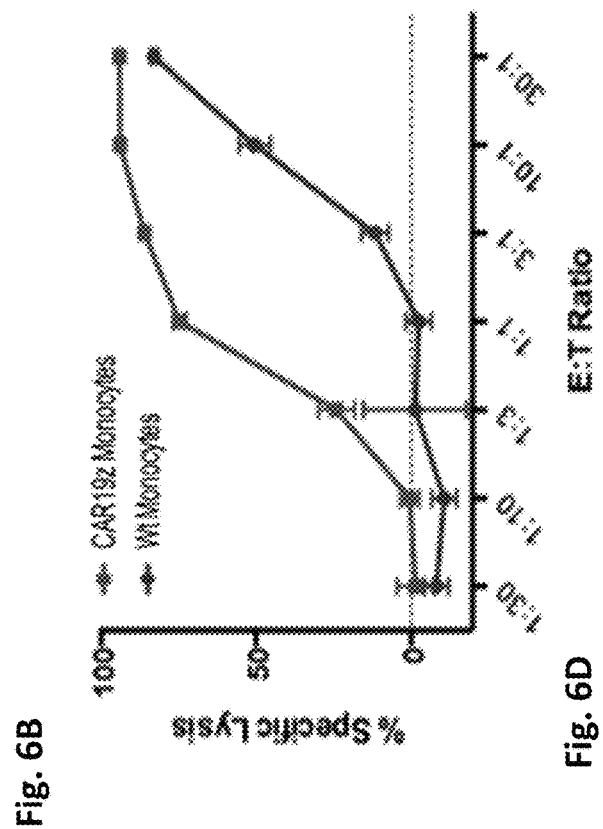
FIG. 6B is a graph demonstrating the specific lysis of tumor cells by CAR19ζ or Wt THP-1 monocytes (undifferentiated, thus a model of monocytes rather than macrophages) in an in vitro luciferase based killing assay at 48 hours in a dose dependent manner.

FIG. 6B is a graph demonstrating the specific lysis of tumor cells by CAR19ζ or Wt THP-1 monocytes (undifferentiated, thus a model of monocytes rather than macrophages) in an in vitro luciferase based killing assay at 48 hours in a dose dependent manner.

Figure 6C:
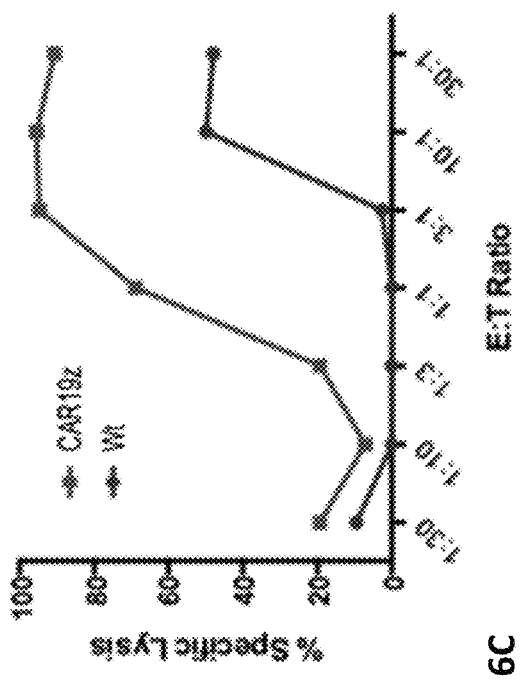
FIG. 6C is a panel of images showing the luciferase driven bioluminescence, derived from luciferase positive CD19+K562 tumor cells, after 48-hour co-culture with Wt or CAR19ζ macrophages in vitro, in the absence or presence of 10 μg/mL anti-SIRPα monoclonal antibody.
Figure 6D:
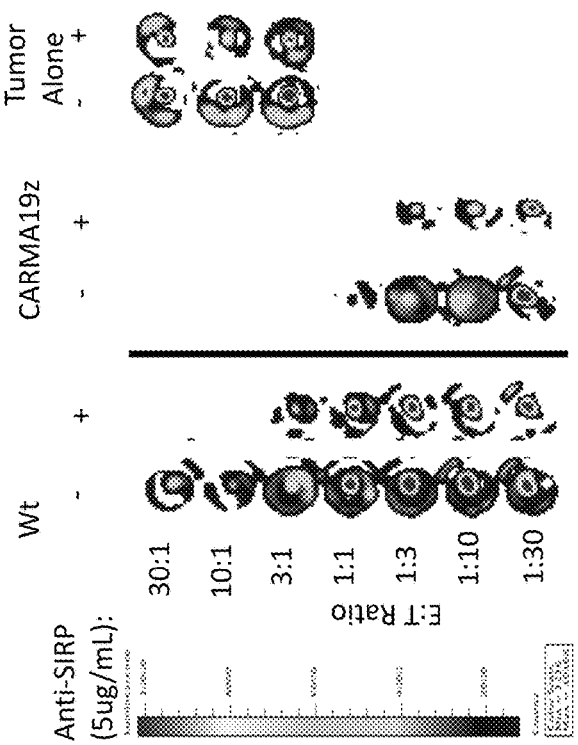
FIG. 6D is a graph demonstrating the specific lysis of Wt or CAR19ζ macrophages +/−anti-SIRPα monoclonal antibody.

FIG. 6C is a panel of images showing the luciferase driven bioluminescence, derived from luciferase positive CD19+K562 tumor cells, after 48-hour co-culture with Wt or CAR19ζ macrophages in vitro, in the absence or presence of 10 mcg/mL anti-SIRPα monoclonal antibody. FIG. 6D is a graph demonstrating the specific lysis of Wt or CAR19ζ macrophages+/−anti-SIRPα monoclonal antibody.

Figure 7A:
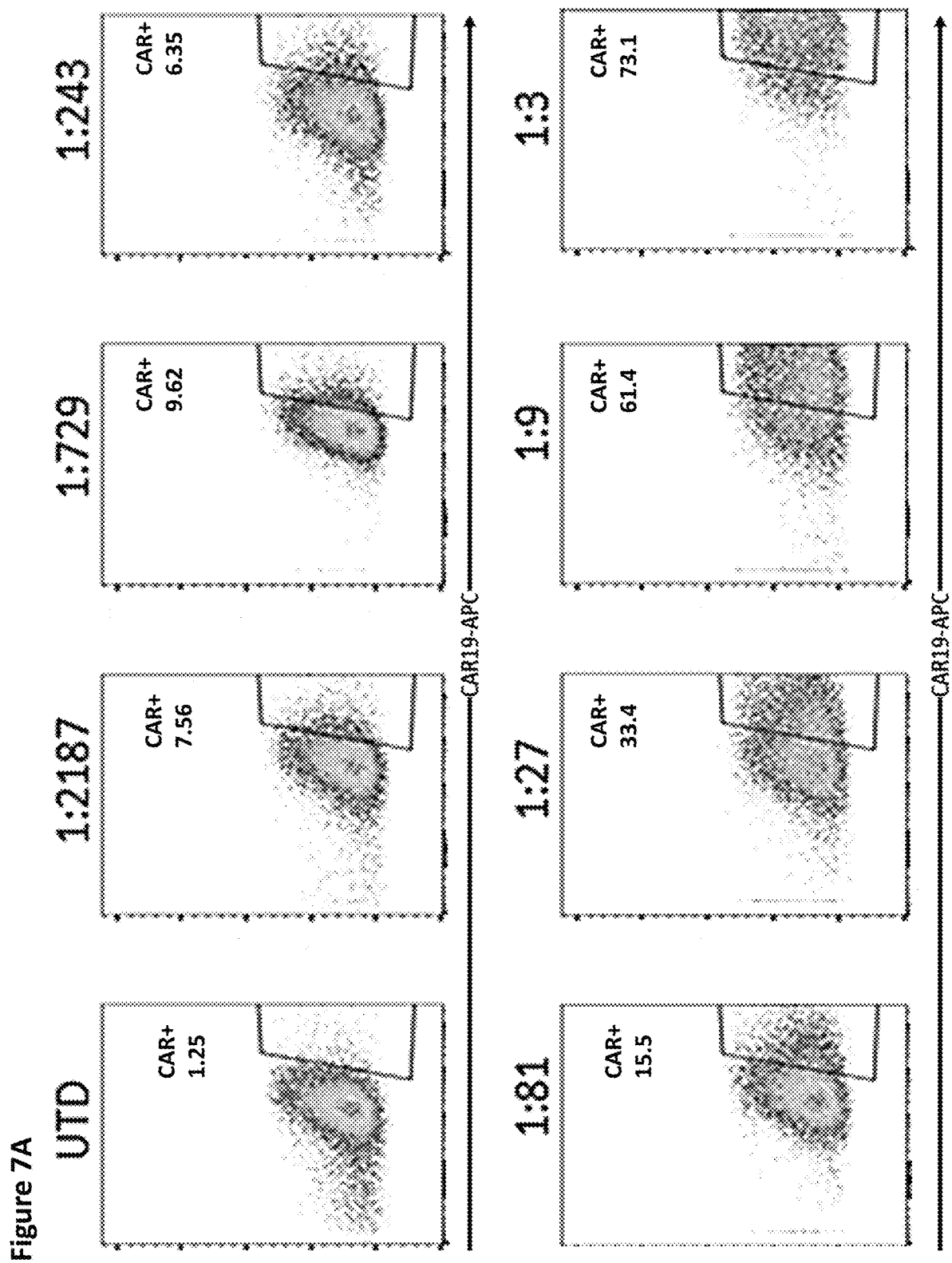
FIG. 7A is a series of graphs showing CAR constructs with an FcεRI common γ (CAR19γ, CARMA197) subunit intracellular domain were generated, packaged into lentivirus, and used to transduce THP-1 myeloid cells in a threefold serial viral dilution. CAR19γ was expressed on THP-1 macrophages.

CAR constructs with an FcεRI common γ (CAR19γ, CARMA197) subunit intracellular domain were generated, packaged into lentivirus, and used to transduce THP-1 myeloid cells in a three-fold serial viral dilution. CAR19γ was expressed on THP-1 macrophages (FIG. 7A).

CAR19γ macrophages or CAR19ζ macrophages were sorted for 100% CAR positivity and utilized for in vitro functional characterization. CAR19ζ and CAR19γ macrophages both phagocytosed CD19+ tumor cells, and both displayed synergy with blockade of the CD47/SIRPα axis by the addition of anti-SIRPα monoclonal antibody (FIG. 7B).

Figure 7C:
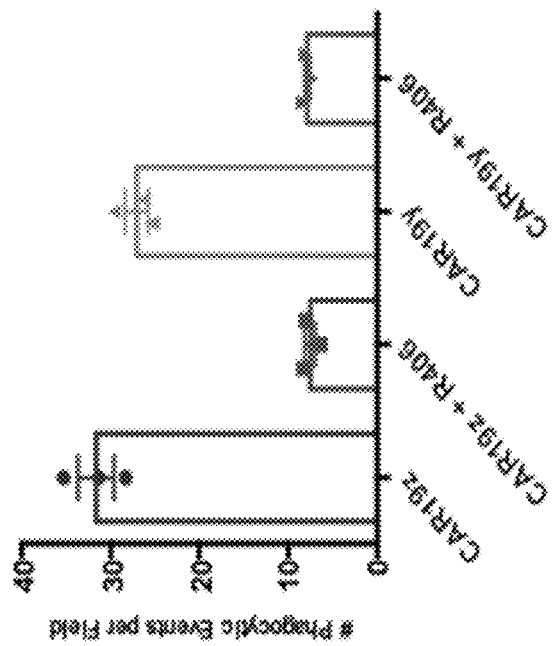
FIG. 7C is a graph showing an R406 Syk inhibition in vitro phagocytosis assay that demonstrates that CAR19ζ and CAR19γ macrophages both signal via Syk to drive tumor phagocytosis.
Figure 7B:
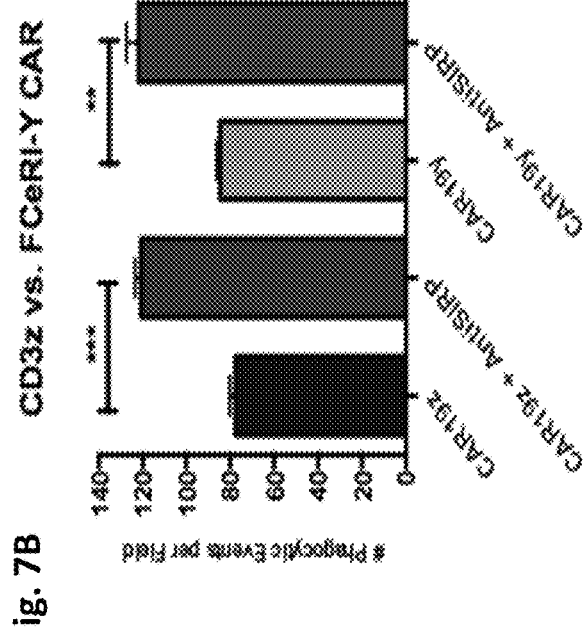
FIG. 7B is a graph showing CAR19γ macrophages or CAR19ζ macrophages sorted for 100% CAR positivity and utilized for in vitro functional characterization. CAR19ζ and CAR19γ macrophages both phagocytosed CD19+ tumor cells, and both displayed synergy with blockade of the CD47/SIRPα axis by the addition of anti-SIRPα monoclonal antibody

CAR19ζ and CAR19γ macrophages both signal via Syk to drive tumor phagocytosis, as demonstrated in an R406 Syk inhibition in vitro phagocytosis assay (FIG. 7C).

Figure 7D:
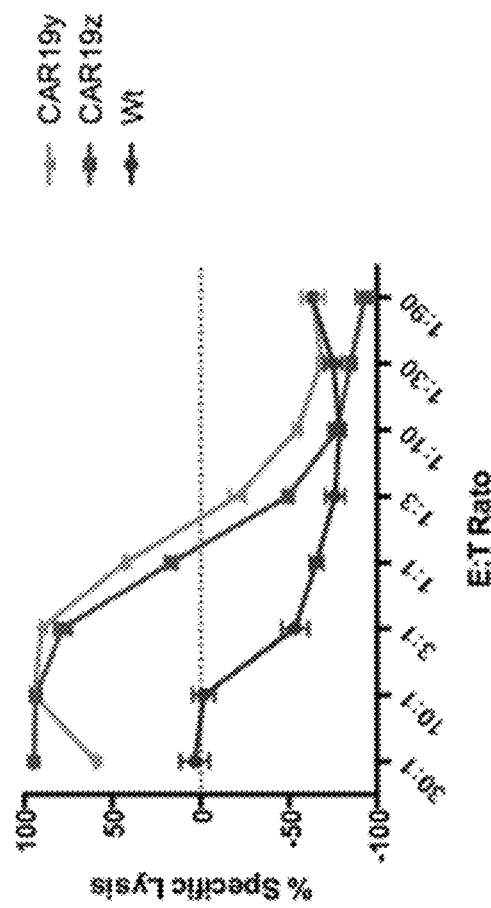
FIG. 7D is a graph showing that both CAR19ζ and CAR19γ THP1 macrophages, but not Wt THP1 macrophages, efficiently killed CD19+ tumor cells in an in vitro luciferase-based specific lysis assay after 24 hours of co-culture at various E:T ratios.

Both CAR19ζ and CAR19γ THP1 macrophages, but not Wt THP1 macrophages, efficiently killed CD19+ tumor cells in an in vitro luciferase-based specific lysis assay after 24 hours of co-culture at various E:T ratios (FIG. 7D).

As white blood cells of the innate immune system, macrophages respond to conserved molecular cues of infection, such as pathogen associated molecular patterns, via constitutively expressed pathogen recognition receptors. Toll-like receptors are the best characterized pathogen recognition receptors, and are known to activate macrophages.

Figure 8A:
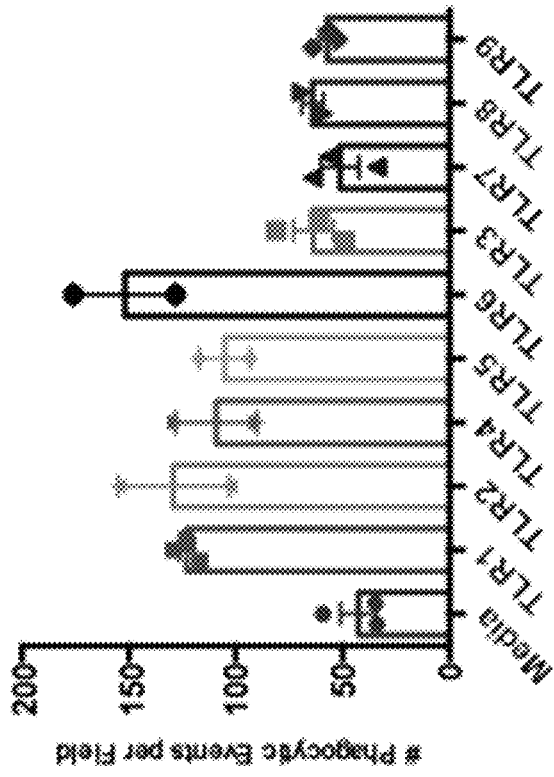
FIG. 8A is a graph showing macrophages responded to conserved molecular cues of infection, such as pathogen associated molecular patterns, via constitutively expressed pathogen recognition receptors.

To enhance the tumor phagocytic function of CARMA, in vitro phagocytosis assays were conducted using CAR macrophages that were primed with the ligands for TLR1-9, independently, or media control. Ligands for TLR1, 2, 4, 5, and 6 enhanced the phagocytic function of CARMA (FIG. 8A). This suggests that TLR ligands can be used to prime CARMA during the production process, or, TLR signaling domains can be encoded into the CAR construct to augment CAR signaling and downstream effector function as a novel second/subsequent generation CARMA construct.

Figure 8C:
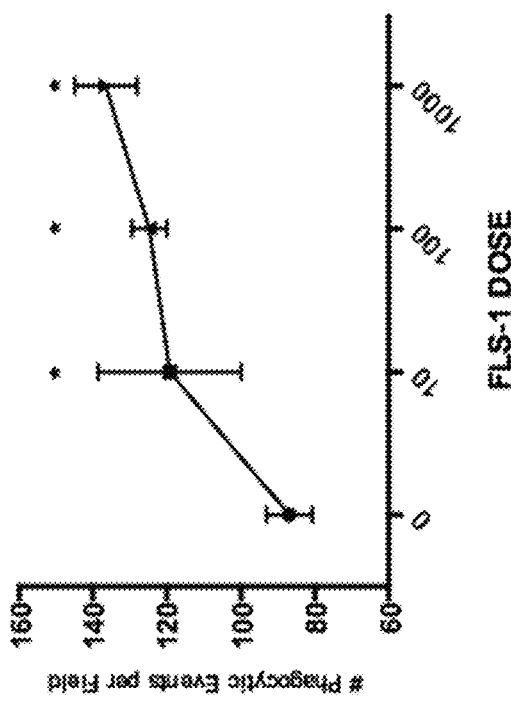
FIG. 8C is a graph showing the difference between TLR ligands that enhanced or did not enhance CARMA phagocytosis of tumor cells in a range of TLR3 or TLR6 ligand concentrations.
Figure 8B:
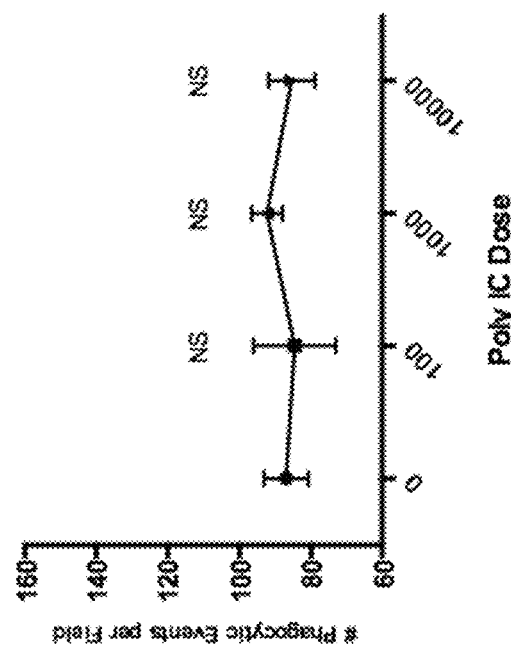
FIG. 8B is a graph showing an in vitro phagocytosis assay conducted using CAR macrophages that were primed with the ligands for TLR1-9, independently, or media control to enhance the tumor phagocytic function of CARMA. Ligands for TLR1, 2, 4, 5, and 6 enhanced the phagocytic function of CARMA.

FIGS. 8B and 8C demonstrate that the difference between TLR ligands that enhance or do not enhance CARMA phagocytosis of tumor cells holds true at a wide range of TLR3 or TLR6 ligand concentrations.

β-glucan, a yeast product, binds to Dectin-1 on the surface of macrophages and results in activation and effector function. In order to test the capacity of β-glucan to augment CARMA function, in vitro tumor phagocytosis assays were conducted in the absence of presence of 5 mcg/mL β-glucan. β-glucan enhanced the phagocytic capacity of CAR but not Wt macrophages (FIG. 9A).

Figures 9A, 9B:
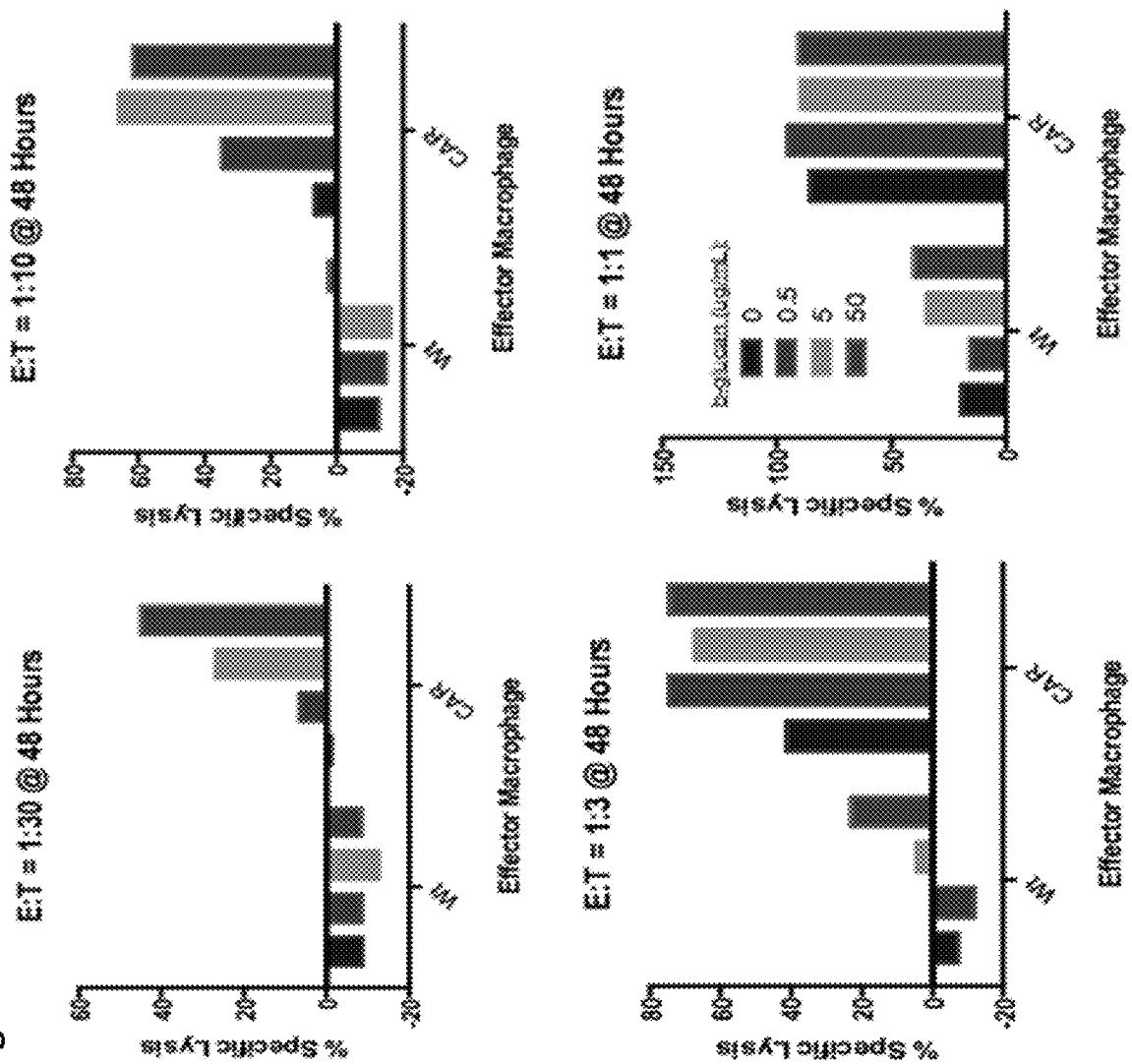
FIG. 9A is a graph showing β-glucan, a yeast product, bound to Dectin-1 on the surface of macrophages and resulted in activation and effector function. In order to test the capacity of β-glucan to augment CARMA function, in vitro tumor phagocytosis assays were conducted in the absence of presence of 5 mcg/mL β-glucan. β-glucan enhanced the phagocytic capacity of CAR, but not Wt, macrophages.
FIG. 9B is a series of graphs showing in vitro luciferase based specific lysis assays conducted at various effector (E):target (T) ratios in the presence of 0, 0.5, 5, of 50 μg/mL β-glucan to test the capacity of β-glucan to enhance CARMA tumor killing. β-glucan enhanced the specific lysis of antigen bearing tumor cells by CAR but not Wt THP-1 macrophages.

To test the capacity of β-glucan to enhance CARMA tumor killing, in vitro luciferase based specific lysis assays were conducted at various E:T ratios, in the presence of 0, 0.5, 5, of 50 mcg/mL β-glucan. β-glucan enhanced the specific lysis of antigen bearing tumor cells by CAR but not Wt THP-1 macrophages (FIG. 9B). These results indicate that β-glucan can be used as an adjuvant during the production process of CARMA, or, the Dectin-1 intracellular signaling domain can be encoded into the CAR transgene.

Given that β-glucan enhanced the function of CARMA, CAR constructs comprised of a Dectin-1 intracellular signaling domain were generated (FIG. 10A). These constructs were packaged into lentivirus and used to transduce THP-1 myeloid cells in a three-fold serial dilution of lentiviral titers. CAR was detected on the surface in both the CD8TM-Dectin1 CAR and DectinTM-Dectin1 CAR constructs (FIGS. 10B and 10C). Cells were sorted for 100% positivity and utilized for downstream in vitro functional experiments.

CD8TM-Dectin1 CAR and DectinTM-Dectin1 CAR macrophages were tested in an in vitro luciferase killing assay. Both constructs demonstrated specific lysis of tumor cells (10D).

Figure 10F:
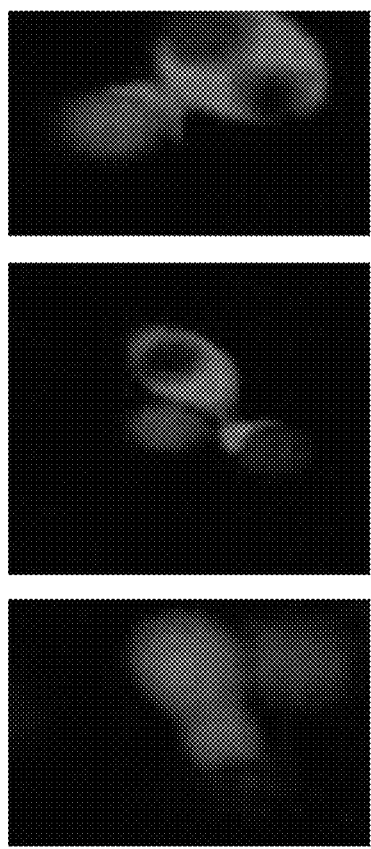
FIG. 10F is a series of images showing Dectin-1 CAR macrophages demonstrated the capacity for phagocytosis of multiple tumor cells.
Figure 10G:
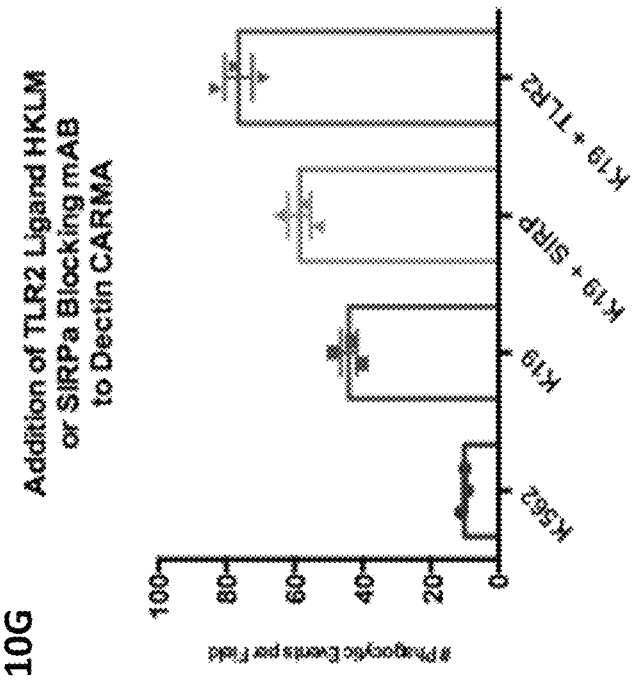
FIG. 10G is a graph showing an in vitro tumor phagocytosis assay. Dectin1-CAR macrophages demonstrated synergy with blockade of SIRPα, or with priming with a TLR ligand.
Figure 10E:
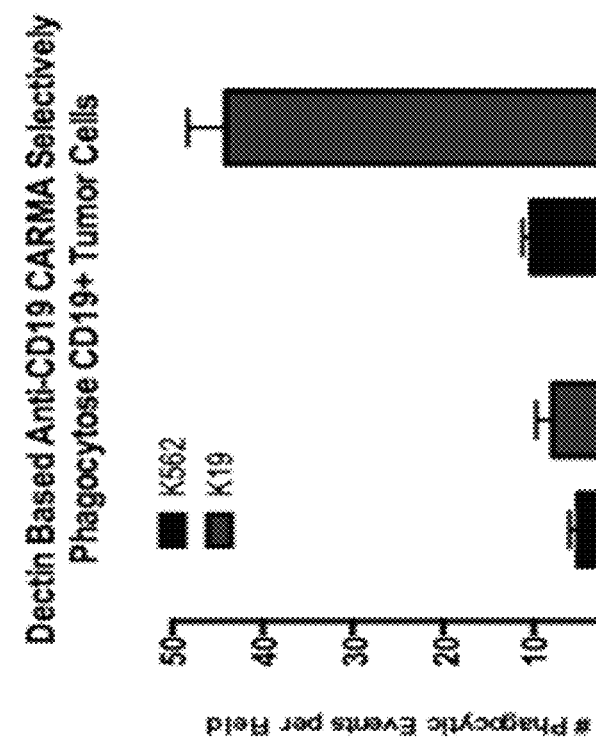
FIG. 10E is a graph showing Dectin1-CAR macrophages tested in an in vitro tumor phagocytosis assay against K562 (control) or K19 (target) tumor cells. Dectin1-CAR macrophages selectively phagocytosed cognate-antigen bearing tumor cells.

Dectin1-CAR macrophages were tested in an in vitro tumor phagocytosis assay against K562 (control) or K19 (target) tumor cells, and Dectin1-CAR macrophages selectively phagocytosed cognate-antigen bearing tumor cells (FIG. 10E). Dectin-1 CAR macrophages demonstrated the capacity for phagocytosis of multiple tumor cells (FIG. 10F).

In an in vitro tumor phagocytosis assay, Dectin1-CAR macrophages demonstrated synergy with blockade of SIRPα, or with priming with a TLR ligand (FIG. 10G).

Figure 11A:
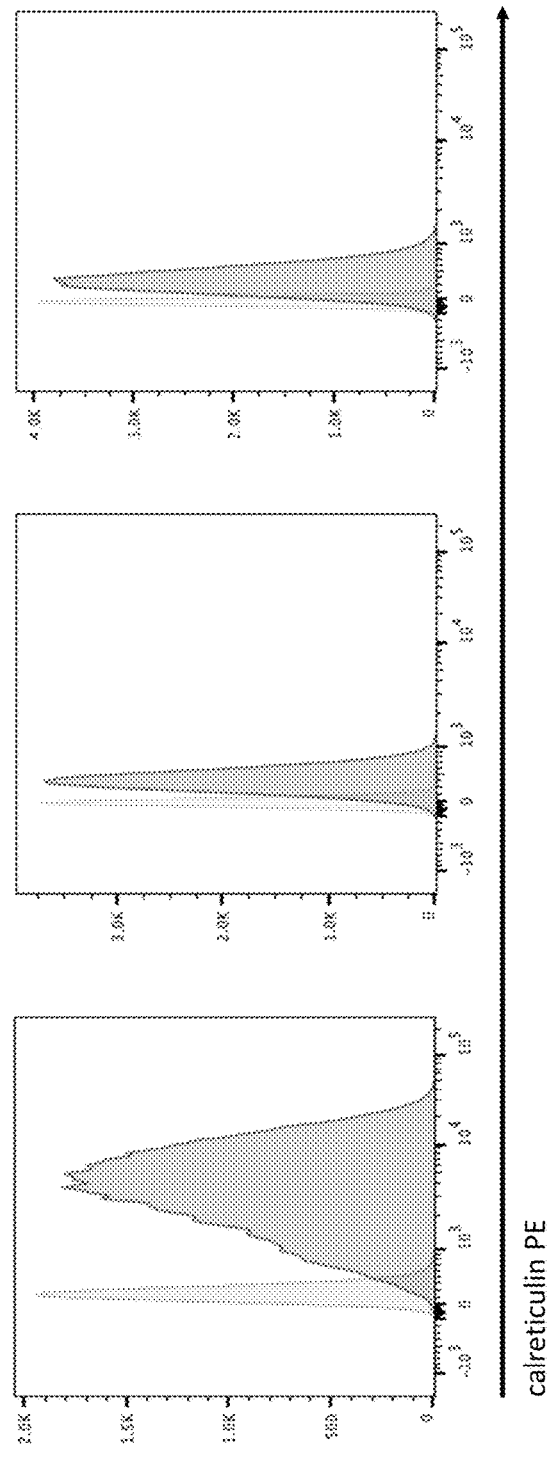
FIG. 11A is a series of graphs showing calreticulin levels in three different CD19+ target cell lines relative to isotype control.

FIG. 11A is a graph showing calreticulin levels in three different CD19+ target cell lines relative to isotype control. FIG. 11B is a graph showing the normalized mean fluorescent intensity of calreticulin expression in three different CD19+ target cell lines.

Figure 11C:
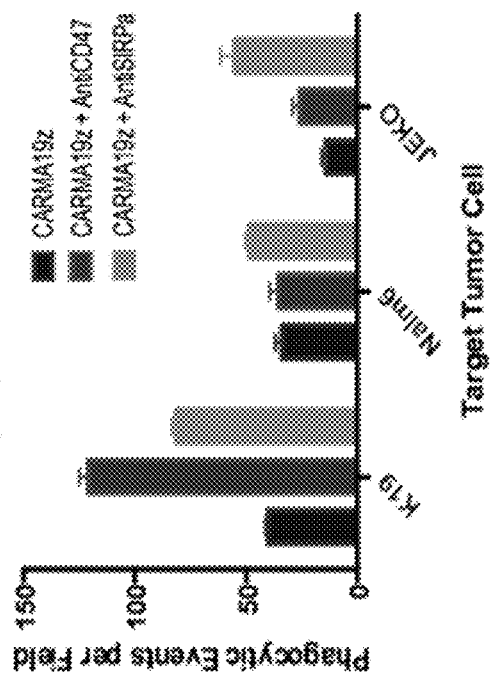
FIG. 11C is a graph showing that low levels of calreticulin moderately protected target cells, specifically Nalm6 and JEKO cell lines, from CAR19z macrophage phagocytosis. These data suggest that exploitation of calreticulin deposition/induction can be used an additional tactic to augment CARMA effector function.
Figure 11B:
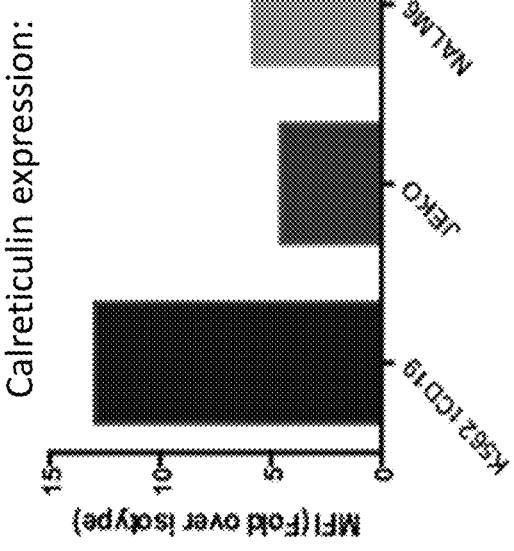
FIG. 11B is a graph showing the normalized mean fluorescent intensity of calreticulin expression in three different CD19+ target cell lines.

FIG. 11C is a graph showing that low levels of calreticulin moderately protected target cells, specifically Nalm6 and JEKO cell lines, from CAR19z macrophage phagocytosis. These data suggest that exploitation of calreticulin deposition/induction can be used an additional tactic to augment CARMA effector function.

Figure 12B:
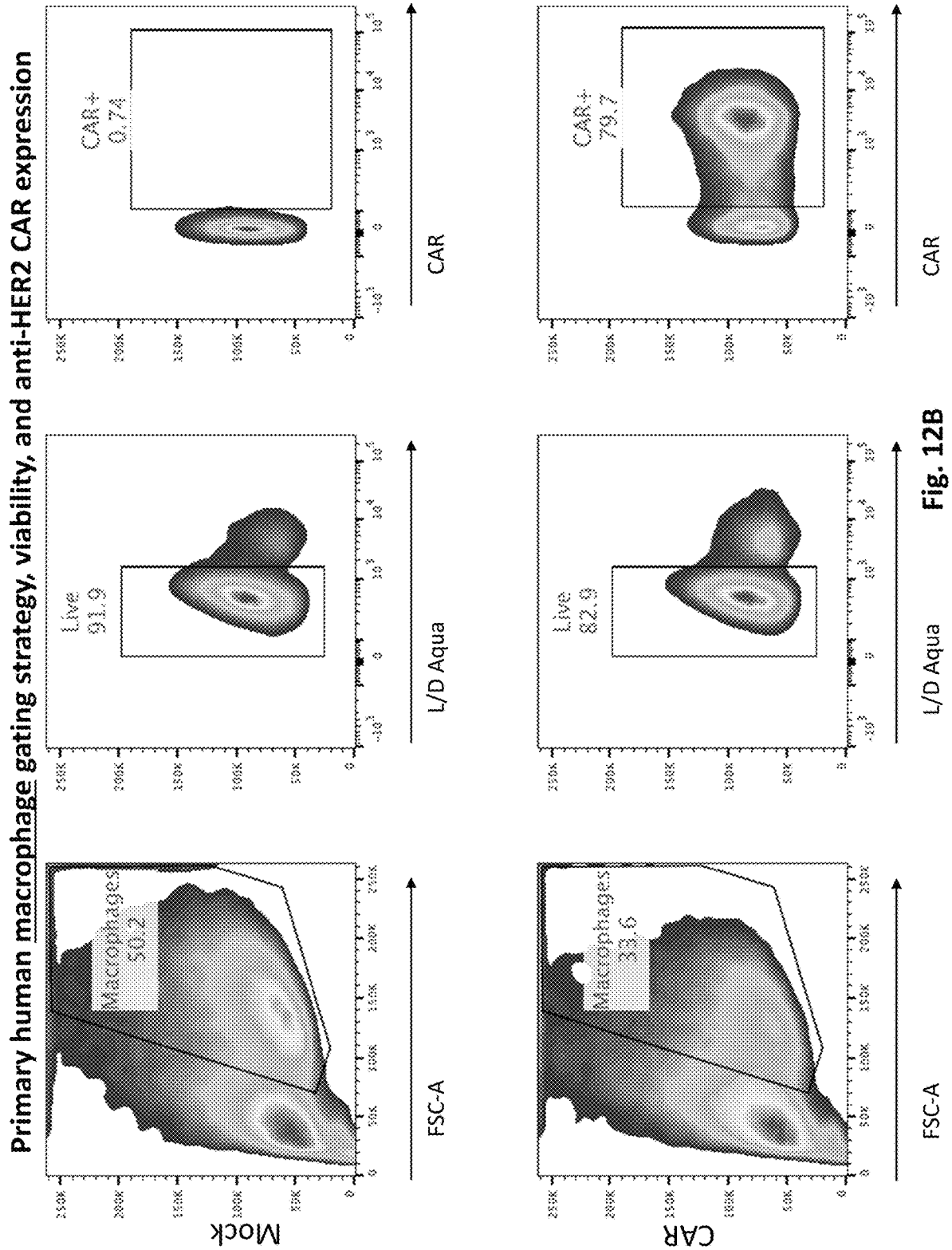
FIG. 12B is a series of graphs showing the efficiency of anti-HER2 CAR mRNA electroporation into primary human monocyte derived macrophages (fully differentiated) at 79.7%.

To validate and test the function of CAR in primary human monocyte derived macrophages, several gene delivery approaches were tested. In FIG. 12A, anti-HER2 CAR constructs were cloned into mRNA expression plasmids, transcribed in vitro, and the mRNA was directly electroporated into primary human monocytes. FIG. 13A demonstrates the gating strategy, viability, and 84.3% transfection efficiency relative to mock electroporated cells. FIG. 12B demonstrates the efficiency of anti-HER2 CAR mRNA electroporation into primary human monocyte derived macrophages (fully differentiated) at 79.7%.

Figure 12C:
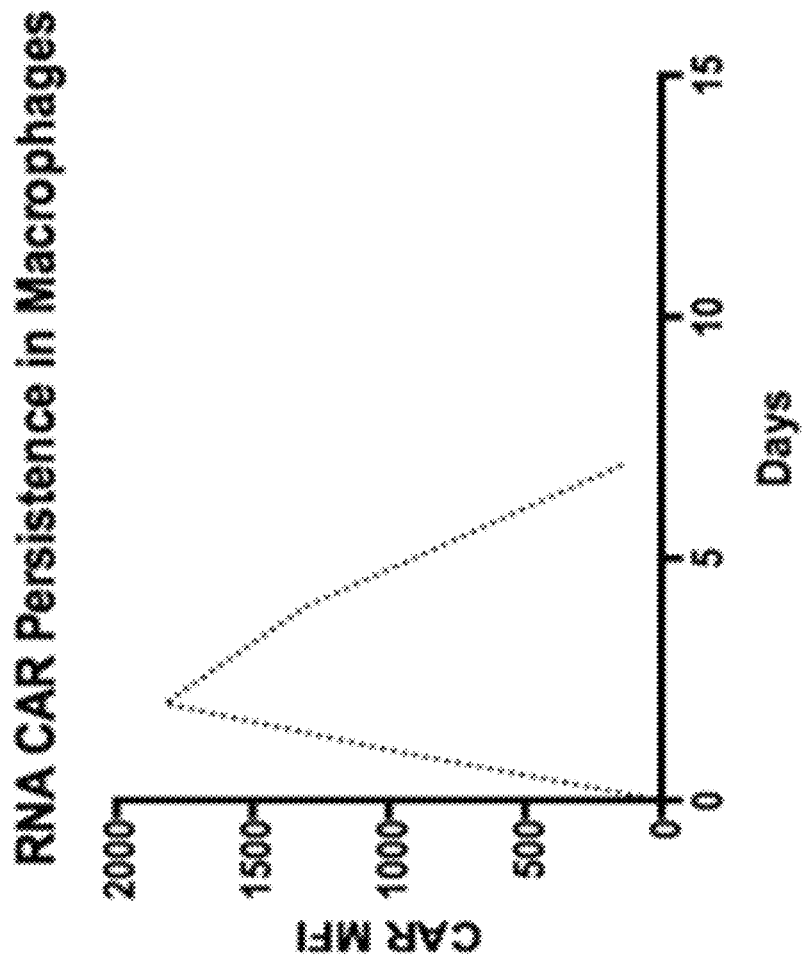
FIG. 12C is a graph showing that while mRNA electroporation results in a high CAR transfection efficiency of both monocytes and macrophages, CAR expression was temporary due to mRNA degradation, peaking at day 2 and disappearing by day 7 post electroporation in vitro.

FIG. 12C is a graph demonstrating that while mRNA electroporation results in a high CAR transfection efficiency of both monocytes and macrophages, CAR expression is temporary due to mRNA degradation, peaking at day 2 and disappearing by day 7 post electroporation in vitro.

NSGS mice were injected with 1E6 SKOV3 CBG/GFP+ human ovarian cancer cells via IP injection, a model of metastatic intraperitoneal carcinomatosis of HER2+ ovarian cancer. Mice were co-injected with either mock electroporated or anti-HER2 CAR mRNA electroporated primary human monocytes or primary human macrophages (1:1 E:T ratio) and tumor burden was imaged. CAR macrophages (FIG. 13A) and CAR monocytes (FIG. 13B) demonstrated marginal reduction in tumor growth over approximately two weeks. The first time point at which tumor burden was bioluminescently quantified was 24 hours post-treatment, demonstrating that CAR monocytes and macrophages had activity in the first 24 hours.

Figure 14A:
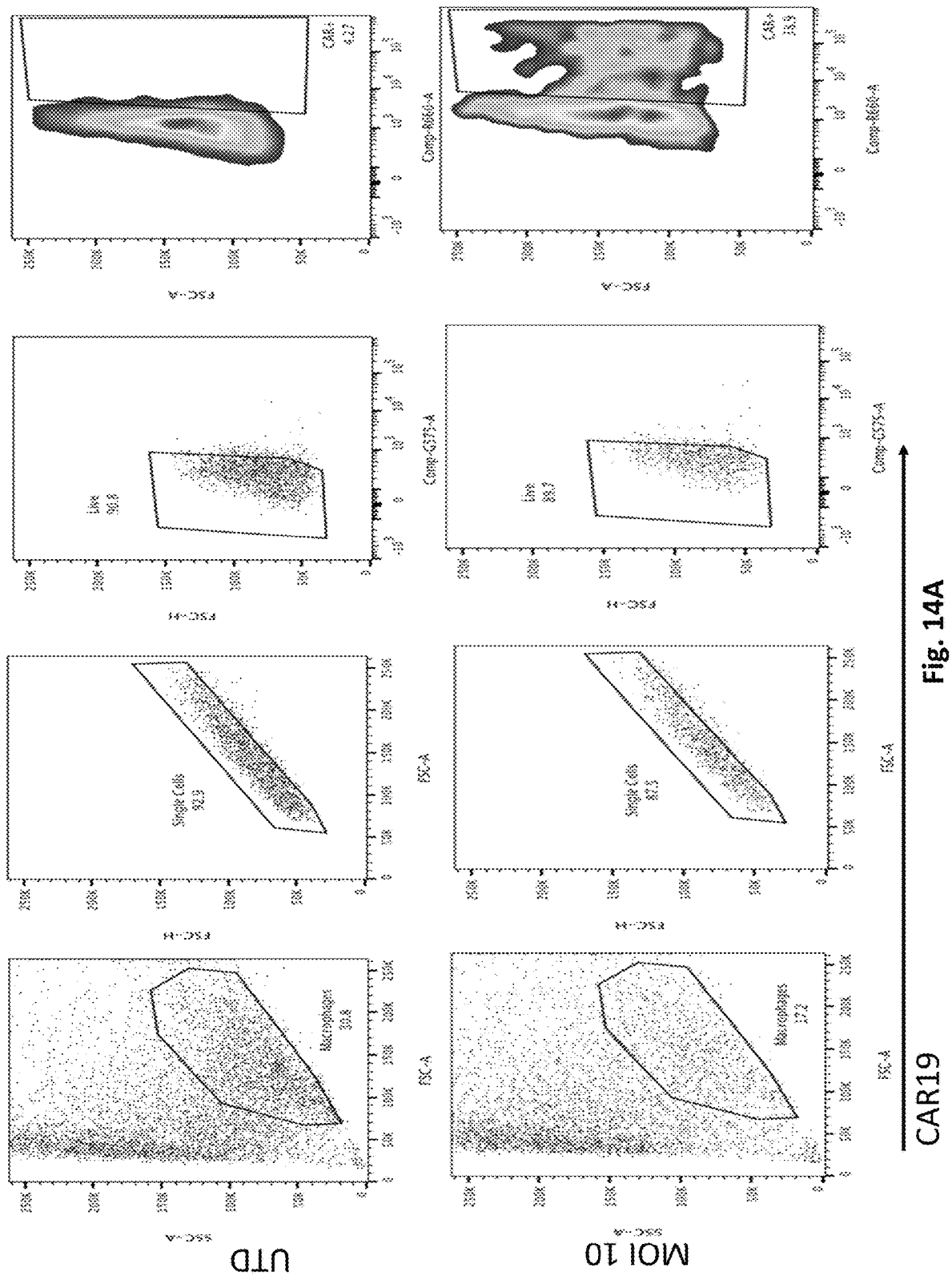
FIG. 14A is a series of graphs showing lentiviral delivery of CAR transgenes to primary human monocyte derived macrophages was tested using multiple CAR constructs. CAR19 was delivered to human macrophages via lentiviral transduction, demonstrating a 4.27% and 38.9% transduction efficiency in the control vs. CAR19 lentivirus (MOI 10) groups, respectively.

Lentiviral delivery of CAR transgenes to primary human monocyte derived macrophages was tested using multiple CAR constructs. In FIG. 14A, CAR19 was delivered to human macrophages via lentiviral transduction, demonstrating a 4.27% and 38.9% transduction efficiency in the control vs. CAR19 lentivirus (MOI 10) groups, respectively. The FACS gating strategy is shown.

Figure 14B:
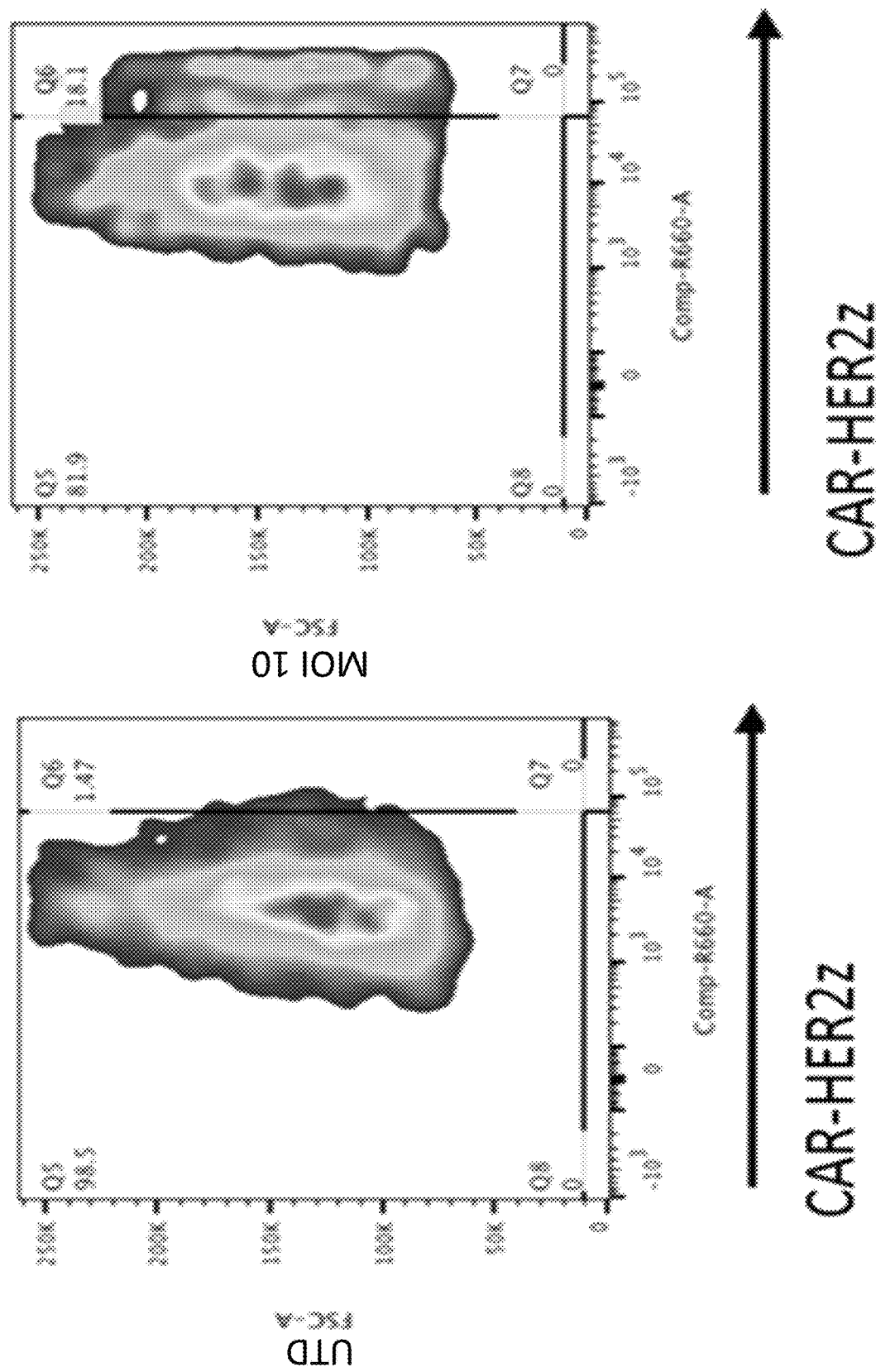
FIG. 14B is a series of representative FACS plots showing the expression of anti-HER2 CAR in primary human macrophages, with a 1.47 and 18.1% transduction efficiency between the control and MOI 10 CAR LV conditions, respectively.

FIG. 14B is a representative FACS plot showing the expression of anti-HER2 CAR in primary human macrophages, with a 1.47 and 18.1% transduction efficiency between the control and MOI 10 CAR LV conditions, respectively.

Figure 15A:
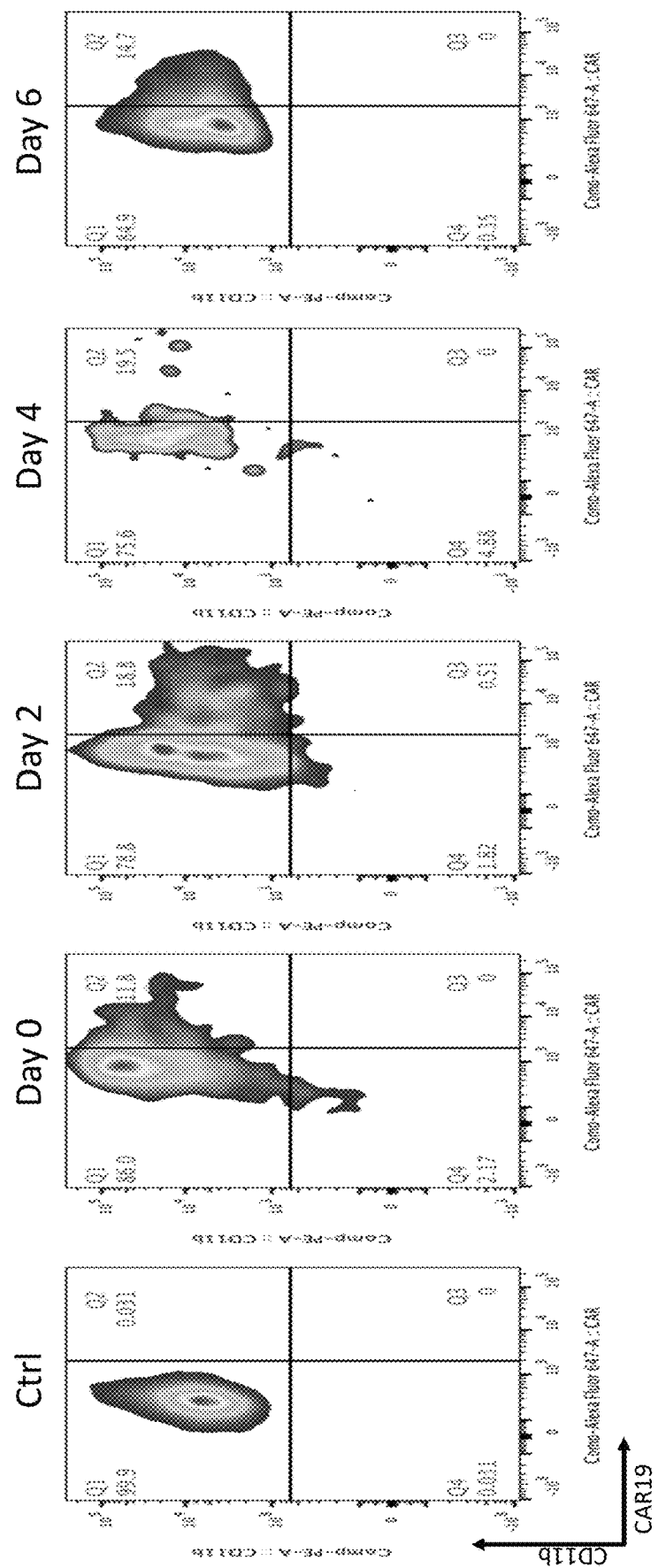
FIG. 15A is a series of graphs showing transduction efficiency peaked at the midpoint of transduction (day 4), for anti-CD19. Monocyte derived macrophages were generated by differentiating CD14+ selected cells (from normal donor apheresis products) in GM-CSF conditioned media for 7 days. To optimize delivery of CAR via lentiviral transduction, anti-CD19 lentivirus was used to transduce macrophages at different points of the monocyte to macrophage differentiation process.

Monocyte derived macrophages were generated by differentiating CD14+ selected cells (from normal donor apheresis products) in GM-CSF conditioned media for 7 days. To optimize delivery of CAR via lentiviral transduction, anti-CD19 and anti-HER2 lentiviruses were used to transduce macrophages at different points of the monocyte to macrophage differentiation process. Transduction efficiency peaked at the midpoint of transduction (day 4), for both anti-CD19 and anti-HER2 CAR constructs (FIGS. 15A and 15B). Anti-CD19 CAR primary human macrophages were used in an in vitro FACS based phagocytosis assay against CD19+ GFP+K562 tumor cells, with CD11b+/GFP+ events being defined as phagocytic events. Macrophages transduced at different time points as in FIG. 15A were used in this assay. FIG. 15C demonstrates that the efficacy of phagocytosis trended with the CAR transduction efficiency, peaking with macrophages transduced at day 4 during the differentiation process.

Alternative transduction approaches to delivering transgenes to primary human macrophages were tested, given that mRNA electroporation was transient and lentivirus was only moderately efficient and required high titer. Adenovirus (recombinant, replication deficient) was identified as an efficient approach to primary human macrophage transduction. Expression of Coxackie Adenovirus Receptor (the docking protein for Ad5) and CD46 (the docking protein for Ad35) were tested relative to isotype control on primary human macrophages, and CD46 but not Coxackie Adenovirus receptor was highly expressed (FIG. 16A). Thus, chimeric Ad5f35 adenovirus was utilized for primary human macrophage transduction, and was engineered via standard molecular biology techniques to express a chimeric antigen receptor (GFP and empty Ad5f35 viruses were used as controls) against HER2.

FIG. 16B shows that at an MOI of 1000, Ad5f35 effectively delivered a transgene (GFP was used as a model transgene) into human macrophages, and expression went up over time as monitored by GFP signal quantification on an IVIS Spectrum. FIG. 16C compares the transduction kinetics of primary human macrophages at different timepoints across a broad range of MOIs—up to 10,000.

FIG. 16C shows representative FACS plots of anti-HER2 CAR expression on Ad5f35 transduced human macrophages 48 hours post transduction, at a broad range of viral MOIs.

Figure 16D:
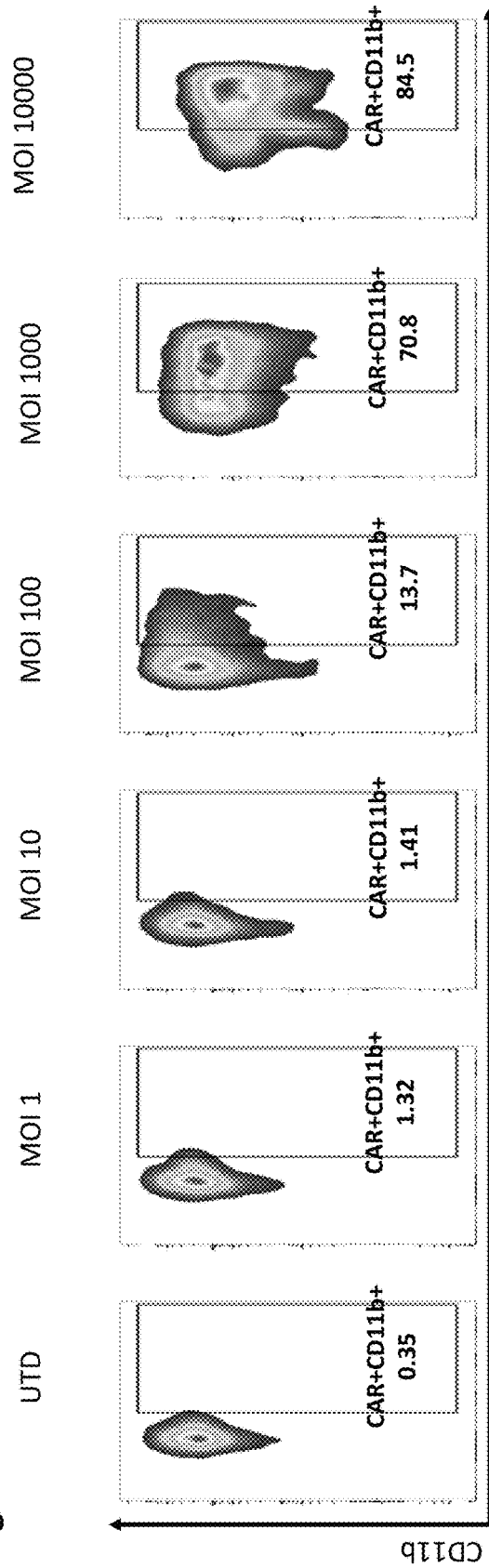
FIG. 16D is a series of representative FACS plots of anti-HER2 CAR expression on Ad5f35 transduced human macrophages at 48 hours post transduction, at a broad range of viral MOIs.
Figure 16E:
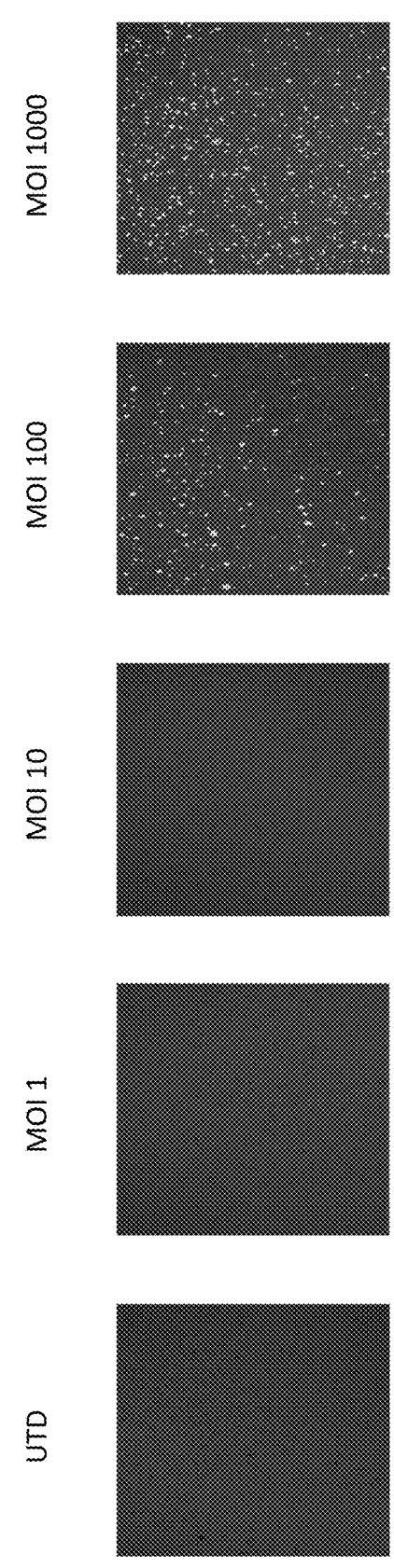
FIG. 16E is a series of representative fluorescent microscopy images of Ad5f35-GFP transduced primary human macrophages, with the highest transduction efficiency demonstrated at an MOI of 1000.

FIG. 16D shows representative fluorescent microscopy images of Ad5f35-GFP transduced primary human macrophages, with the highest transduction efficiency demonstrated at an MOI of 1000.

Figure 17A:
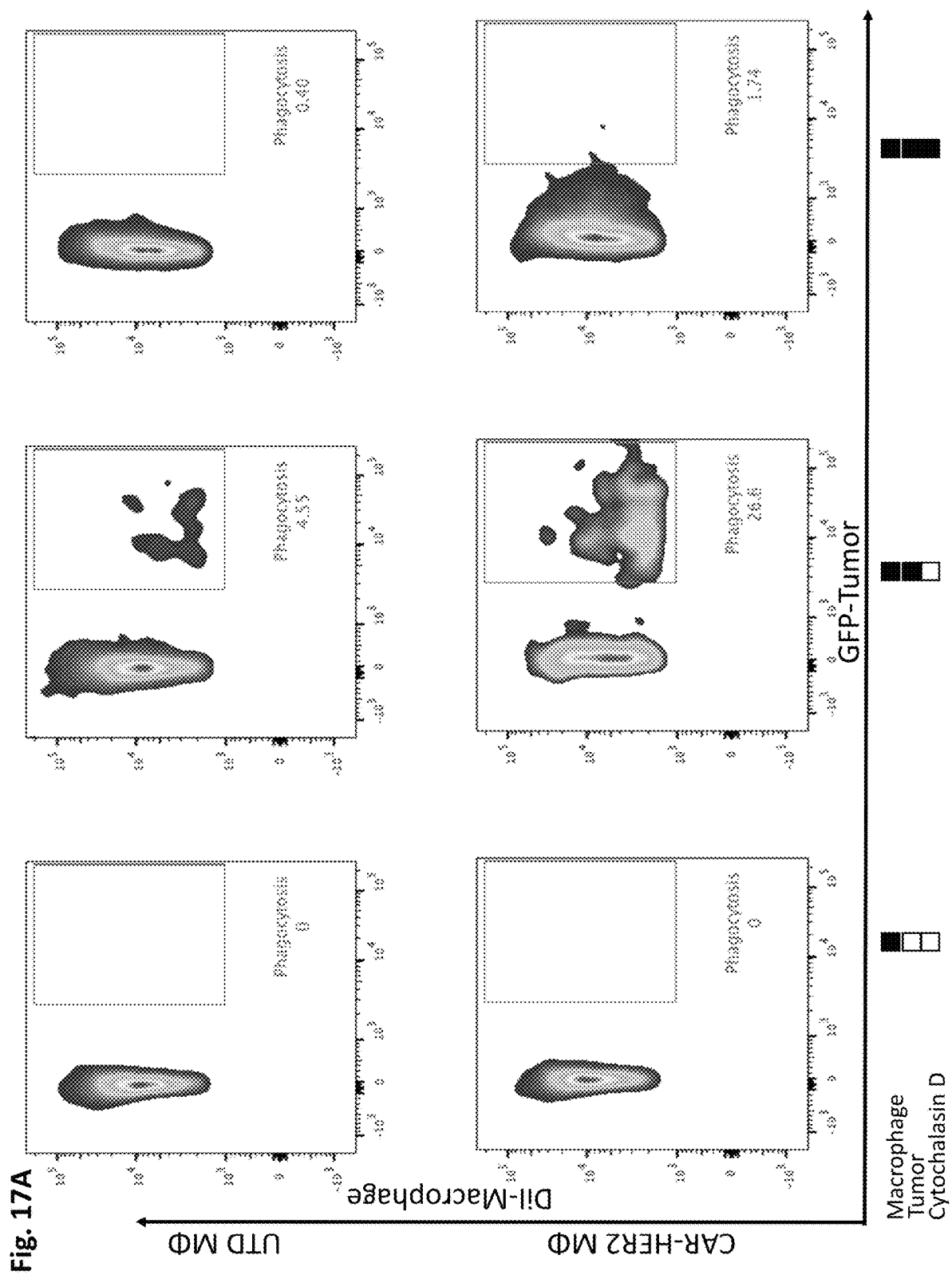
FIG. 17A is a series of graphs showing primary human CARMA tested in an in vitro phagocytosis assay via FACS analysis. Macrophages (untransduced or anti-HER2 CAR) were stained with DiI prior to co-culture with GFP+ SKOV3 ovarian cancer cells. Phagocytosis, defined by DiI/GFP double positive events, was measured at a level of 26.6% in the CAR group and 4.55% in the control group.
Figure 17C:
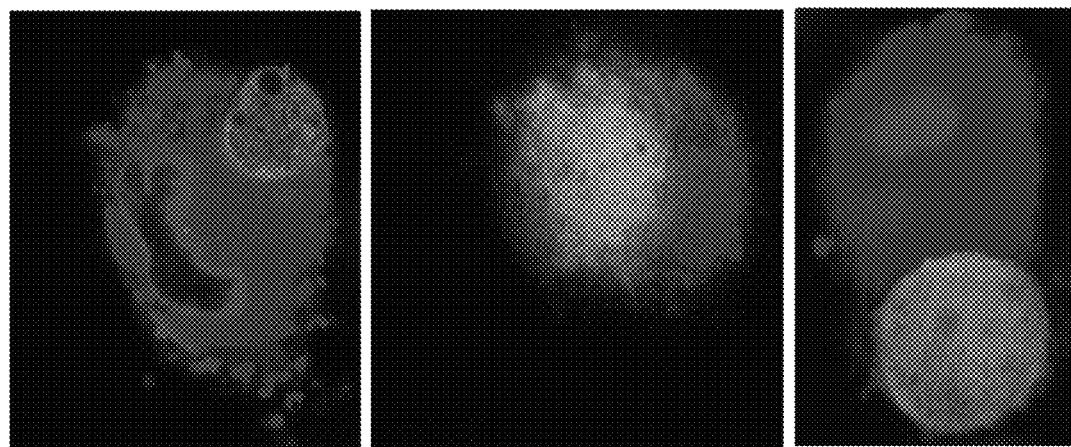
FIG. 17C is a series of images showing confocal microscope images of DiI stained CAR-HER2 macrophages co-cultured with SKOV3-GFP.
Figure 17B:
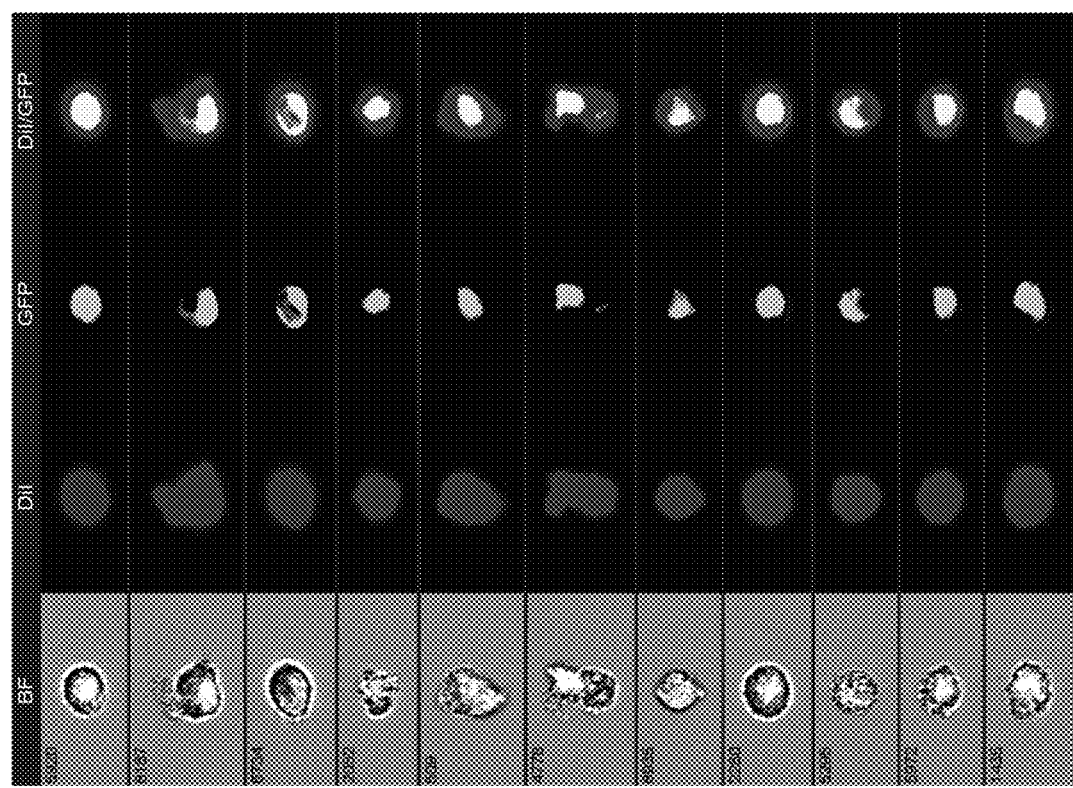
FIG. 17B is a series of images demonstrating visually that these double positive events represent phagocytosis. To validate that the DiI/GFP double positive events were phagocytic events and not doublets, cytochalasin D (a phagocytosis inhibitor) was added to an arm of the experiment, and fully abrogated CAR mediated phagocytosis down to 1.74%. To further validate that primary human CAR macrophages could phagocytose tumor cells, double positive events were gated by Amnis Imagestream FACS and ordered from high to low by the Amnis phagocytosis-erode algorithm.

Primary human CARMA were tested in an in vitro phagocytosis assay via FACS analysis. Macrophages (untransduced or anti-HER2 CAR) were stained with DiI prior to co-culture with GFP+ SKOV3 ovarian cancer cells. Phagocytosis, defined by DiI/GFP double positive events, was measured at a level of 26.6% in the CAR group and 4.55% in the control group (FIG. 17A). To validate that the DiI/GFP double positive events were phagocytic events and not doublets, cytochalasin D (a phagocytosis inhibitor) was added to an arm of the experiment, and fully abrogated CAR mediated phagocytosis down to 1.74%. To further validate that primary human CAR macrophages could phagocytose tumor cells, double positive events were gated by Amnis Imagestream FACS and ordered from high to low by the Amnis phagocytosis-erode algorithm, demonstrating visually that these double positive events represent phagocytosis (FIG. 17B). In addition, DiI stained CAR-HER2 macrophages were co-cultured with SKOV3-GFP and imaged by confocal microscope and phagocytosis was verified.

Figure 18:
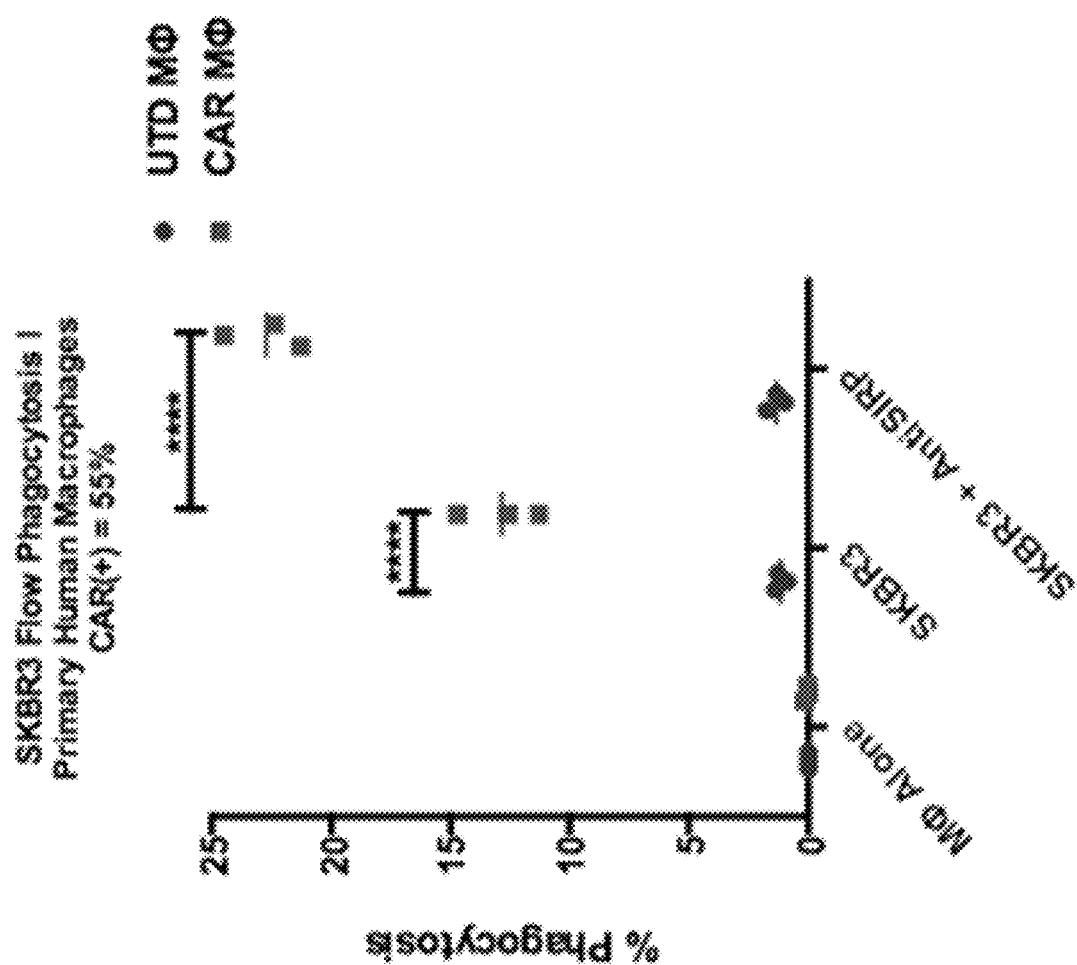
FIG. 18 is a graph showing CAR, but not UTD, human macrophages phagocytosed breast cancer cells. Anti-HER2 CAR primary human macrophages generated using Ad5f35-CAR transduction of monocyte derived macrophages. These cells (or control untransduced cells) were utilized as effectors in an in vitro FACS based phagocytosis assay of SKBR3 human breast cancer cells. In addition, addition of anti-SIRPα monoclonal antibody enhanced CARMA but not UTD macrophage phagocytosis of breast cancer cells. These results demonstrate that the synergy between blockade of the CD47/SIRPα axis seen with CARMA in the THP-1 model translates to primary human macrophage studies.

Anti-HER2 CAR primary human macrophages were generated using Ad5f35-CAR transduction of monocyte derived macrophages. These cells (or control untransduced cells) were utilized as effectors in an in vitro FACS based phagocytosis assay of SKBR3 human breast cancer cells. FIG. 18 demonstrates that CAR but not UTD human macrophages phagocytose breast cancer cells. In addition, addition of anti-SIRPα monoclonal antibody enhanced CARMA but not UTD macrophage phagocytosis of breast cancer cells. These results demonstrate that the synergy between blockade of the CD47/SIRPα axis seen with CARMA in the THP-1 model translates to primary human macrophage studies.

Figure 19:
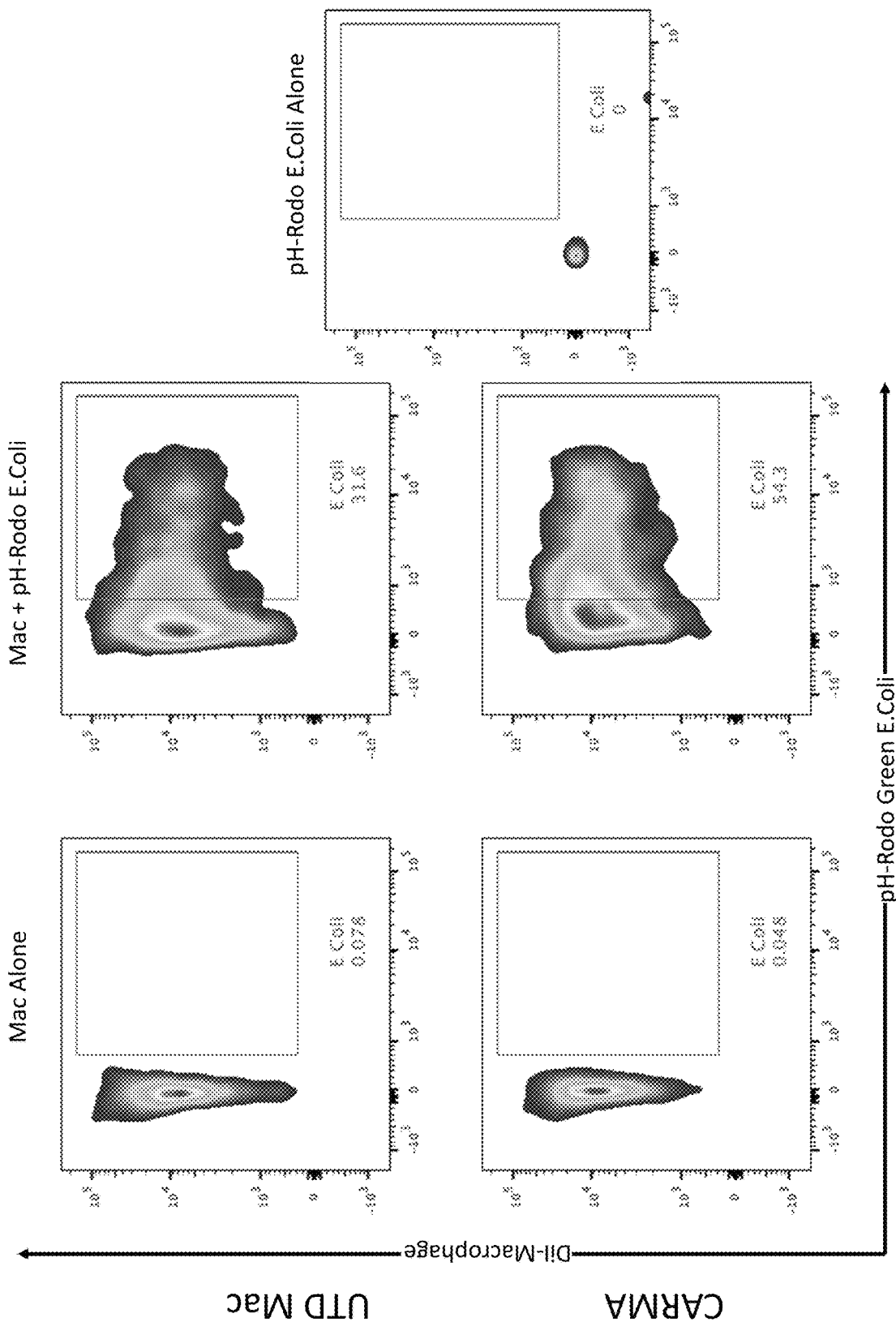
FIG. 19 is a series of representative FACS plot showing that CARMA exhibit intact phagocytosis of pH-Rodo Green $E.$ $coli$ particles. In order to demonstrate that CAR macrophages were still functional innate immune cells in the anti-microbial sense, and did not lose the capacity to respond to infectious stimuli, control untransduced or CAR macrophages were employed in a FACS based $E.$ $coli$ phagocytosis assay.

Macrophages are white blood cells of the innate immune system and thus have sentinel anti-microbial properties. In order to demonstrate that CAR macrophages are still functional innate immune cells in the anti-microbial sense, and do not lose the capacity to respond to infectious stimuli, control untransduced or CAR macrophages were employed in a FACS based E. coli phagocytosis assay. FIG. 19 is a representative FACS plot showing that CARMA exhibit intact phagocytosis of pH-Rodo Green E. coli particles.

Figure 20C:
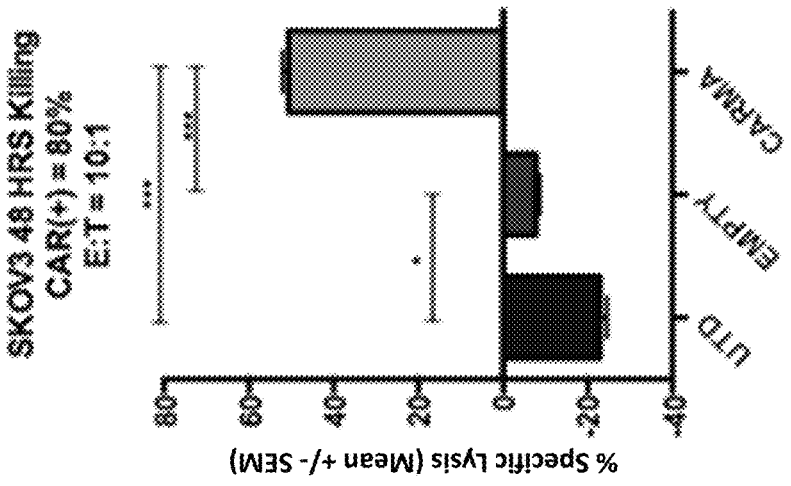
FIG. 20C is a graph showing in vitro luciferase based killing assay utilizing SKOV3 ovarian cancer cells as targets. CARMA, but not control UTD or control Empty Ad5f35 transduced macrophages, had significant anti-tumor activity against both models after 48 hours of co-culture.
Figure 20B:
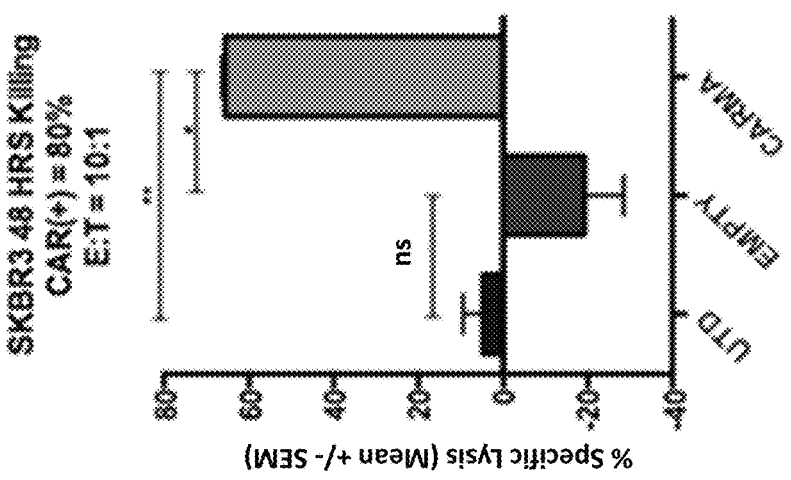
FIG. 20B is a graph showing in vitro luciferase based killing assay utilizing SKBR3 breast cancer cells as targets. CARMA, but not control UTD or control Empty Ad5f35 transduced macrophages, had significant anti-tumor activity against both models after 48 hours of co-culture.
Figure 20A:
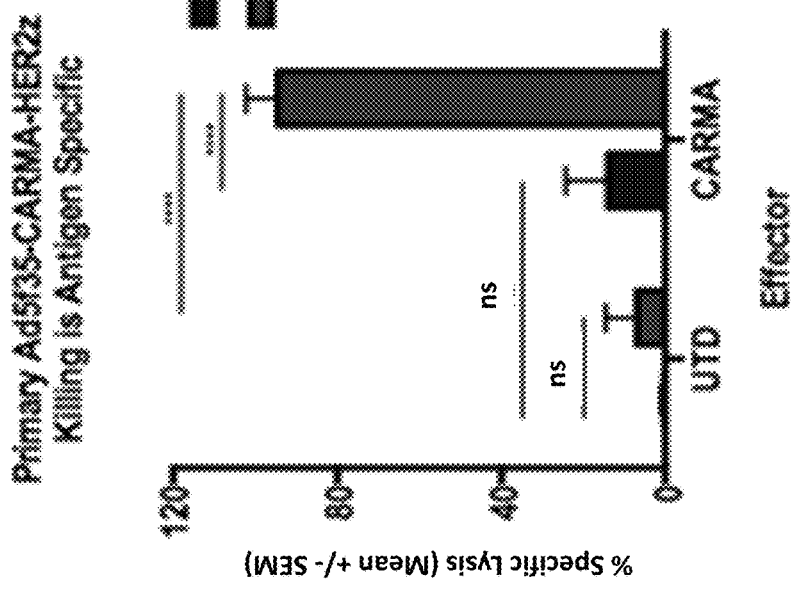
FIG. 20A is a graph showing primary human anti-HER2 CARMA tested as effector cells in in vitro luciferase based killing assays. Anti-HER2 CARMA, but not control UTD macrophages, led to the specific lysis of HER2+K562 cells but not control K562 cells, lacking HER2 expression, after 48 hours of co-culture.
Figure 20D:
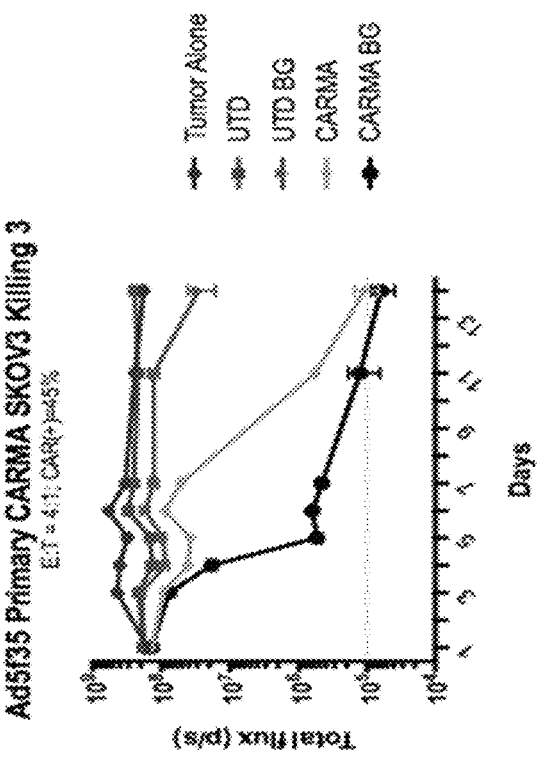
FIG. 20D is a graph showing the synergy between blockade of the CD47/SIRPα axis in a killing assay. SKOV3 ovarian cancer cells were co-cultured with media, control untransduced macrophages, anti-HER2 CARMA, anti-HER2 CARMA+antiCD47 mAB (10 mcg/mL), or anti-HER2 CARMA+anti-SIRPα (10 mcg/mL) and luciferase signal was serially measured. CARMA led to complete tumor eradication by day 13, while the kinetics of tumor eradication were even faster in the presence of blocking the CD47/SIRPα axis.
Figure 20E:
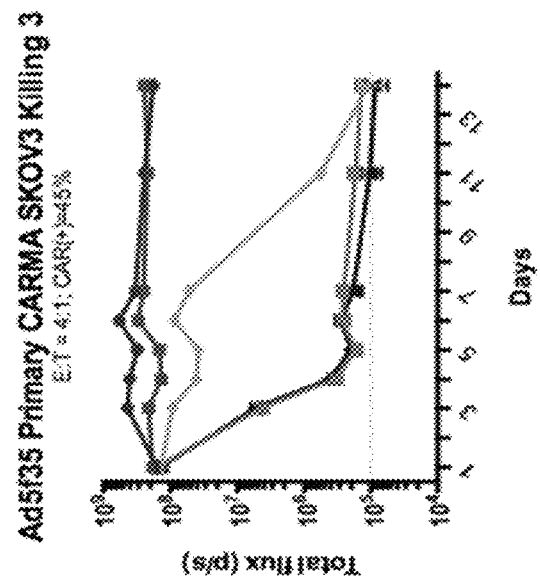
FIG. 20E is a graph showing the synergy with β-glucan, which was demonstrated in a THP-1 macrophage CARMA model, and β-glucan priming of the CARMA led to enhanced tumor killing kinetics.
Figure 20F:
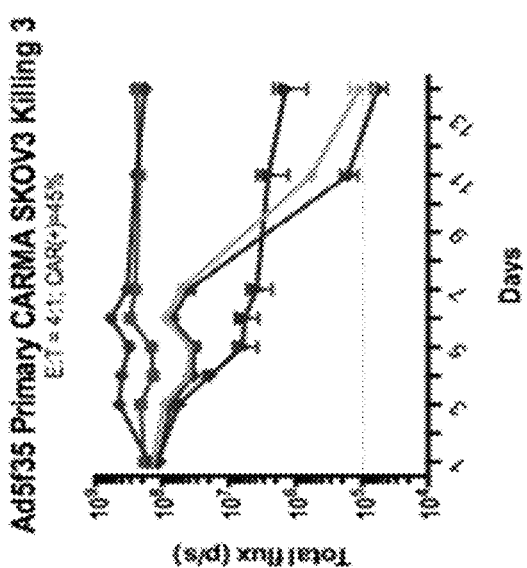
FIG. 20F is a graph showing that exposure of CARMA to LPS (a TLR-4 ligand) or Poly-IC (a TLR-3 ligand) led to modulation of the anti-tumor effect.

Primary human anti-HER2 CARMA were tested as effector cells in in vitro luciferase based killing assays. Anti-HER2 CARMA, but not control UTD macrophages, led to the specific lysis of HER2+K562 cells but not control K562 cells, lacking HER2 expression, after 48 hours of co-culture (FIG. 20A). To demonstrate that CARMA killing can be translated to tumor cells expressing HER2 at physiologic levels (as opposed to K562-HER2 which is lentivirally transduced to overexpress HER2), SKBR3 breast cancer cells and SKOV3 ovarian cancer cells were used as targets. CARMA, but not control UTD or control Empty Ad5f35 transduced macrophages, had significant anti-tumor activity against both models after 48 hours of co-culture (FIGS. 20B and 20C). In order to test synergy between blockade of the CD47/SIRPα axis in a killing assay, SKOV3 ovarian cancer cells were co-cultured with media, control untransduced macrophages, anti-HER2 CARMA, anti-HER2 CARMA+ antiCD47 mAB (10 mcg/mL), or anti-HER2 CARMA+anti-SIRPα (10 mcg/mL) and luciferase signal was serially measured. CARMA led to complete tumor eradication by day 13, while the kinetics of tumor eradication were even faster in the presence of blocking the CD47/SIRPα axis (FIG. 20D). Synergy with β-glucan, which was demonstrated in a THP-1 macrophage CARMA model, was tested in a similar experiment, and β-glucan priming of the CARMA led to enhanced tumor killing kinetics (FIG. 20E). Exposure of CARMA to LPS (a TLR-4 ligand) or Poly-IC (a TLR-3 ligand) led to modulation of the anti-tumor effect (FIG. 20F).

Figure 21:
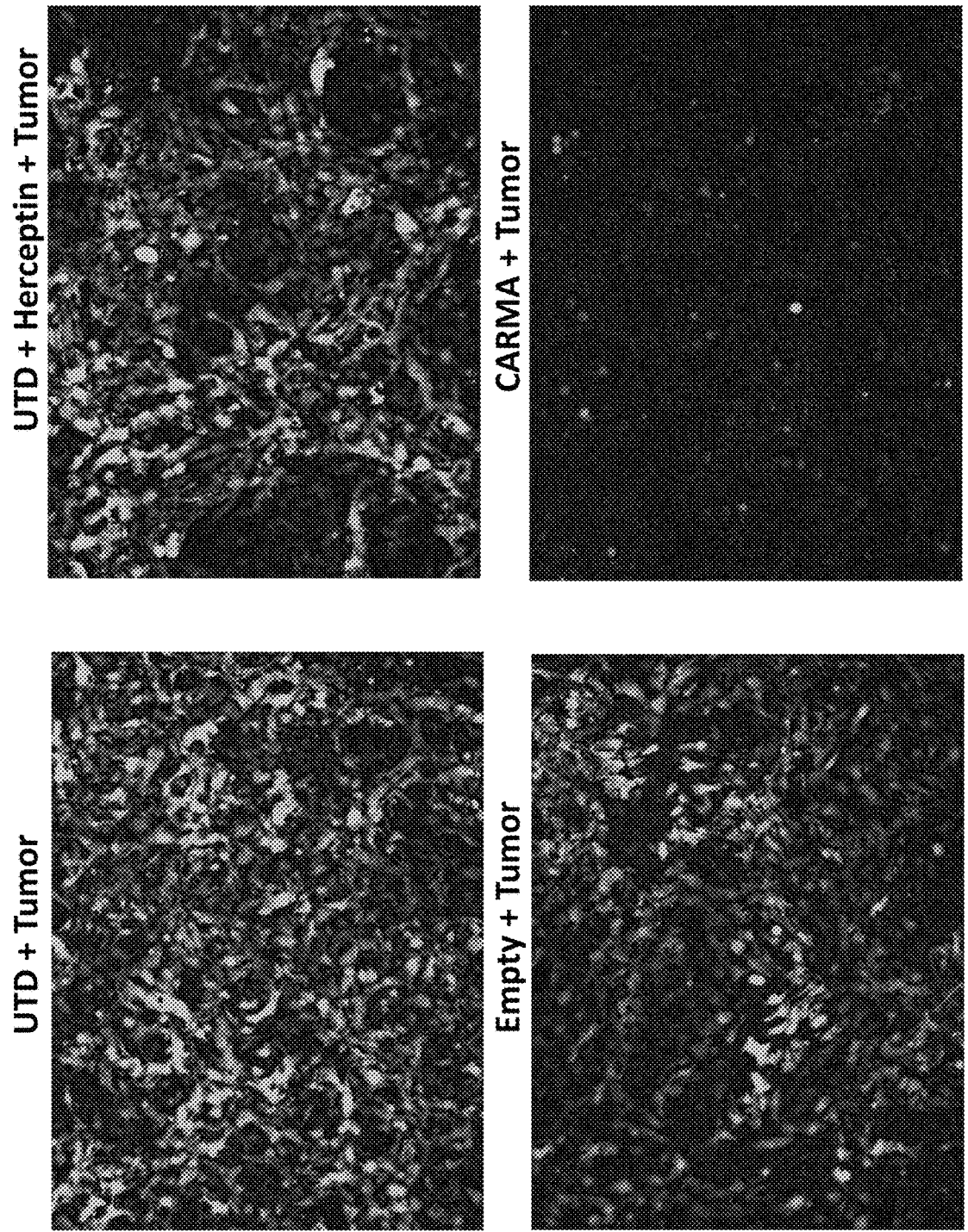
FIG. 21 is a series of images showing the capacity for primary human CARMA to clear tumors in an in vitro luciferase assay. GFP+ SKOV3 ovarian cancer cells were co-cultured with control UTD macrophages, control UTD macrophages plus 10 mcg/mL trastuzumab, control empty Ad5f35 virus transduced macrophages, or anti-HER2 primary human CARMA. CARMA, but not the control conditions, were capable of clearing the tumor cells.

The capacity for primary human CARMA to clear tumors in vitro was demonstrated by luciferase assay in FIGS. 20A-20F. To validate these results, GFP+ SKOV3 ovarian cancer cells were co-cultured with control UTD macrophages, control UTD macrophages plus 10 mcg/mL trastuzumab, control empty Ad5f35 virus transduced macrophages, or anti-HER2 primary human CARMA. CARMA, but not the control conditions, were capable of clearing the tumor cells (FIG. 21).

Figure 22A:
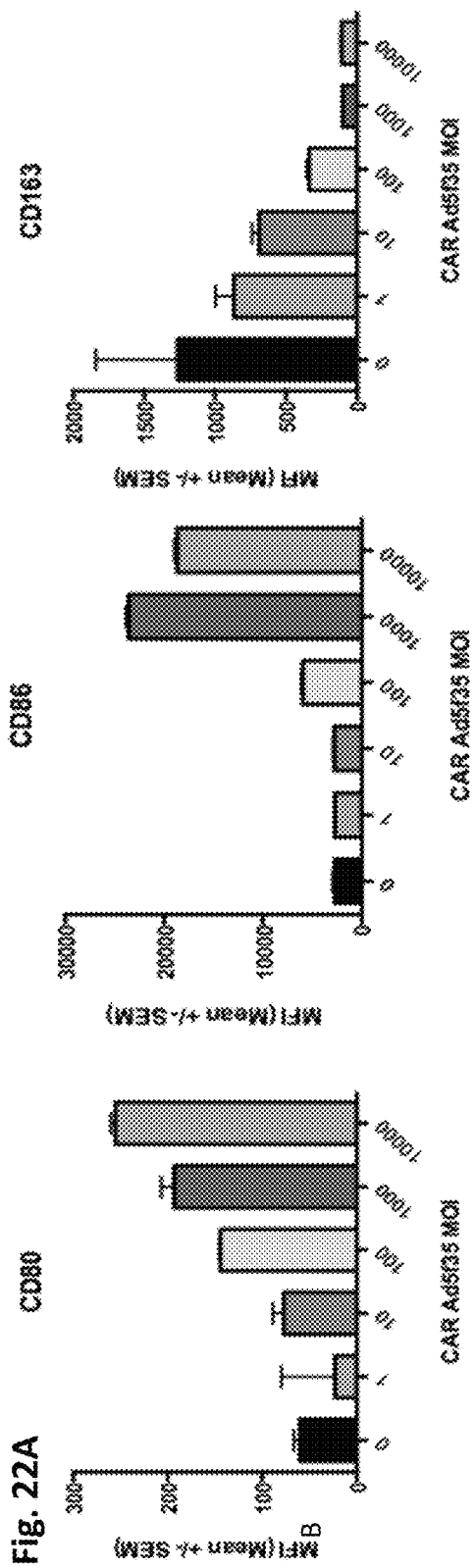
FIG. 22A is a panel of graphs showing a dose dependent up-regulation of M1 markers CD80/CD86, and a dose dependent down-regulation of M2 marker CD163, were measured by FACS. Macrophages are phenotypically plastic cells capable of adopting diverse functional features, commonly separated into the M1 and M2 macrophage classifications—with M1 being inflammatory/activated, and M2 being immunosuppressive/tumor-promoting. M1 and M2 markers were measured 48 hours after transduction of primary human macrophages with Ad5f35 CAR virus.
Figure 22B:
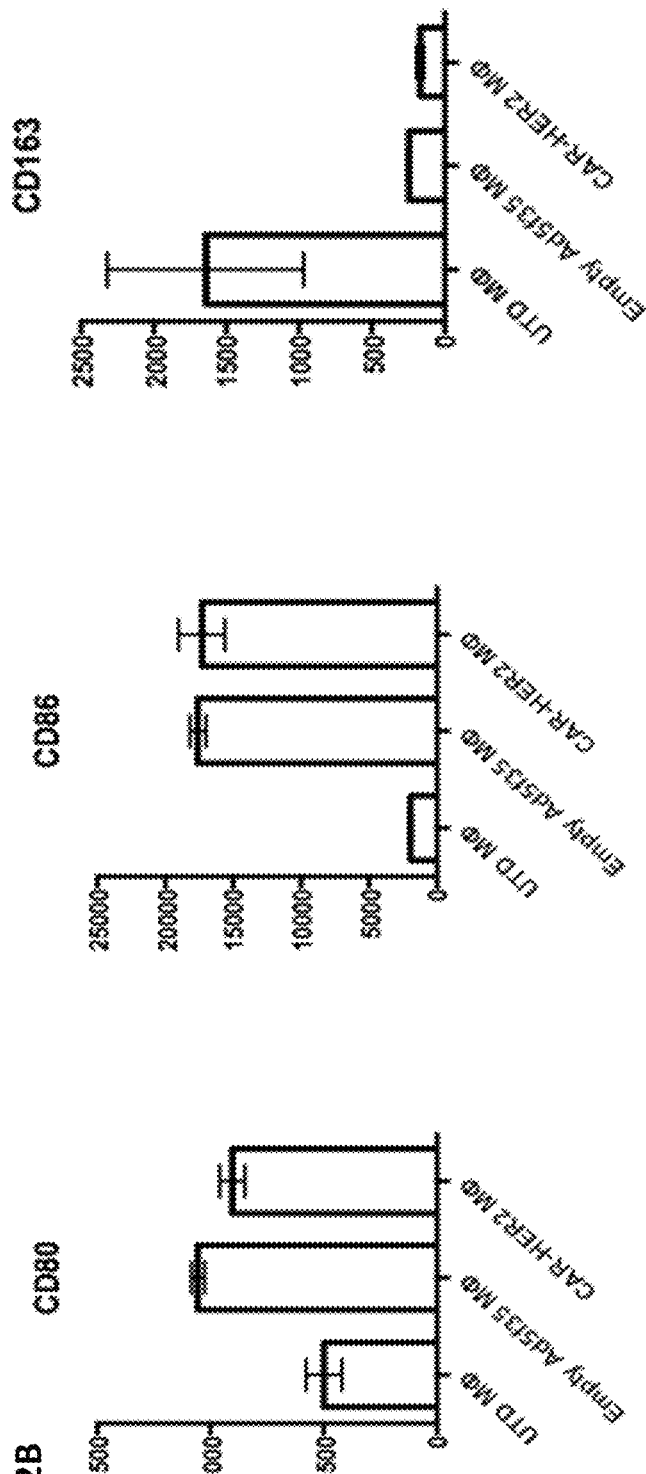
FIG. 22B is a series of graphs showing whether the effect on M1 and M2 markers was a result of CAR expression or Ad5f35 transduction. Macrophages were transduced with either nothing, empty Ad5f35, or anti-HER2 Ad5f35, and empty/CAR Ad5f35 showed the same pattern of phenotype shift.

Macrophages are phenotypically plastic cells capable of adopting diverse functional features, commonly separated into the M1 and M2 macrophage classifications—with M1 being inflammatory/activated, and M2 being immunosuppressive/tumor-promoting. 48 hours after transduction of primary human macrophages with Ad5f35 CAR virus, a dose dependent up-regulation of M1 markers CD80/CD86, and a dose dependent down-regulation of M2 marker CD163, were measured by FACS (FIG. 22A). To test whether this effect was a result of CAR expression or Ad5f35 transduction, macrophages were transduced with either nothing, empty Ad5f35, or anti-HER2 Ad5f35, and empty/CAR Ad5f35 showed the same pattern of phenotype shift (FIG. 22B).

Figure 22C:
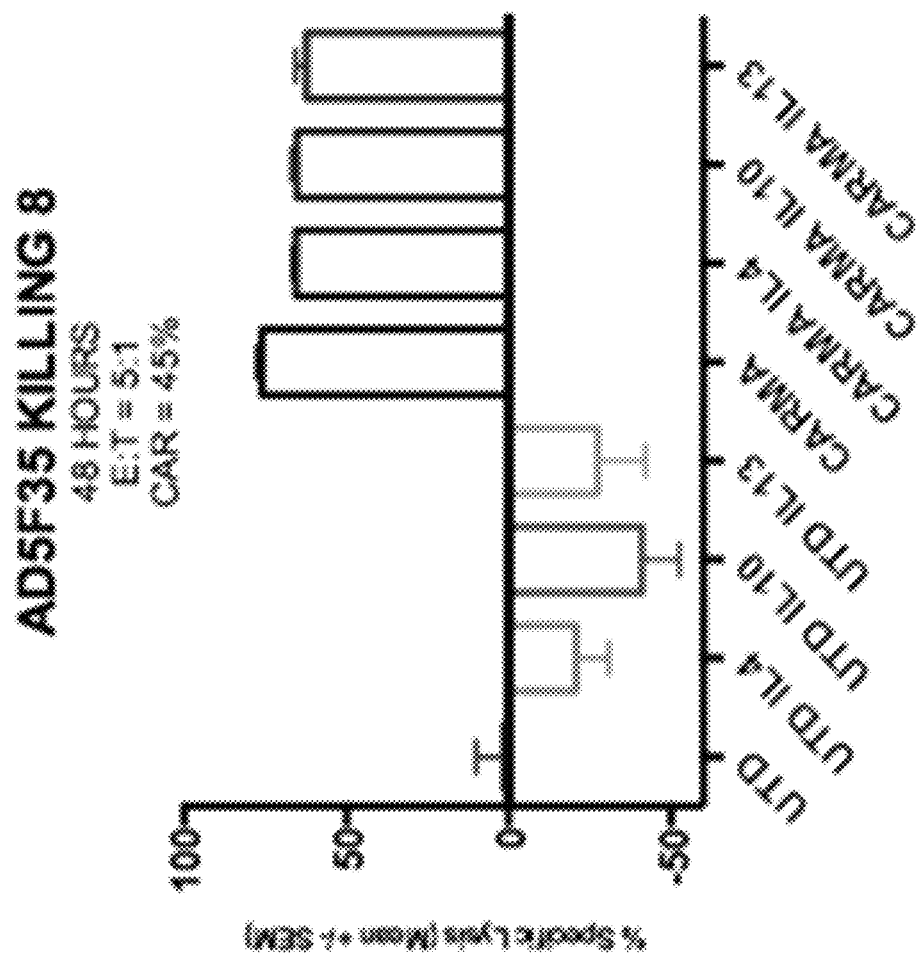
FIG. 22C is a graph showing that CARMA exposed to suppressive cytokines maintained their killing activity in a luciferase based in vitro specific lysis assay at 48 hours. Control UTD macrophages were conditioned with suppressive cytokines demonstrated enhanced tumor growth.

The solid tumor microenvironment is generally immunosuppressive and can lead to macrophage polarization to the M2 state. To test whether CARMA, which is M1 polarized due to viral transduction, is resistant to immunosuppressive cytokine mediated subversion to M2, control untransduced or anti-HER2 CAR human macrophages were exposed to IL-4, IL-10, or IL-13 for 24 hours prior to co-culture with SKOV3 ovarian cancer cells. Control UTD macrophages conditioned with suppressive cytokines led to the enhancement of tumor growth, while CARMA exposed to suppressive cytokines maintained their killing activity in a luciferase based in vitro specific lysis assay at 48 hours (FIG. 22C).

To further test the resistance to immunosuppression of human CAR macrophages, control UTD, Empty Ad5f35, or anti-HER2 CAR Ad5f35 transduced macrophages were exposed to 10 ng/mL of IL-4, a canonical M2 inducing cytokine, or cancer cells that were previously shown to subvert macrophages to M2 during co-culture (SKOV3, ovarian cancer cell line; HDLM2, Hodgkin lymphoma cell line). Control UTD macrophages upregulated CD206, an M2 marker that specifically responds to IL-4 stimulation via STAT6 phosphorylation. Empty Ad5f35, and more so CAR-Ad5f35 transduced macrophages, displayed resistance to IL-4 and tumor induced subversion to the M2 phenotype (FIG. 22D).

Figure 22E:
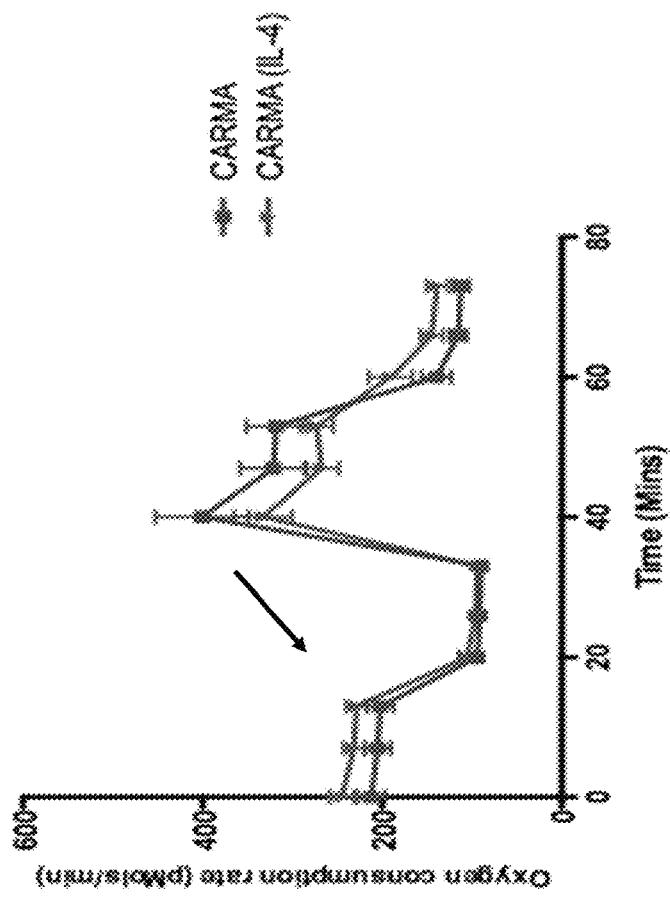
FIG. 22E is a graph showing metabolic phenotype of control UTD or anti-HER2 CAR macrophages exposed to IL-4 for 24 hours to polarize to M2 (or not), and oxygen consumption rate.
Figure 22F:
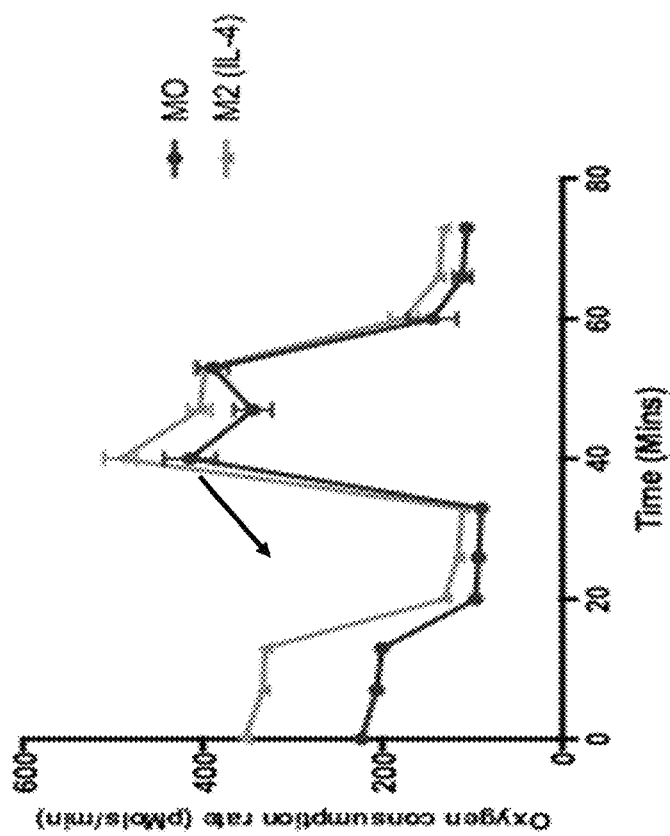
FIG. 22F is a graph showing that phenotypic, metabolic, and functional assays indicate that CARMA are resistant to M2 subversion.

In order to further characterize the phenotype of CAR macrophages, the metabolic phenotype was probed using the Seahorse assay to measure oxygen consumption. M2 macrophages have a higher basal oxygen consumption rate than M0 or M1 macrophages, due to a higher reliance on oxidative phosphorylation for ATP production. Control UTD or anti-HER2 CAR macrophages were exposed to IL-4 for 24 hours to polarize to M2 (or not), and oxygen consumption rate was measured. Control UTD macrophages demonstrated the characteristic increased basal oxygen consumption characteristic of M2 macrophages, while CARMA did not respond to IL-4, suggesting that it is resistant to M2 subversion (FIG. 22E). These data combined illustrate, using phenotypic, metabolic, and functional assays, that CARMA are resistant to M2 subversion.

Figure 23A:
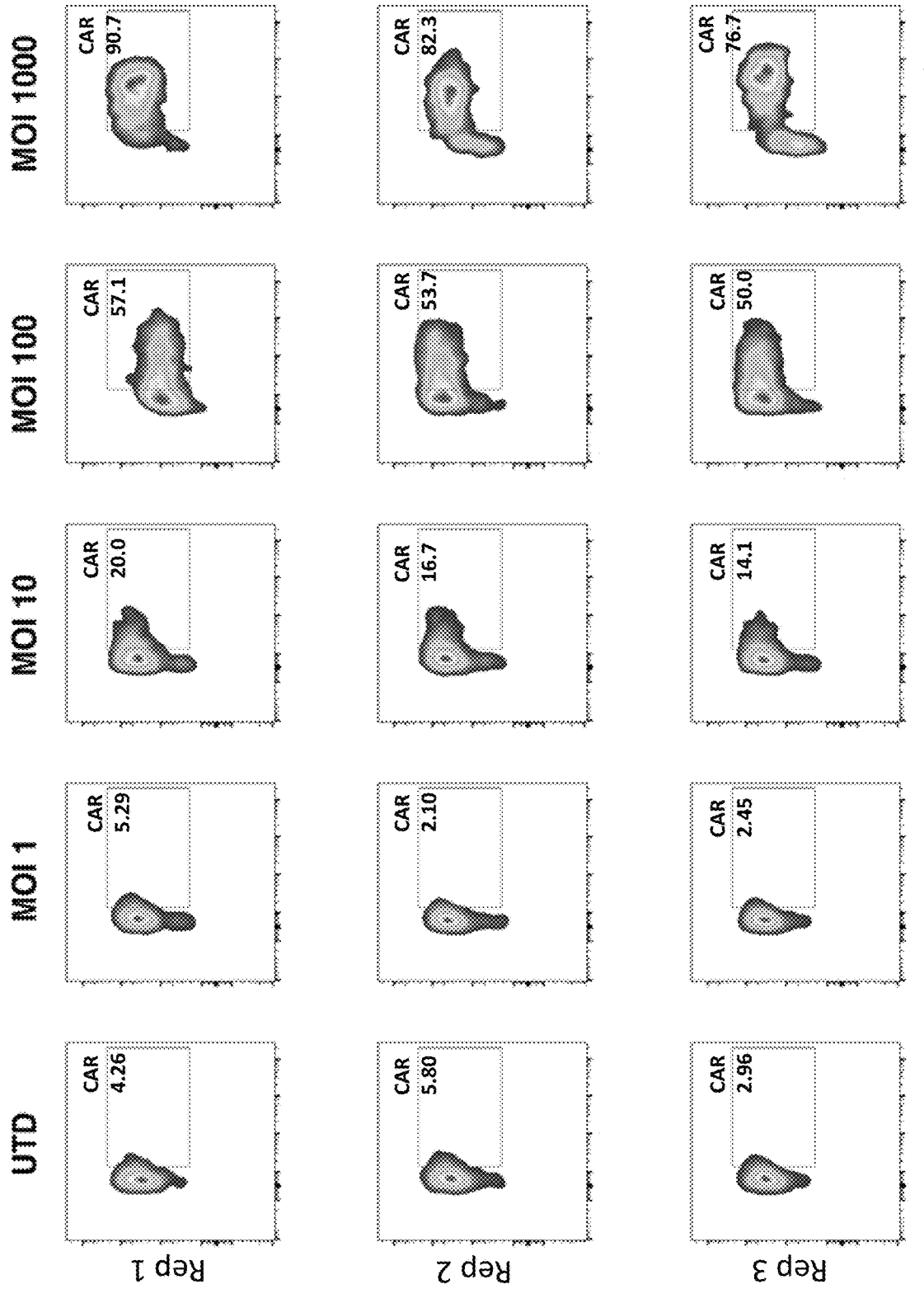
FIG. 23A is a panel of graphs showing primary human normal donor monocytes (purified via CD14 positive selection) transduced with Ad5f35-CAR-HER2 at MOI's ranging from 0 (UTD) to 1000. CAR expression was measured via FACS 48 hours post transduction. CAR monocytes were efficiently generated with Ad5f35, with expression peaking at an MOI of 1000.
Figure 23C:
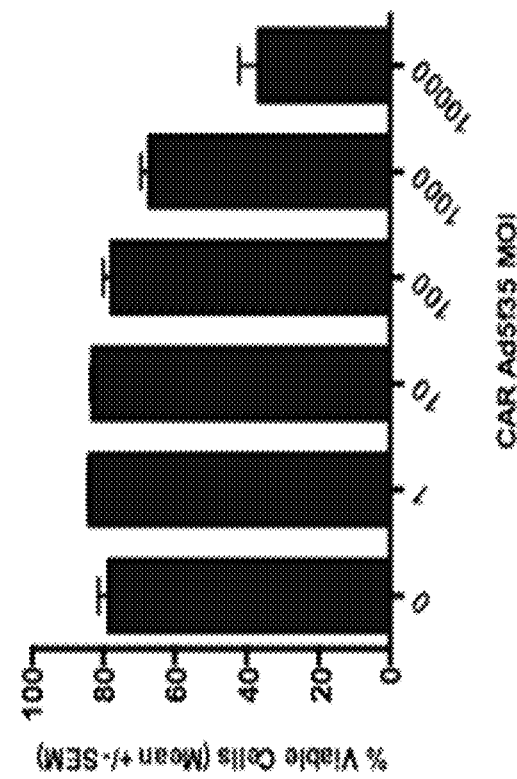
FIG. 23C is a graph showing that monocytes maintained high viability (measured by FACS Live/Dead Aqua analysis) at MOIs up to 1000.
Figure 23B:
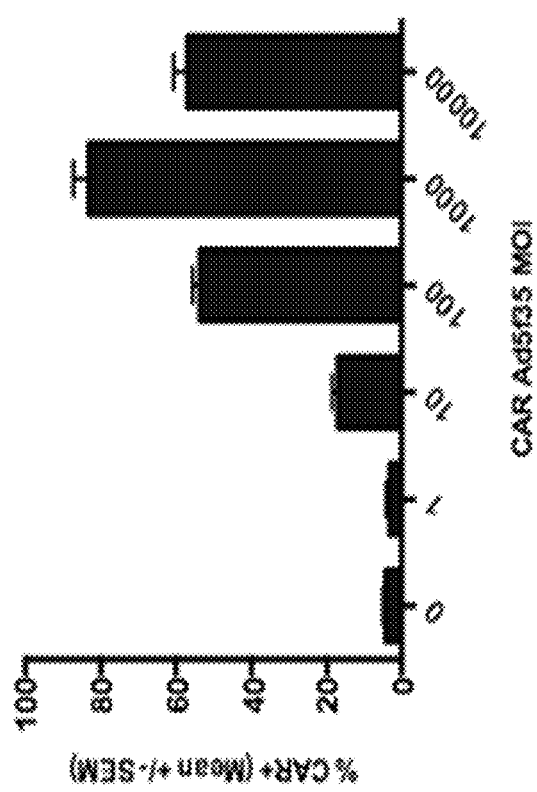
FIG. 23B is a graph showing primary monocyte transduction efficiency.
Figures 23D, 23E:
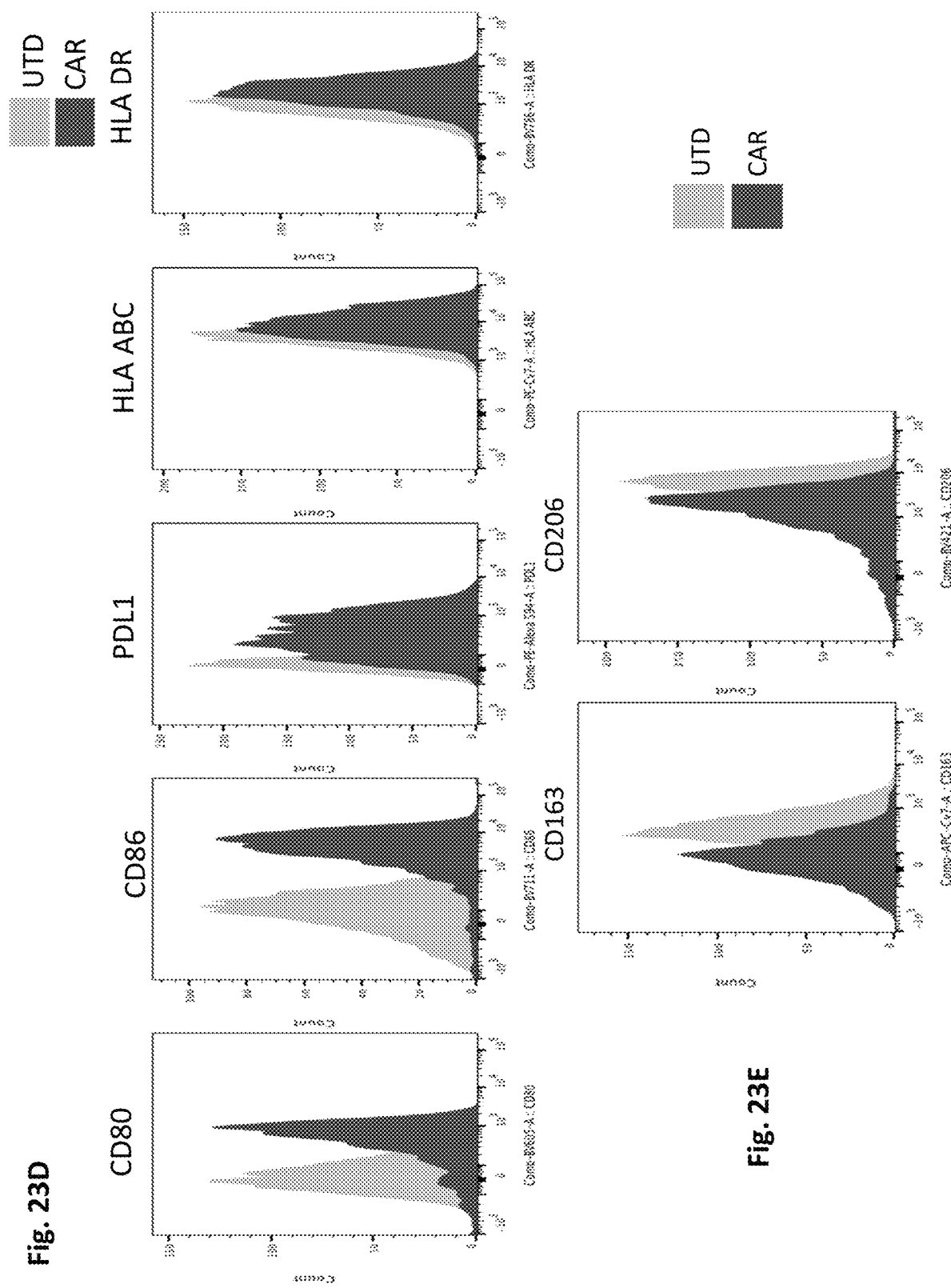
FIG. 23D is a series of graphs showing CAR but not untransduced (UTD) human monocytes upregulated M1 activation markers.
FIG. 23E is a series of graphs showing owing CAR but not untransduced (UTD) human monocytes downregulated M2 markers.

Primary human normal donor monocytes (purified via CD14 positive selection) were transduced with Ad5f35-CAR-HER2 at MOI's ranging from 0 (UTD) to 1000. CAR expression was measured via FACS 48 hours post transduction. CAR monocytes were efficiently generated with Ad5f35, with expression peaking at an MOI of 1000 (FIGS. 23A and 23B). Monocytes maintained high viability (measured by FACS Live/Dead Aqua analysis) at MOIs up to 1000 (FIG. 23C). CAR but not untransduced (UTD) human monocytes upregulated M1 activation markers (FIG. 23D) and downregulated M2 markers (FIG. 23E), as analyzed by FACS, demonstrating an M1 monocyte phenotype 48 hours post transduction.

Figure 24A:
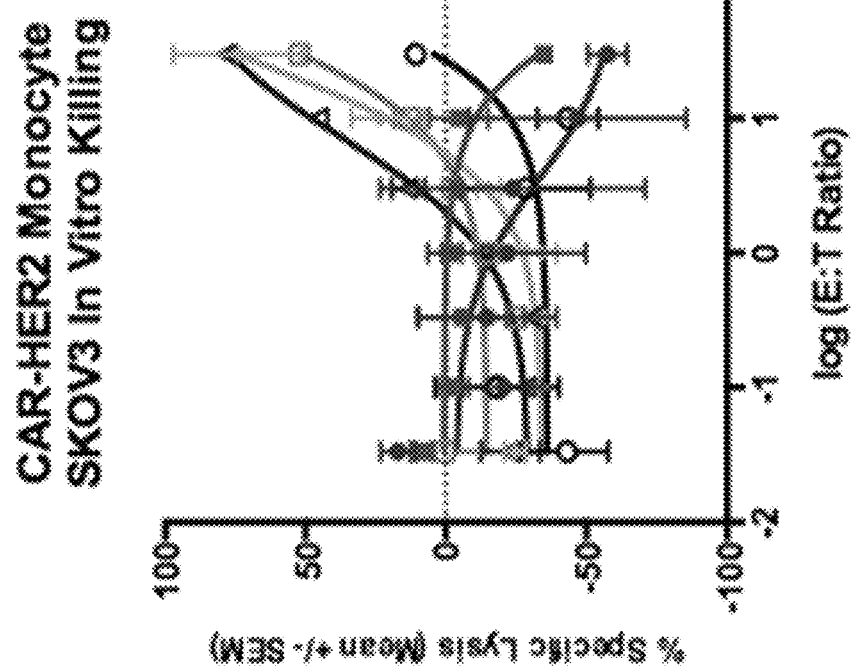
FIG. 24A is a graph showing anti-HER2 CAR monocyte killing of HER2+ SKBR3 cells (human breast cancer) assessed via an in vitro luciferase based killing assay.
Figure 24B:
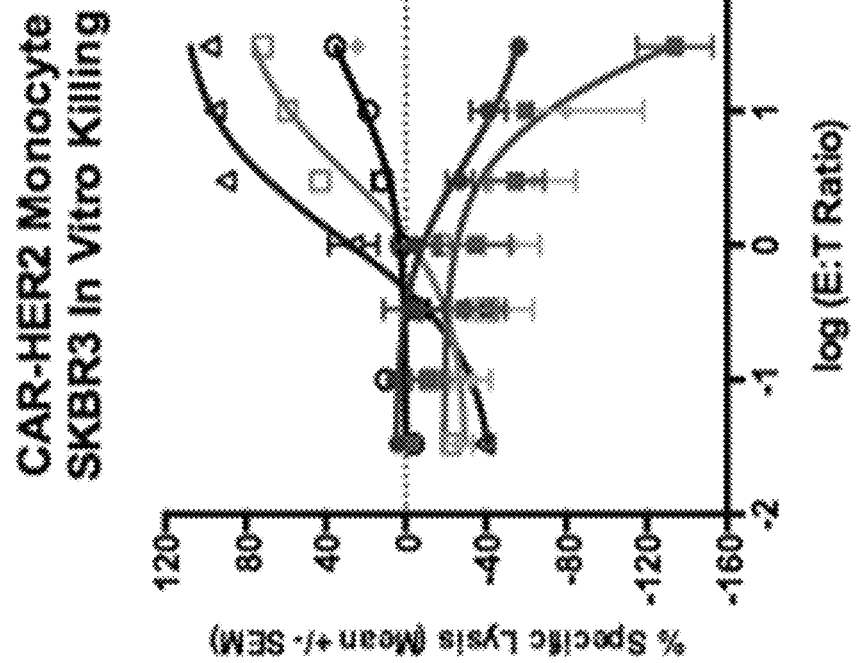
FIG. 24B is a graph showing anti-HER2 CAR monocyte killing of HER2+ SKOV3 cells (human ovarian cancer) assessed via an in vitro luciferase based killing assay.

Anti-HER2 CAR monocyte killing was assessed via in vitro luciferase based killing assay at a range of effector: target (E:T) ratios. Untransduced (UTD) or CAR-HER2-zeta (CAR) monocytes were co-cultured with either HER2+ SKBR3 (human breast cancer) or HER2+ SKOV3 (human ovarian cancer) cells in vitro. Specific lysis was calculated and determined at 24, 48, and 96 hours post initiation of co-culture. CAR but not UTD monocytes lysed both breast and ovarian cancer cells in vitro (FIGS. 24A and 24B).

Figure 25A:
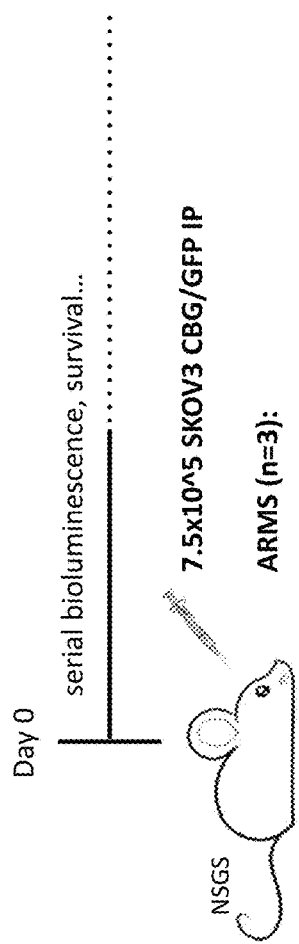
FIG. 25A is a schematic diagram of the NOD-scid IL2Rg-null-IL3/GM/SF, NSG-SGM3 (NSGS) mice used to model human HER2(+) ovarian cancer xenografts in vivo. On day 0 mice were injected intraperitoneally (IP) with 7.5E5 click beetle green luciferase (CBG luc) positive/green fluorescent protein (GFP) positive SKOV3 ovarian cancer cells as a model of intraperitoneal carcinomatosis, an aggressive inherently metastatic model of solid malignancy. Mice were either untreated (tumor alone), or injected with a single dose of 4E6 untransduced (UTD) or CAR-HER2 (CARMA) human macrophages on day 0 via IP injection.
Figure 25C:
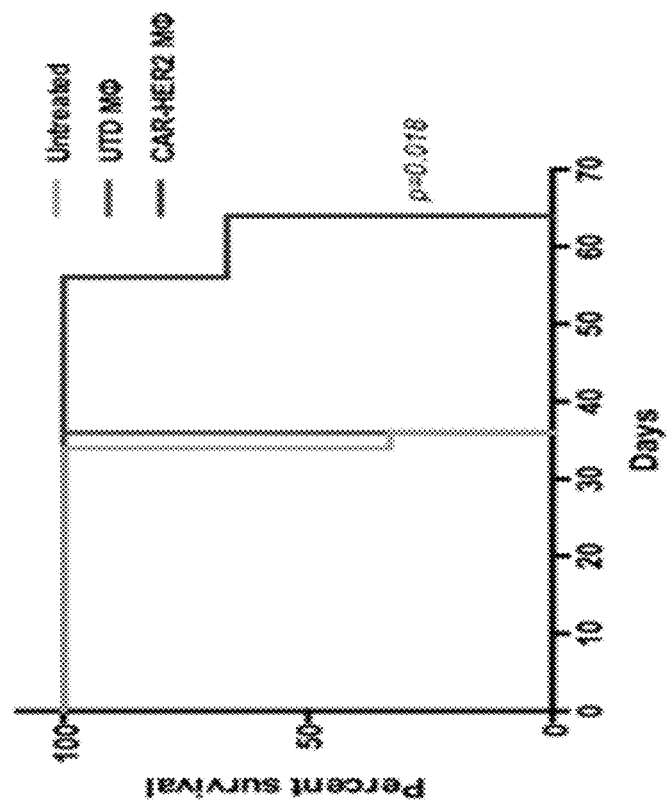
FIG. 25C is a graph showing percent survival of mice that received CARMA treatment. CARMA treated mice had a decrease in tumor burden of approximately two orders of magnitude.
Figure 25B:
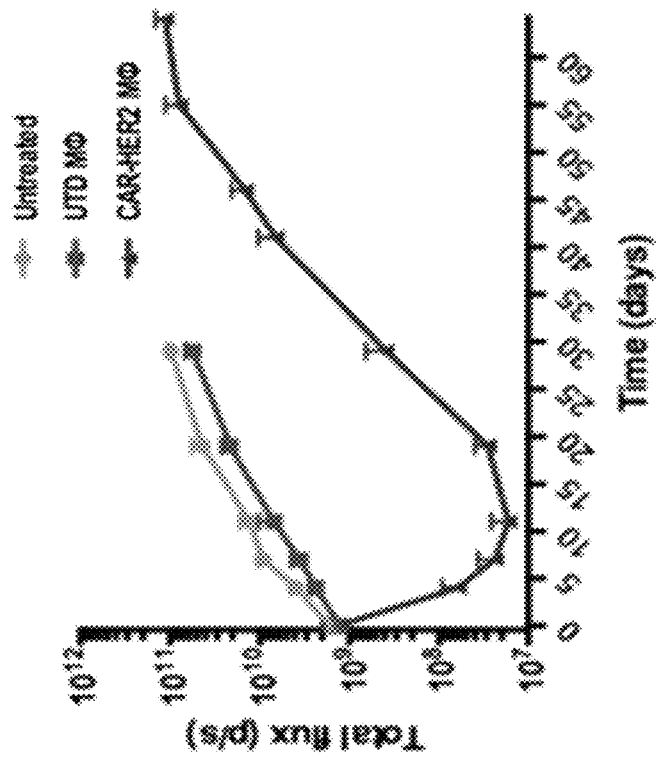
FIG. 25B is a graph showing mice serially imaged using bioluminescence (total flux; photons/second) as a surrogate of tumor burden.
Figure 25D:
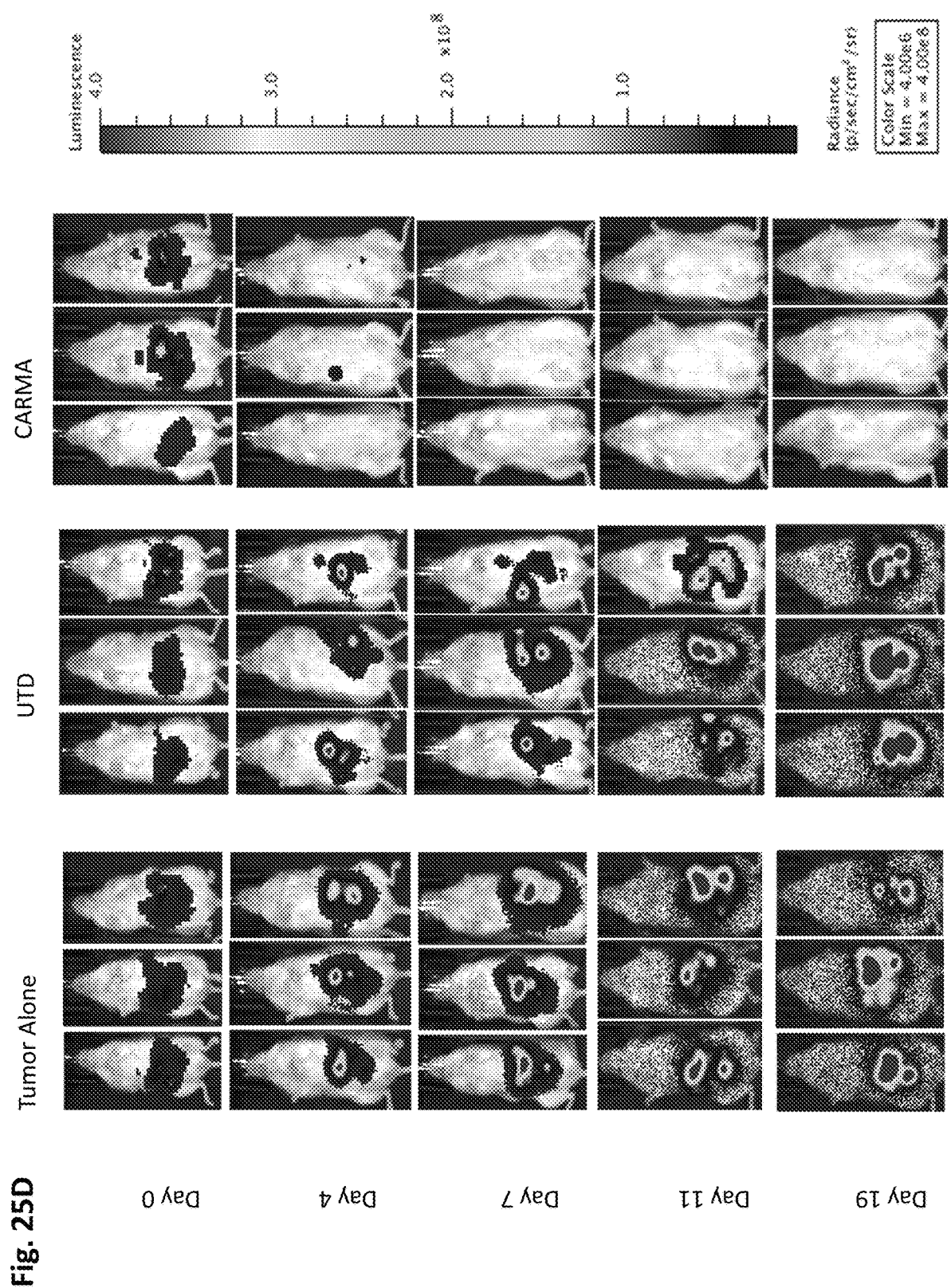
FIG. 25D is a panel of images showing that mice treated with CARMA had a 30 day survival benefit (p=0.018) relative to untreated or UTD macrophage treated mice.
Figure 25E:
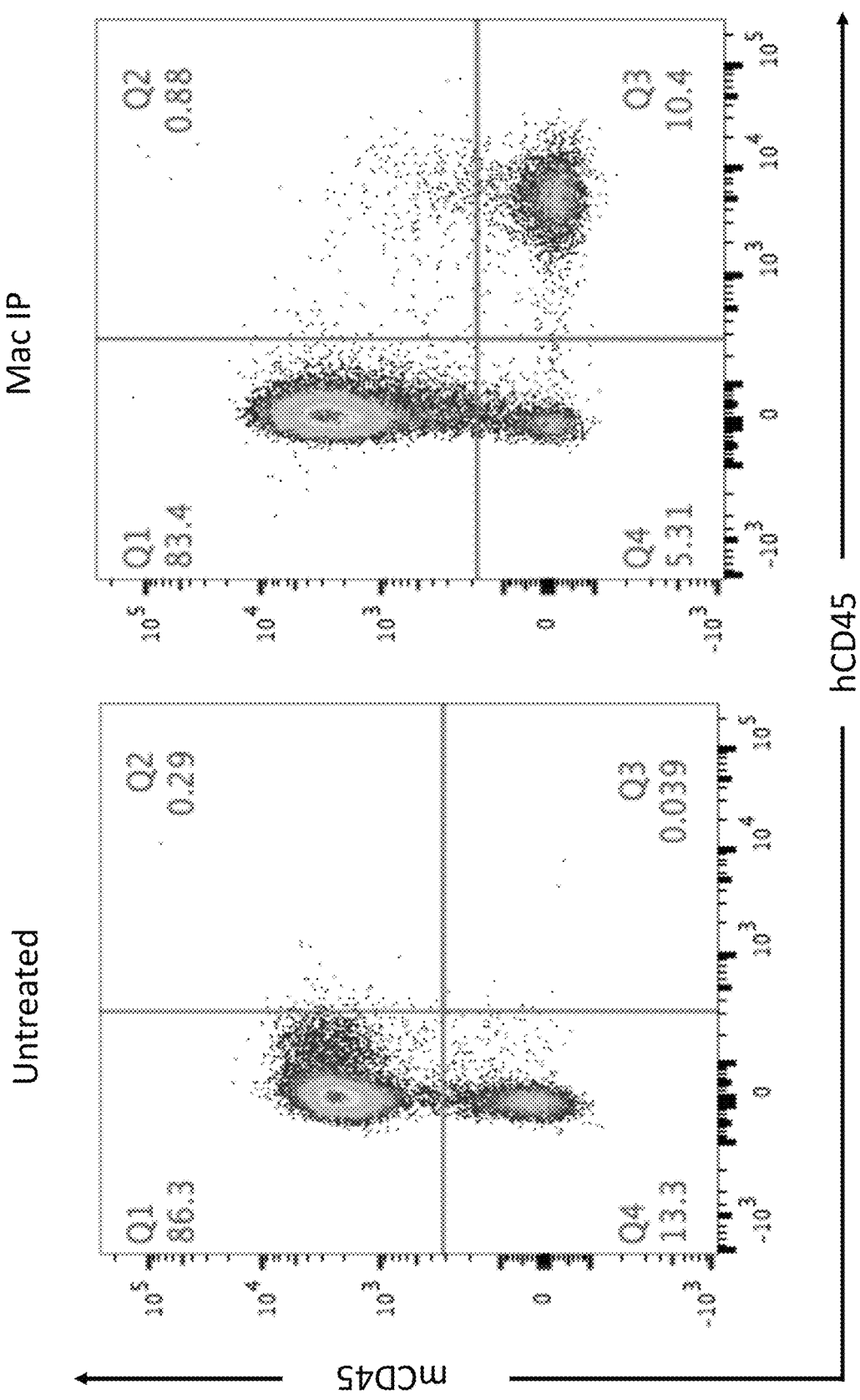
FIG. 25E is a panel of graphs showing tumors harvested from mice that died on day 36 and assessed for the presence of adoptively transferred human macrophages via human CD45 expression on FACS analysis.

NOD-scid IL2Rg-null-IL3/GM/SF, NSG-SGM3 (NSGS) mice were used to model human HER2(+) ovarian cancer xenografts in vivo. On day 0 mice were injected intraperitoneally (IP) with 7.5E5 click beetle green luciferase (CBG luc) positive/green fluorescent protein (GFP) positive SKOV3 ovarian cancer cells as a model of intraperitoneal carcinomatosis, an aggressive inherently metastatic model of solid malignancy. Mice were either untreated (tumor alone), or injected with a single dose of 4E6 untransduced (UTD) or CAR-HER2 (CARMA) human macrophages on day 0 via IP injection (schematic diagram, FIG. 25A). Mice were serially imaged using bioluminescence (total flux; photons/second) as a surrogate of tumor burden. Mice that received CARMA treatment had a decrease in tumor burden of approximately two orders of magnitude (FIGS. 25B and 25C). Mice treated with CARMA had a 30 day survival benefit (p=0.018) relative to untreated or UTD macrophage treated mice (FIG. 25D). To demonstrate trafficking of macrophages into the solid tumor nodule, tumors were harvested from mice that died on day 36 and assessed for the presence of adoptively transferred human macrophages via human CD45 expression on FACS analysis (FIG. 25E).

Figure 26A:
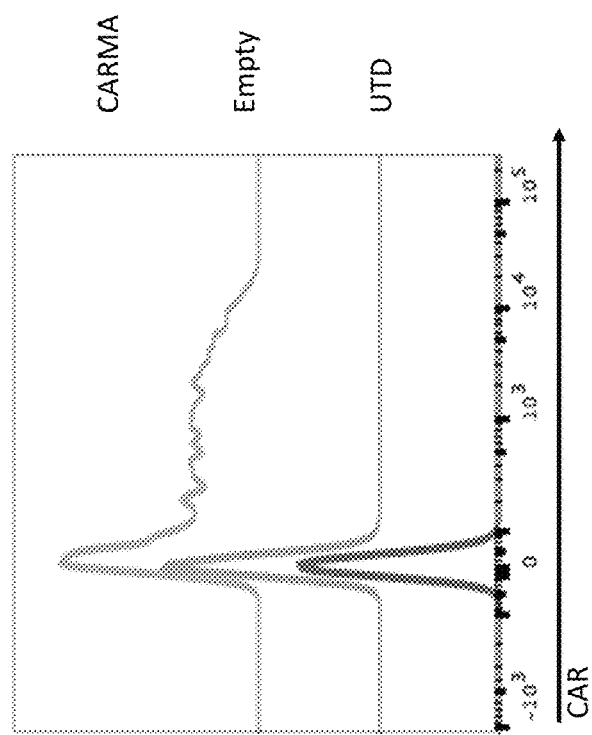
FIG. 26A is a graph showing surface CAR expression verified by FACS analysis 48 hours post transduction of human macrophages either untransduced (UTD) or transduced with empty Ad5f35 virions lacking a transgene (Empty) or Ad5f35-CAR-HER2-ζ (CARMA) at multiplicities of infection of 1000.
Figure 26B:
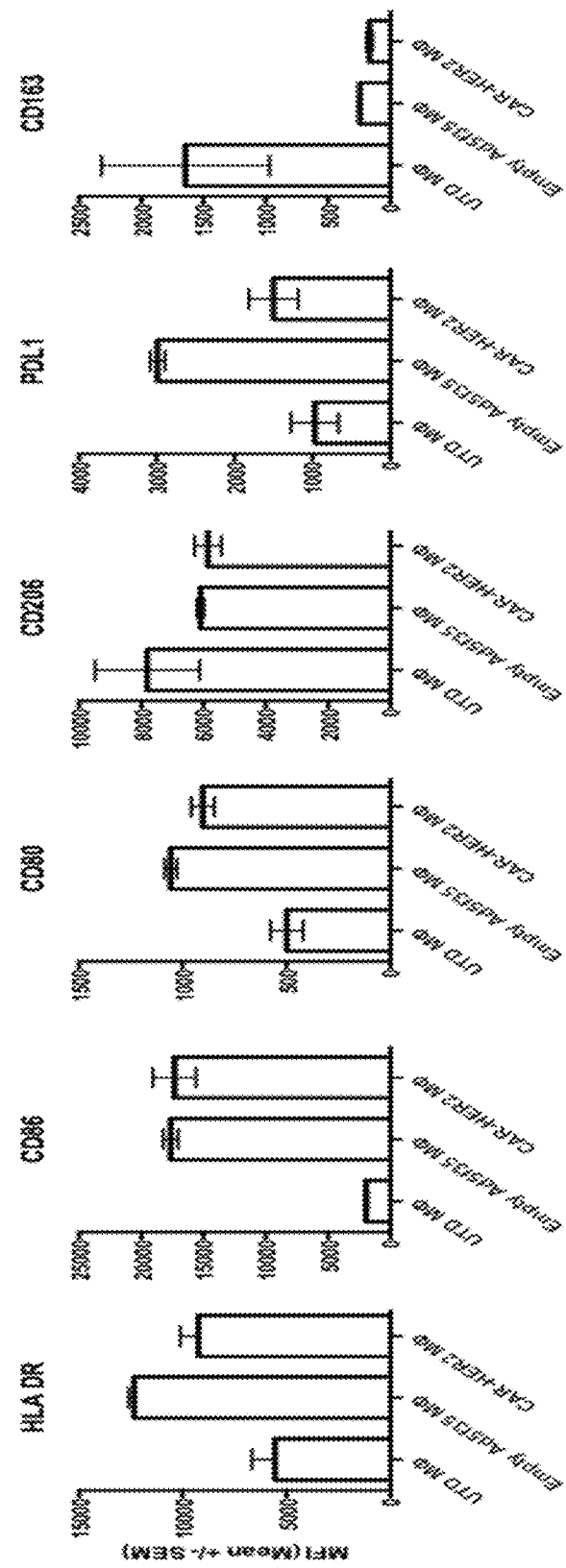
FIG. 26B is a panel of graphs showing surface markers assessed to demonstrate M1 macrophage polarization in cells transduced by either empty Ad5f35 or CAR-HER2-ζ Ad5f35. M1 markers (HLA DR, CD86, CD80, PDL1) were upregulated while M2 markers (CD206, CD163) were downregulated
Figure 26C:
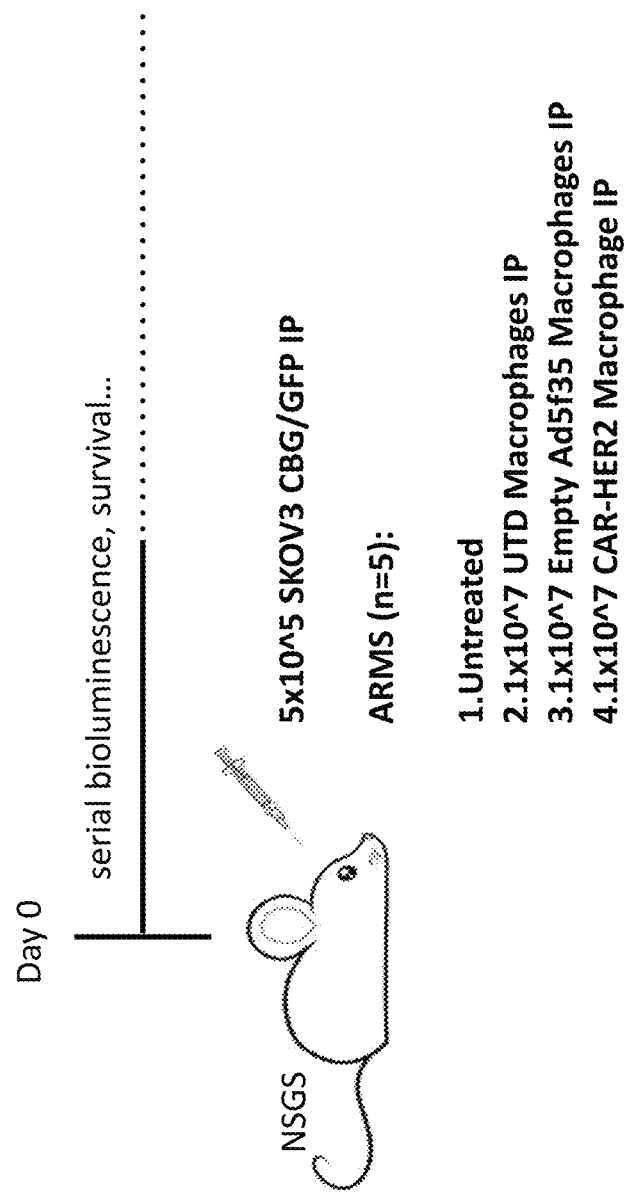
FIG. 26C is a schematic diagram of the NSGS mice used in an IP model of HER2+ metastatic ovarian cancer, and stratified into four treatment arms (n=5 per arm). Mice were left untreated or given IP injections of 1E7 untransduced, empty-Ad5f35 transduced macrophages, or CAR-HER2-ζ transduced macrophages on day 0.
Figure 26D:
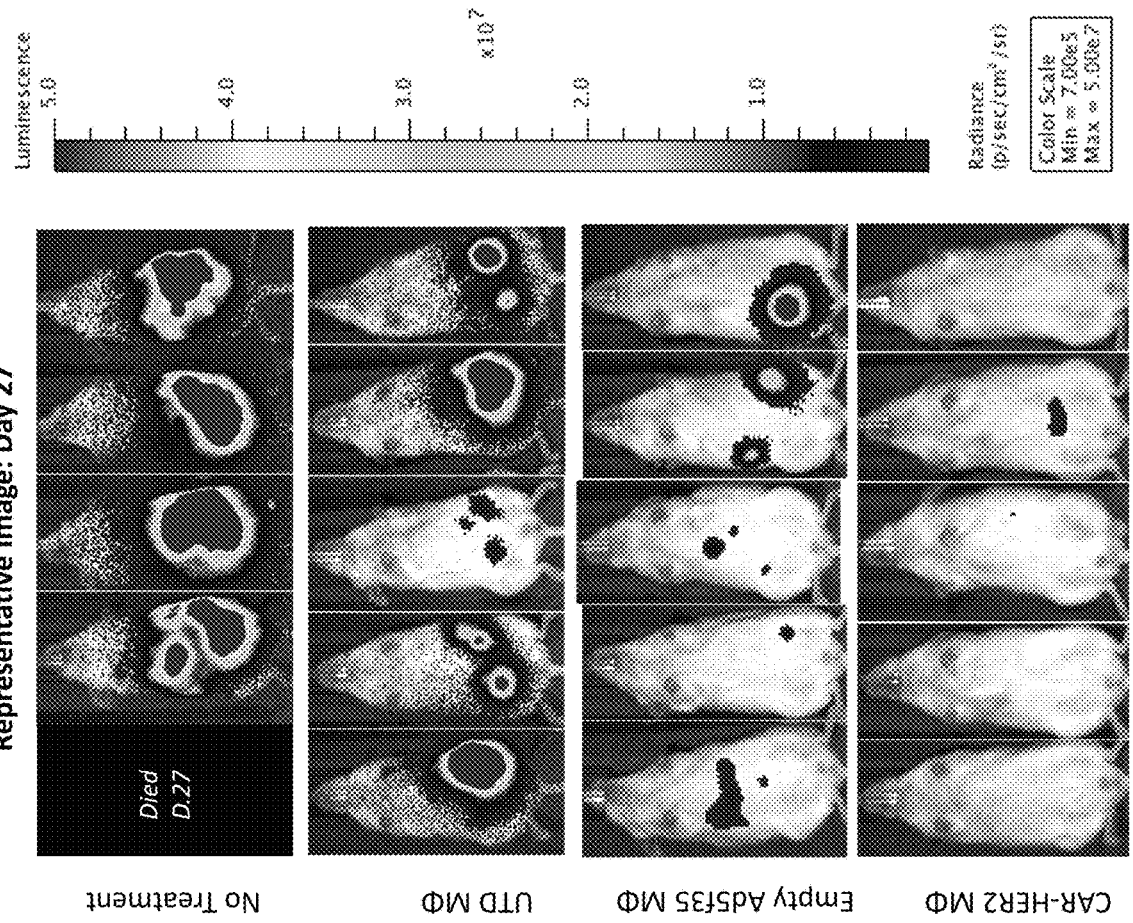
FIG. 26D is a panel of images showing tumor burden monitored via serial bioluminescent imaging, with representative data shown at day 27 post tumor engraftment.
Figure 26E:
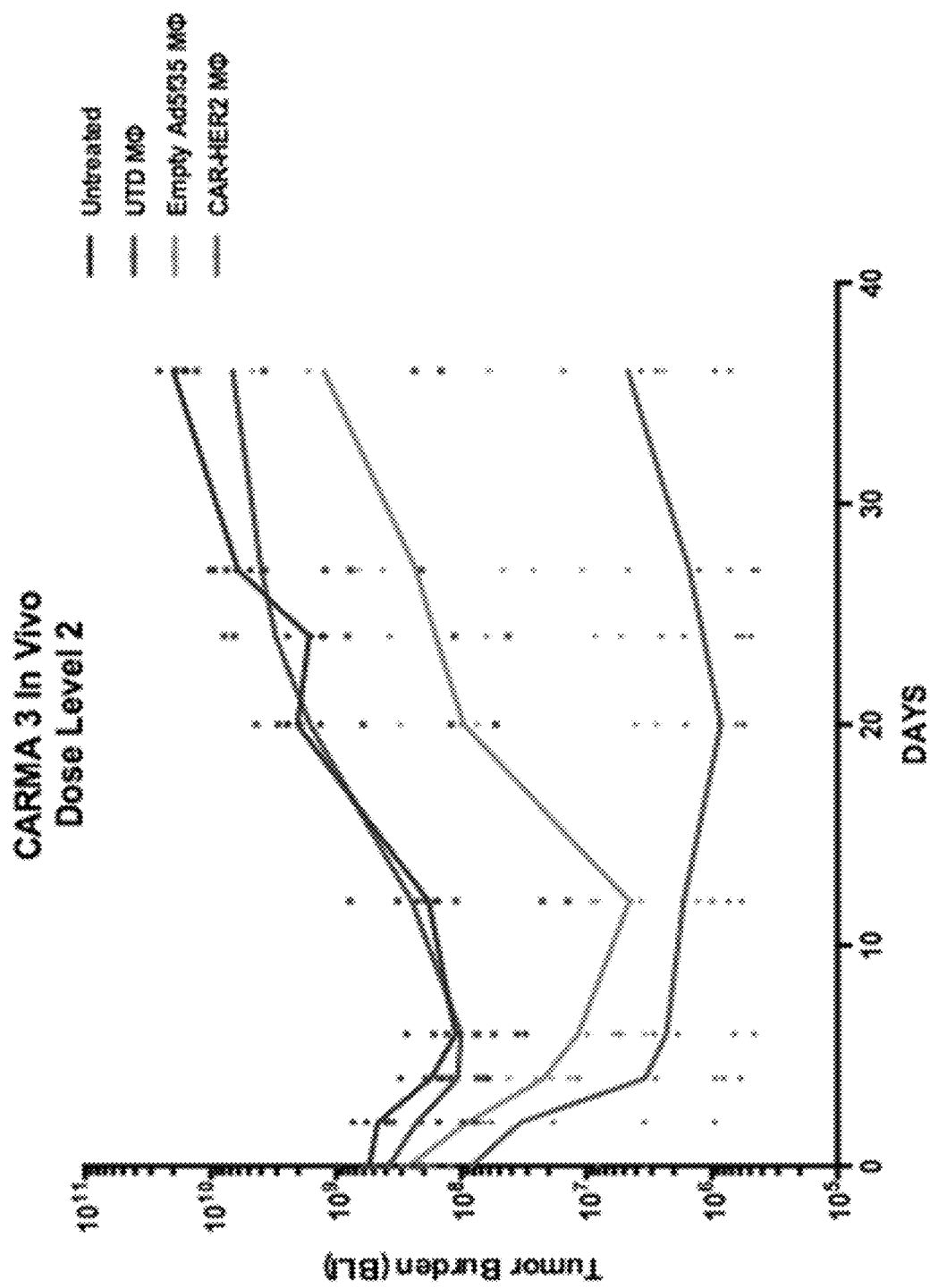
FIG. 26E is a graph showing tumor burden monitored via serial bioluminescent imaging, with representative data shown at day 27 post tumor engraftment.

Human macrophages were either untransduced (UTD) or transduced with empty Ad5f35 virions lacking a transgene (Empty) or Ad5f35-CAR-HER2-ζ (CARMA) at multiplicities of infection of 1000. Surface CAR expression was verified by FACS analysis 48 hours post transduction (FIG. 26A). Surface markers were assessed to demonstrate M1 macrophage polarization in cells transduced by either empty Ad5f35 or CAR-HER2-ζ Ad5f35. M1 markers (HLA DR, CD86, CD80, PDL1) were upregulated while M2 markers (CD206, CD163) were downregulated (FIG. 26B). NSGS mice were again used in an IP model of HER2+ metastatic ovarian cancer, and were stratified into four treatment arms (n=5 per arm). Mice were left untreated or given IP injections of 1E7 untransduced, empty-Ad5f35 transduced macrophages, or CAR-HER2-ζ transduced macrophages on day 0 (FIG. 26C). Tumor burden was monitored via serial bioluminescent imaging, with representative data shown at day 27 post tumor engraftment (FIGS. 26D and 26E). CARMA treated mice had roughly 2,400 fold less tumor burden than untreated mice at day 20 post treatment.

Figure 27C:
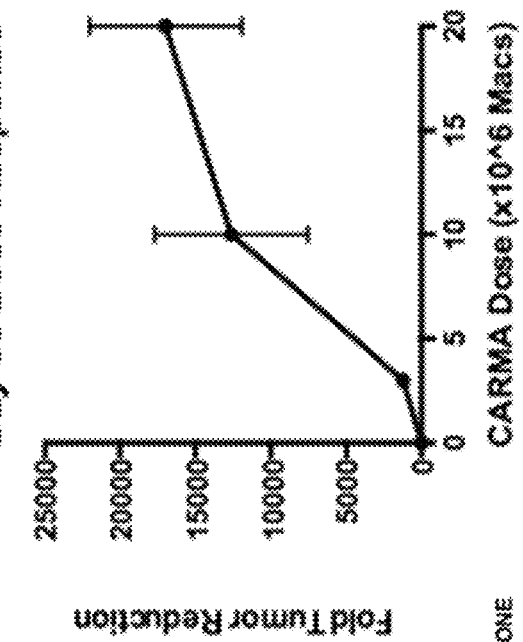
FIG. 27C is a graph showing that single doses of CAR-HER2 macrophages at 3E6, 1E7, or 2E7 macrophages per mouse led to dose dependent tumor eradication (relative to untreated mice) by day 36 post engraftment.
Figure 27A:
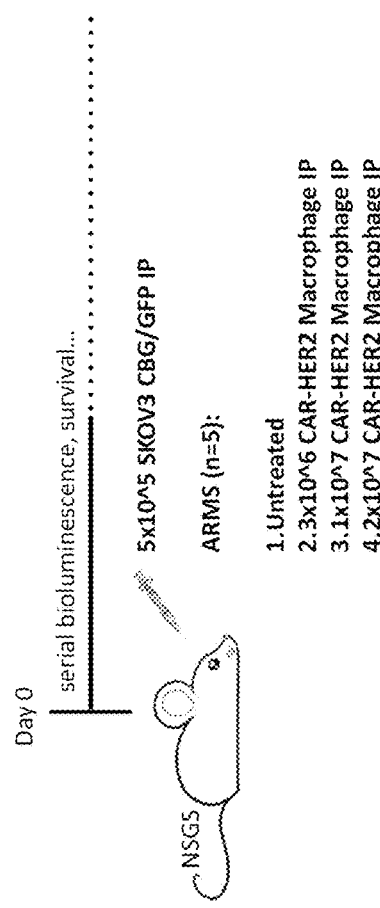
FIG. 27A is a schematic diagram of the NSGS mice used in an IP model of HER2+ metastatic ovarian cancer, and stratified into four treatment arms (n=5 per arm), including no treatment, and either 3E6, 1E7, or 2E7 CAR-HER2-ζ human macrophages, administered IP on day 0.
Figure 27B:
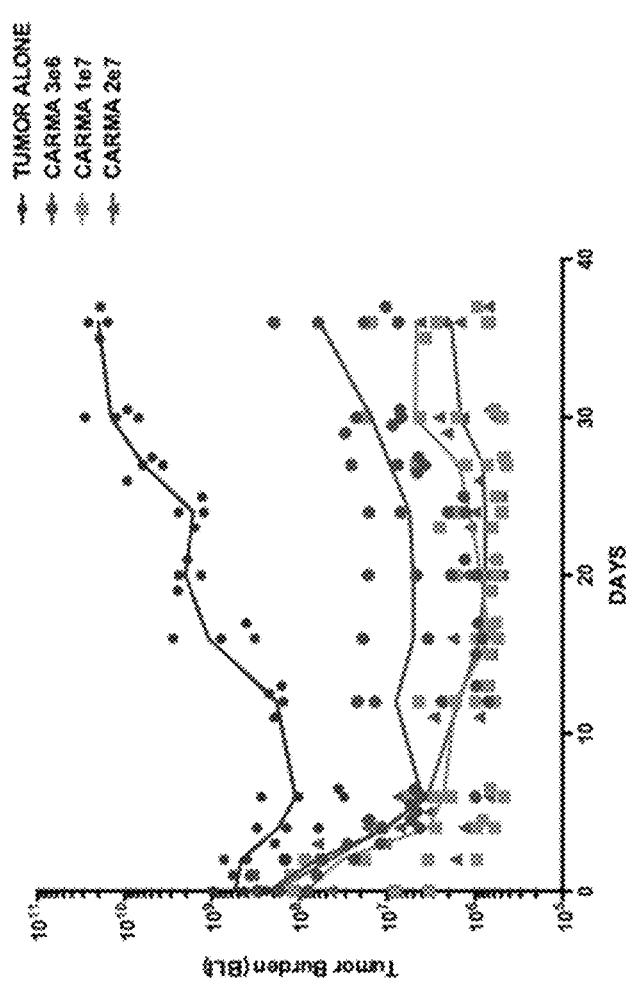
FIG. 27B is a graph showing tumor burden monitored via serial bioluminescent imaging. A dose-dependent response to the number of macrophage was observed in this model.

NSGS mice were used in an IP model of HER2+ metastatic ovarian cancer, and were stratified into four treatment arms (n=5 per arm), including no treatment, and either 3E6, 1E7, or 2E7 CAR-HER2-ζ human macrophages, administered IP on day 0 (FIG. 27A). Tumor burden was monitored via serial bioluminescent imaging, and a macrophage number dependent dose response was observed in this model (FIG. 27B). Single doses of CAR-HER2 macrophages at 3E6, 1E7, or 2E7 macrophages per mouse led to dose dependent tumor eradication (relative to untreated mice) by day 36 post engraftment (FIG. 27C).

Figure 28:
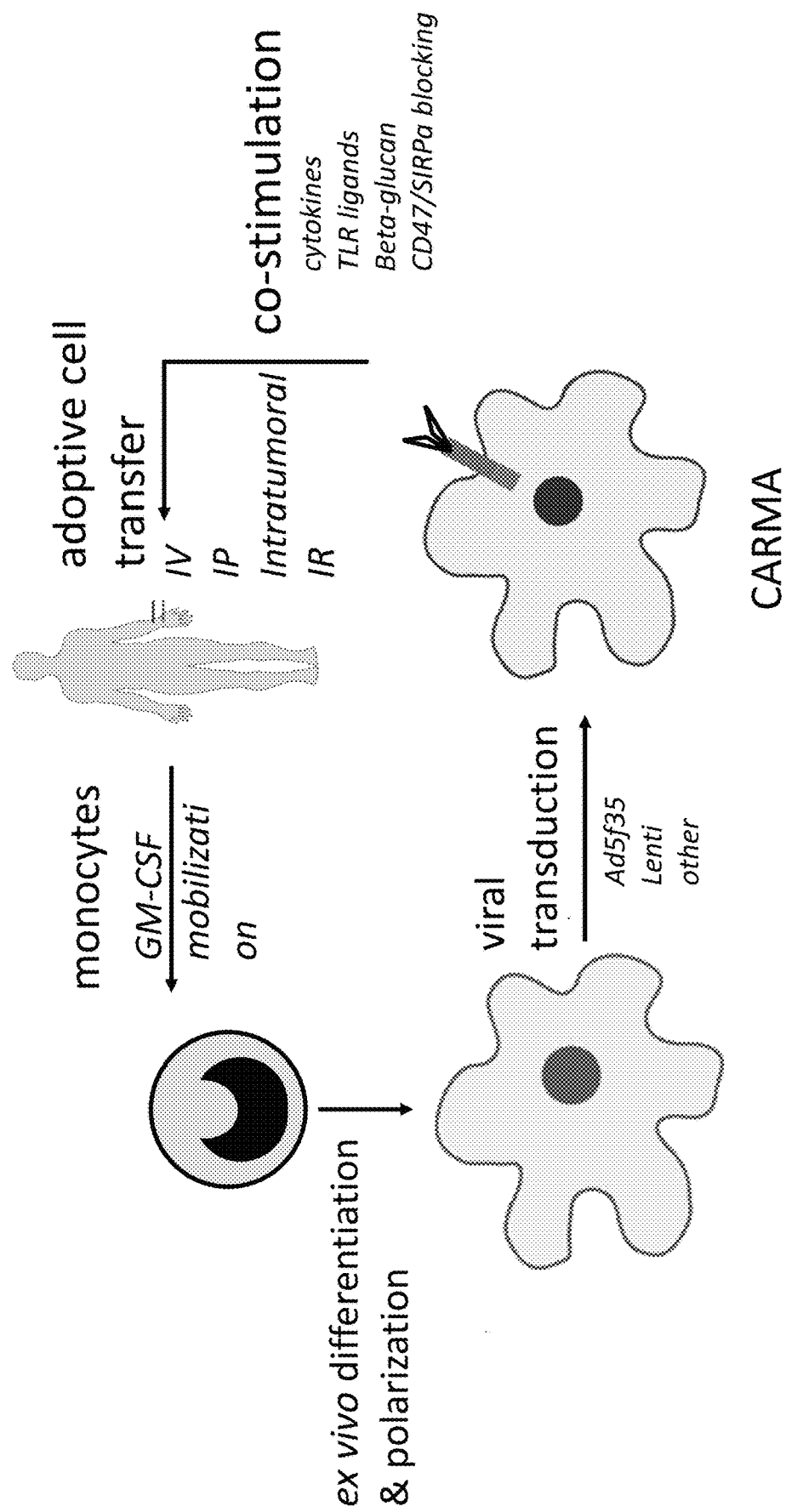
FIG. 28 is an illustration of the proposed therapeutic approach for CARMA. In brief, patient monocytes would be selected from the peripheral blood, ex vivo differentiated and transduced to express a CAR, co-stimulated (or not) with synergistic compounds, and injected back into the patient either intravenously, intraperitoneally, intratumorally, via interventional radiological procedure, or by other route. Of note, the differentiated process could be skipped and monocytes can be transduced and infused back into the patient. The monocyte source may also be an HLA matched donor.

FIG. 28 is an illustration of the proposed therapeutic approach for CARMA. In brief, patient monocytes would be selected from the peripheral blood, ex vivo differentiated and transduced to express a CAR, co-stimulated (or not) with synergistic compounds, and injected back into the patient either intravenously, intraperitoneally, intratumorally, via interventional radiological procedure, or by other route. Of note, the differentiated process could be skipped and monocytes can be transduced and infused back into the patient. The monocyte source may also be an HLA matched donor.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A modified macrophage or monocyte comprising a chimeric antigen receptor (CAR),
    wherein the CAR comprises an antigen binding domain, a transmembrane domain and an intracellular domain of a stimulatory and/or co-stimulatory molecule, and
    wherein the modified macrophage or monocyte exhibits reduced SIRPα activity relative to an unmodified cell.

2. The modified macrophage or monocyte of claim 1, wherein the modified macrophage or monocyte comprises deletion of SIRPα using CRISPR/Cas9.

3. The modified macrophage or monocyte of claim 1, wherein the modified macrophage or monocyte has been treated with an anti-SIRPα antibody.

4. The modified macrophage or monocyte of claim 1, wherein the modified macrophage or monocyte comprises anti-SIRPα antibodies.

5. The modified macrophage or monocyte of claim 1, wherein the modified macrophage or monocyte comprises anti-SIRPα siRNA.

6. The modified macrophage or monocyte of claim 1, wherein the modified macrophage or monocyte exhibits increased targeted effector activity relative to an unmodified cell.

7. The modified macrophage or monocyte of claim 6, wherein the increased targeted effector activity is directed against a target cell comprising an antigen that specifically binds the antigen binding domain of the CAR.

8. The modified macrophage or monocyte of claim 6, wherein the targeted effector activity is selected from the group consisting of phagocytosis, targeted cellular cytotoxicity, antigen presentation, and cytokine secretion.

9. The modified macrophage or monocyte of claim 1, wherein the antigen binding domain of the CAR comprises an antibody selected from the group consisting of a monoclonal antibody, a polyclonal antibody, a synthetic antibody, human antibody, humanized antibody, single domain antibody, single chain variable fragment, and antigen-binding fragments thereof.

10. The modified macrophage or monocyte of claim 1, wherein the antigen binding domain of the CAR is selected from the group consisting of an anti-CD19 antibody, an anti-HER2 antibody, and a fragment thereof.

11. The modified macrophage or monocyte of claim 1, wherein the transmembrane domain of the CAR comprises a CD8 or CD28 transmembrane domain.

12. The modified macrophage or monocyte of claim 1, wherein the intracellular domain of the CAR comprises dual signaling domains.

13. The modified macrophage or monocyte of claim 1, wherein the intracellular domain of the CAR comprises a CD3 zeta intracellular domain.

14. The modified macrophage or monocyte of claim 1, further comprising an agent selected from the group consisting of a nucleic acid, an antibiotic, an anti-inflammatory agent, an antibody or antibody fragments thereof, a growth factor, a cytokine, an enzyme, a protein, a peptide, a fusion protein, a synthetic molecule, an organic molecule, a carbohydrate or the like, a lipid, a hormone, a microsome, a derivative or a variation thereof, and any combination thereof.

15. A pharmaceutical composition comprising the modified macrophage or monocyte of claim 1 and a pharmaceutically acceptable carrier.

16. A method of treating a disease or condition associated with a tumor or cancer in a subject comprising:
   administering to the subject a therapeutically effective amount of a pharmaceutical composition comprising the modified macrophage or monocyte of claim 1.

17. A method of modifying a macrophage or monocyte, comprising:
   introducing a nucleic acid encoding a chimeric antigen receptor (CAR) into the macrophage or monocyte,
   wherein the CAR comprises an antigen binding domain, a transmembrane domain and an intracellular domain of a stimulatory and/or co-stimulatory molecule, and
   introducing CRISPR/Cas9 gene editing material into the macrophage or monocyte,
   wherein the modified macrophage or monocytes exhibits targeted effector activity and reduced SIRPα activity.

18. A method of modifying a macrophage or monocyte, comprising:
   introducing a nucleic acid encoding a chimeric antigen receptor (CAR) into the macrophage or monocyte,
   wherein the CAR comprises an antigen binding domain, a transmembrane domain and an intracellular domain of a stimulatory and/or co-stimulatory molecule, and
   wherein the macrophage or monocyte is engineered to encode an siRNA that downregulates SIRPα,
   wherein the modified macrophage or monocytes exhibits targeted effector activity and reduced SIRPα activity.

19. A method of modifying a macrophage or monocyte, comprising:
   introducing a nucleic acid encoding a chimeric antigen receptor (CAR) into the macrophage or monocyte,
   wherein the CAR comprises an antigen binding domain, a transmembrane domain and an intracellular domain of a stimulatory and/or co-stimulatory molecule, and
   wherein the macrophage or monocyte is capable of secreting an anti-SIRPα antibody,
   wherein the modified macrophage or monocytes exhibits targeted effector activity and reduced SIRPα activity.

20. The method of claim 17, wherein introducing the CAR into the macrophage or monocyte comprises introducing a nucleic acid sequence encoding the CAR.

21. The method of claim 17, wherein the targeted effector activity is directed against a target cell comprising an antigen that specifically binds the antigen binding domain of the CAR.

22. The method of claim 17, wherein the targeted effector activity is selected from the group consisting of phagocytosis, targeted cellular cytotoxicity, antigen presentation, and cytokine secretion.

23. The method of claim 17, wherein the antigen binding domain of the CAR comprises an antibody selected from the group consisting of a monoclonal antibody, a polyclonal antibody, a synthetic antibody, human antibody, humanized antibody, single domain antibody, single chain variable fragment, and antigen-binding fragments thereof.

24. The method of claim 17, wherein the antigen binding domain of the CAR is selected from the group consisting of an anti-CD19 antibody, an anti-HER2 antibody, and a fragment thereof.

* * * * *